(12) United States Patent
McGrail et al.

(10) Patent No.: US 11,851,712 B2
(45) Date of Patent: Dec. 26, 2023

(54) REPLICATION STRESS RESPONSE BIOMARKERS FOR IMMUNOTHERAPY RESPONSE

(71) Applicant: Board of Regents, The University of Texas System, Austin, TX (US)

(72) Inventors: Daniel McGrail, Houston, TX (US); Shiaw-Yih Lin, Houston, TX (US); Patrick Pilie, Houston, TX (US); Eric Jonasch, Houston, TX (US); Curtis Chun-Jen Lin, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/978,758

(22) PCT Filed: Mar. 6, 2019

(86) PCT No.: PCT/US2019/020921
§ 371 (c)(1),
(2) Date: Sep. 7, 2020

(87) PCT Pub. No.: WO2019/173456
PCT Pub. Date: Sep. 12, 2019

(65) Prior Publication Data
US 2021/0130906 A1 May 6, 2021

Related U.S. Application Data

(60) Provisional application No. 62/661,383, filed on Apr. 23, 2018, provisional application No. 62/639,439, filed on Mar. 6, 2018.

(51) Int. Cl.
*C12Q 1/6886* (2018.01)
*C12Q 1/6813* (2018.01)

(52) U.S. Cl.
CPC ......... *C12Q 1/6886* (2013.01); *C12Q 1/6813* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2009/0226905 A1* | 9/2009 | Joubert | G01N 33/57419 435/7.1 |
| 2015/0030615 A1* | 1/2015 | Derr | C12Q 1/6886 424/174.1 |
| 2015/0275306 A1* | 10/2015 | Bernards | G01N 33/57484 506/9 |
| 2016/0010159 A1 | 1/2016 | Lin et al. | |
| 2017/0000885 A1 | 1/2017 | Rhee et al. | |
| 2017/0107577 A1 | 4/2017 | Al-Ejeh | |
| 2018/0202004 A1* | 7/2018 | Knudsen | A61P 35/00 |

FOREIGN PATENT DOCUMENTS

| | | |
|---|---|---|
| WO | WO 2009/132126 | 10/2009 |
| WO | WO 2016/078670 | 5/2016 |
| WO | WO 2016/130581 | 8/2016 |
| WO | WO 2016/149366 | 9/2016 |

OTHER PUBLICATIONS

Mouw et al Cancer Discov. Published online Jun. 19, 2017. 7(7): 675-693 (Year: 2017).*
Hanke et al. Clinical Chemistry. 2007. 53: 2070-2077 (Year: 2007).*
Palmer et al. BMC Genomics. 2006. 7:115 (Year: 2006).*
Min et al. BMC Genomics. 2010. 11:96 (Year: 2010).*
Tuttle et al. PLoS ONE. Jan. 2014. 9: e87325 (Year: 2014).*
Haynes et al. Electrophoresis. 1998. 19: 1862-1871 (Year: 1998).*
Chen et al. Molecular & Cellular Proteomics. 2002. 1: 304-313 (Year: 2002).*
Peng et al. Nature Communications. Feb. 2014. 5(3361, p. 1-11 (Year: 2014).*
Vogel et al. Nature Review Genet. Mar. 2012. 13(4): 227-232 (Year: 2912).*
Ascierto et al., "The intratumoral balance between metabolic and immunologic gene expression is associated with anti-PD-1 response in patients with renal cell carcinoma," *Cancer Immunol. Res.*, 4:726-733, 2016.
Cardoso et al., "70-gene signature as an aid to treatment decisions in early-stage breast cancer," *N. Engl. J. Med.*, 375:717-729, 2016.
Cowin et al., "Profiling the cancer genome," *Annu. Rev. Genomics Hum. Genet.*, 11:133-159, 2010.
Creighton et al., "Residual breast cancers after conventional therapy display mesenchymal as well as tumor-initiating features," *Proc. Natl. Acad. Sci. U. S. A.*, 106:13820-13825, 2009.
Ercilla et al., "New origin firing is inhibited by APC/C$^{Cdh1}$ activation in S-phase after severe replication stress," *Nucleic Acids Res.*, 44:4745-4762, 2016.
Ginestier et al., "ALDH1 is a marker of normal and malignant human mammary stem cells and a predictor of poor clinical outcome," *Cell Stem Cell*, 1:555-567, 2007.
Lin et al., "The replication stress response defect is associated with tumor-initiating cell formation," In: Proceedings of the 105$^{th}$ Annual Meeting of the American Association for Cancer Research, *Cancer Res*, 74(19 Suppl):Abstract 354, 2014.
McGrail et al., "Defective replication stress response is inherently linked to the cancer stem cell phenotype," *Cell Reports*, 23:2095-2106, 2018.
McGrail et al., "Improved prediction of PARP inhibitor response and identification of synergizing agents through use of a novel gene expression signature generation algorithm," *Npj Syst. Biol. Appl.*, 3:8, 2017.
Miao et al., "Genomic correlates of response to immune checkpoint therapies in clear cell renal cell carcinoma," *Science*, 359(6377):801-806, 2018.

(Continued)

*Primary Examiner* — Carla J Myers
(74) *Attorney, Agent, or Firm* — Parker Highlander PLLC

(57) ABSTRACT

Methods for increasing immune therapy response and predicting likelihood of cancer metastasis by analyzing the expression of genes associated with replication stress response. In some aspects, cancers are treated with immune checkpoint inhibitors and/or MEK inhibitors. Methods for selecting patients by analyzing the expression of genes associated with a defect in replication stress response are also provided.

17 Claims, 37 Drawing Sheets

(56) References Cited

OTHER PUBLICATIONS

PCT International Search Report and Written Opinion issued in International Application No. PCT/US2019/020921, dated Jul. 10, 2019.
Pilie et al., "Replication stress response deficiency (RSRD) and response to immune therapy in clear cell renal cell carcinoma (ccRCC)," *Journal of Clinical Oncology*, 36(15 Suppl.):4566, 2018.
Pitroda et al., "DNA Repair Pathway Gene Expression Score Correlates with Repair Proficiency and Tumor Sensitivity to Chemotherapy," *Sci. Transl. Med.*, 6:229ra42, 2014.
Poola et al., "Identification of MMP-1 as a putative breast cancer predictive marker by global gene expression analysis," *Nat. Med.*, 11:481-483, 2005.
Snyder et al., "Contribution of systemic and somatic factors to clinical response and resistance to PD-L1 blockade in urothelial cancer: an exploratory multi-omic analysis," *PLoS Med.*, 14:e1002309, 2017.
Wallden et al., "Development and verification of the PAM50-based Prosigna breast cancer gene signature assay," *BMC Med. Genomics*, 8:54, 2015.
Zhou et al., "Tumour-initiating cells: challenges and opportunities for anticancer drug discovery," *Nat. Rev. Drug Discov.*, 8:806-823, 2009.

\* cited by examiner

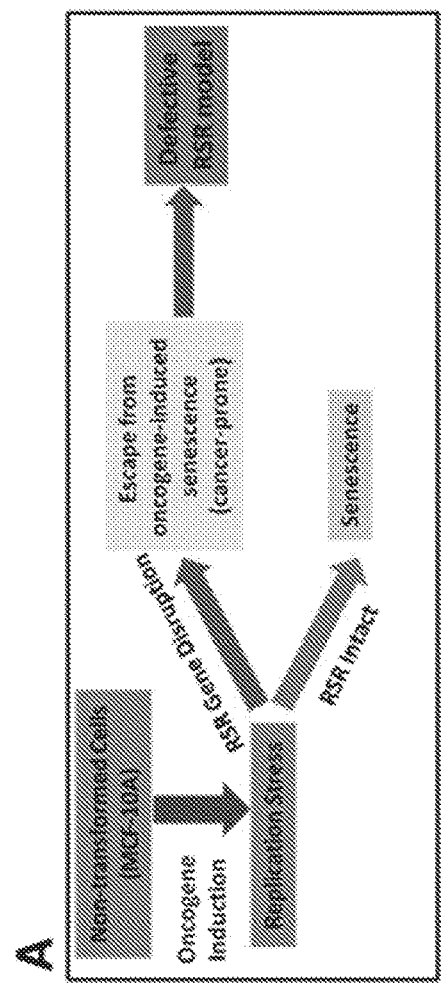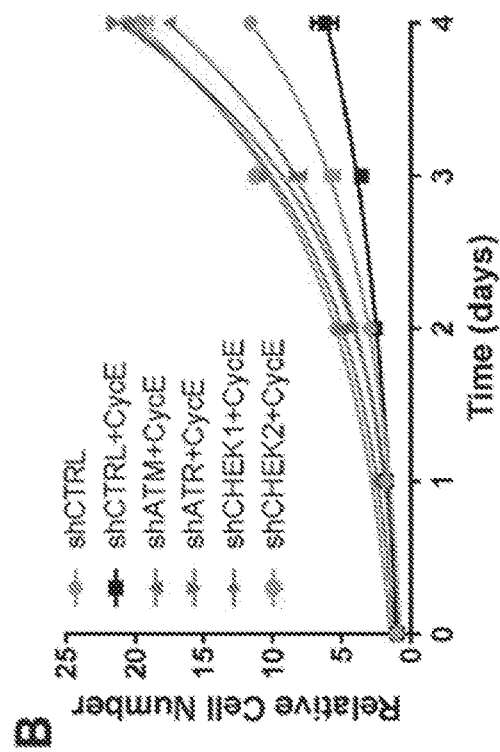
FIGS. 1A-B

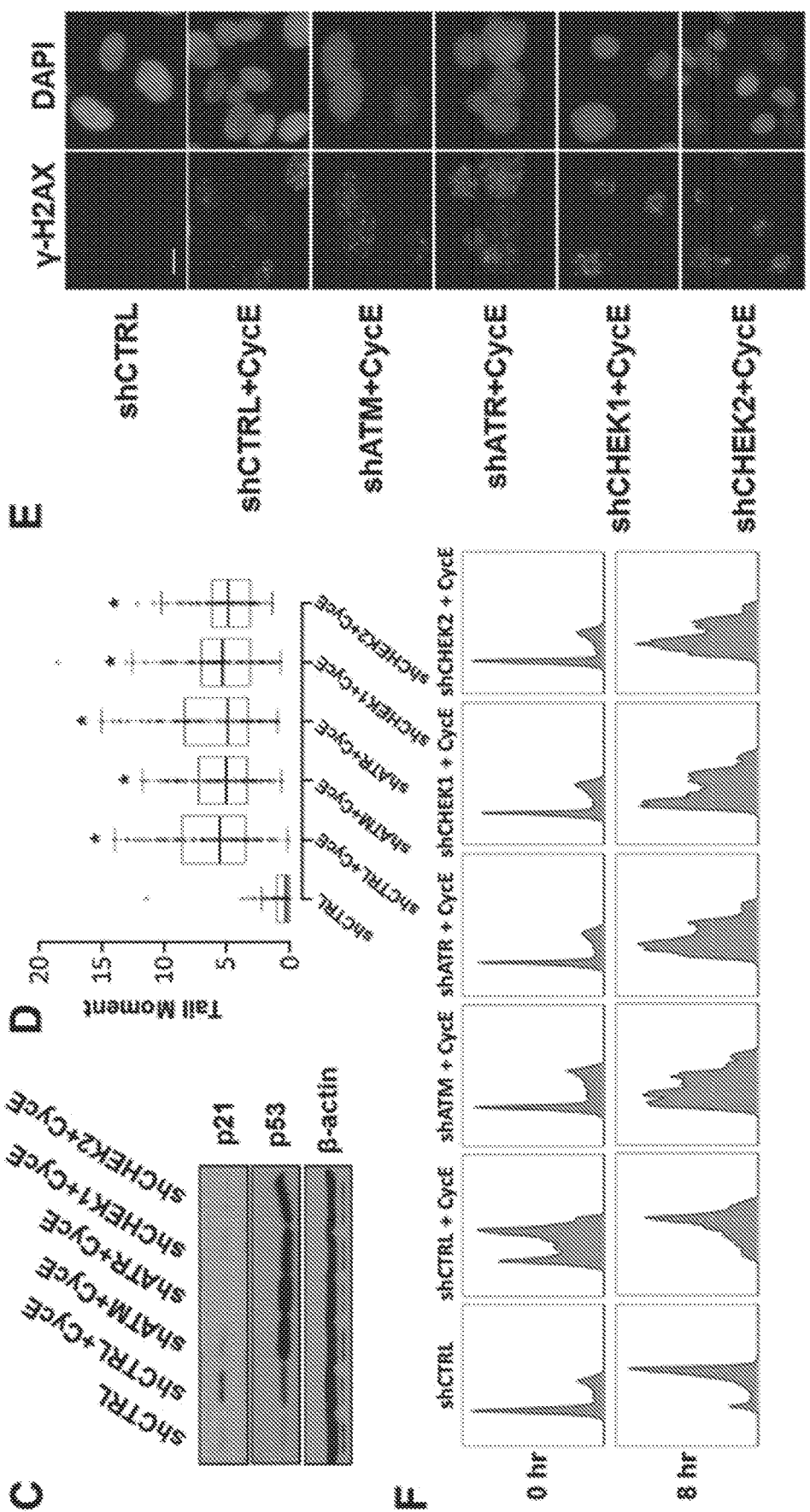
FIGS. 1C-E

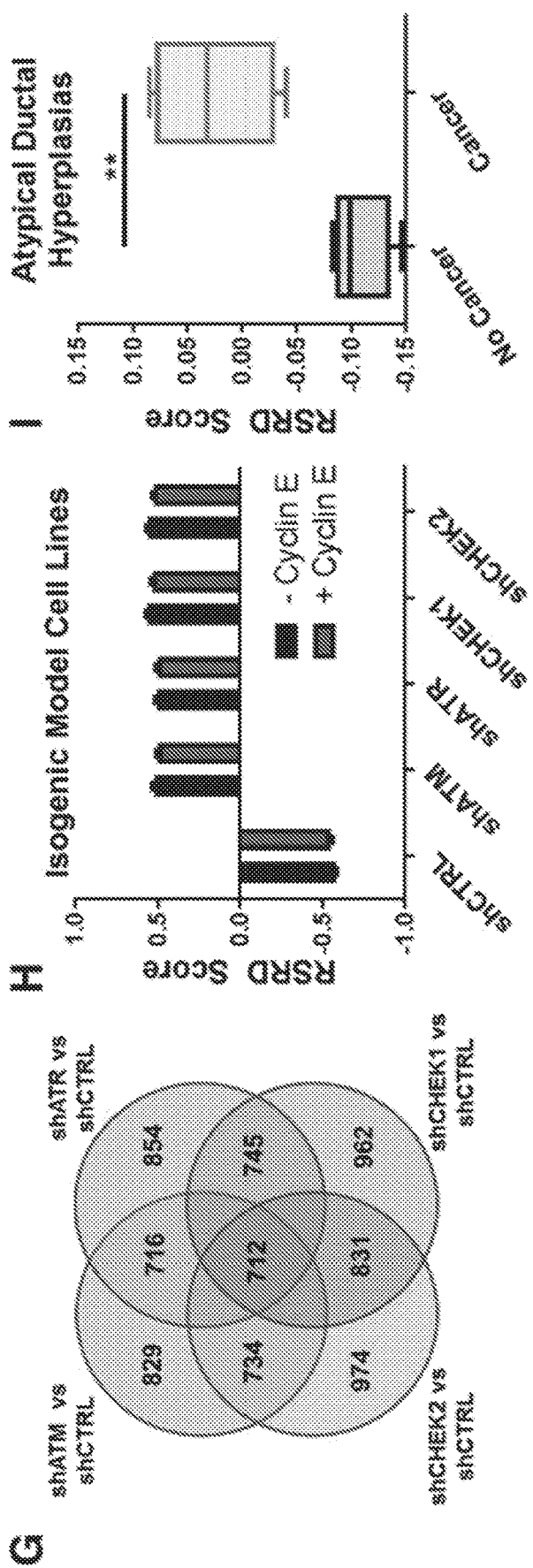
FIGS. 1F-H

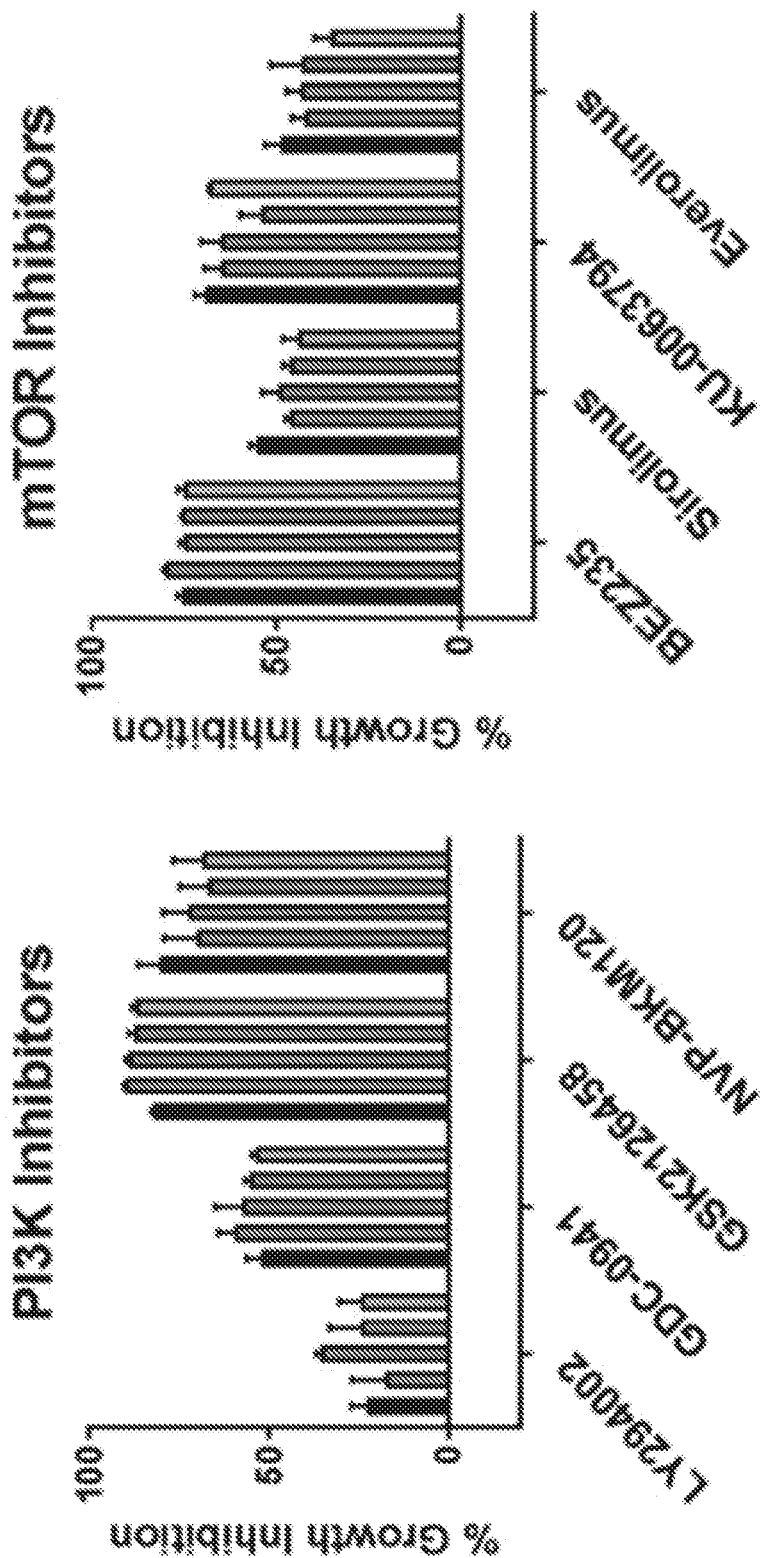
FIG. 4B, cont.

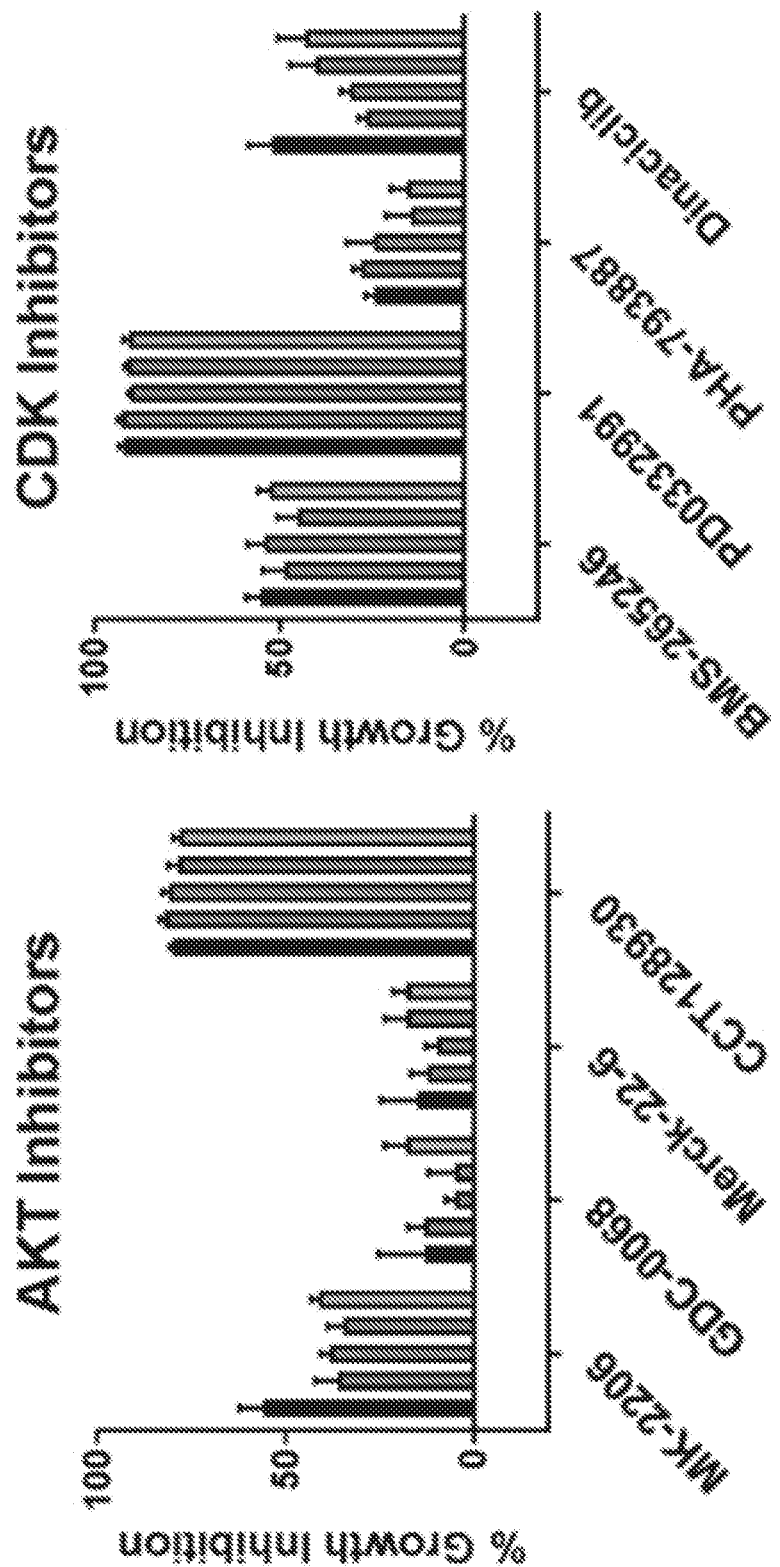
FIG. 4B, cont.

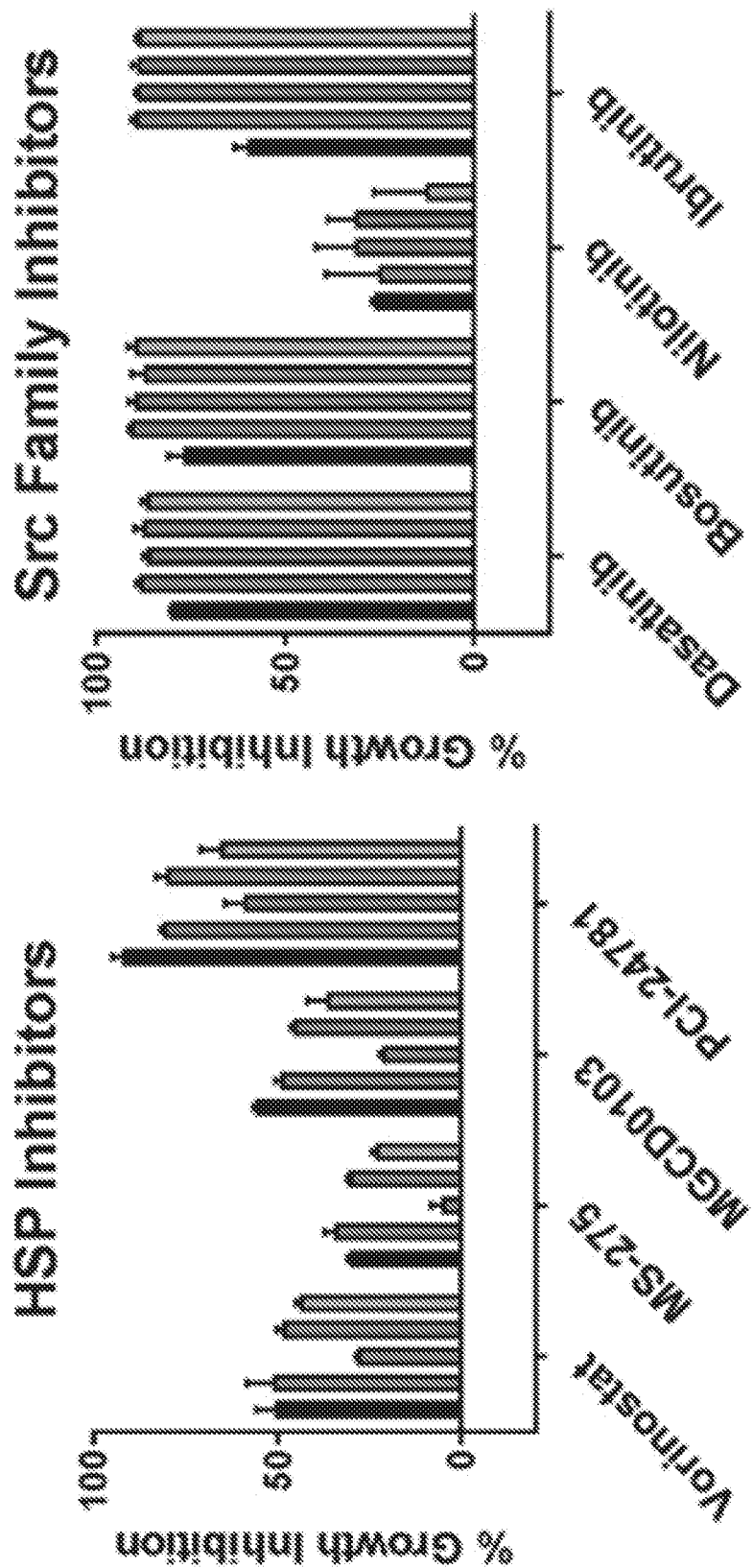
FIG. 4B, cont.

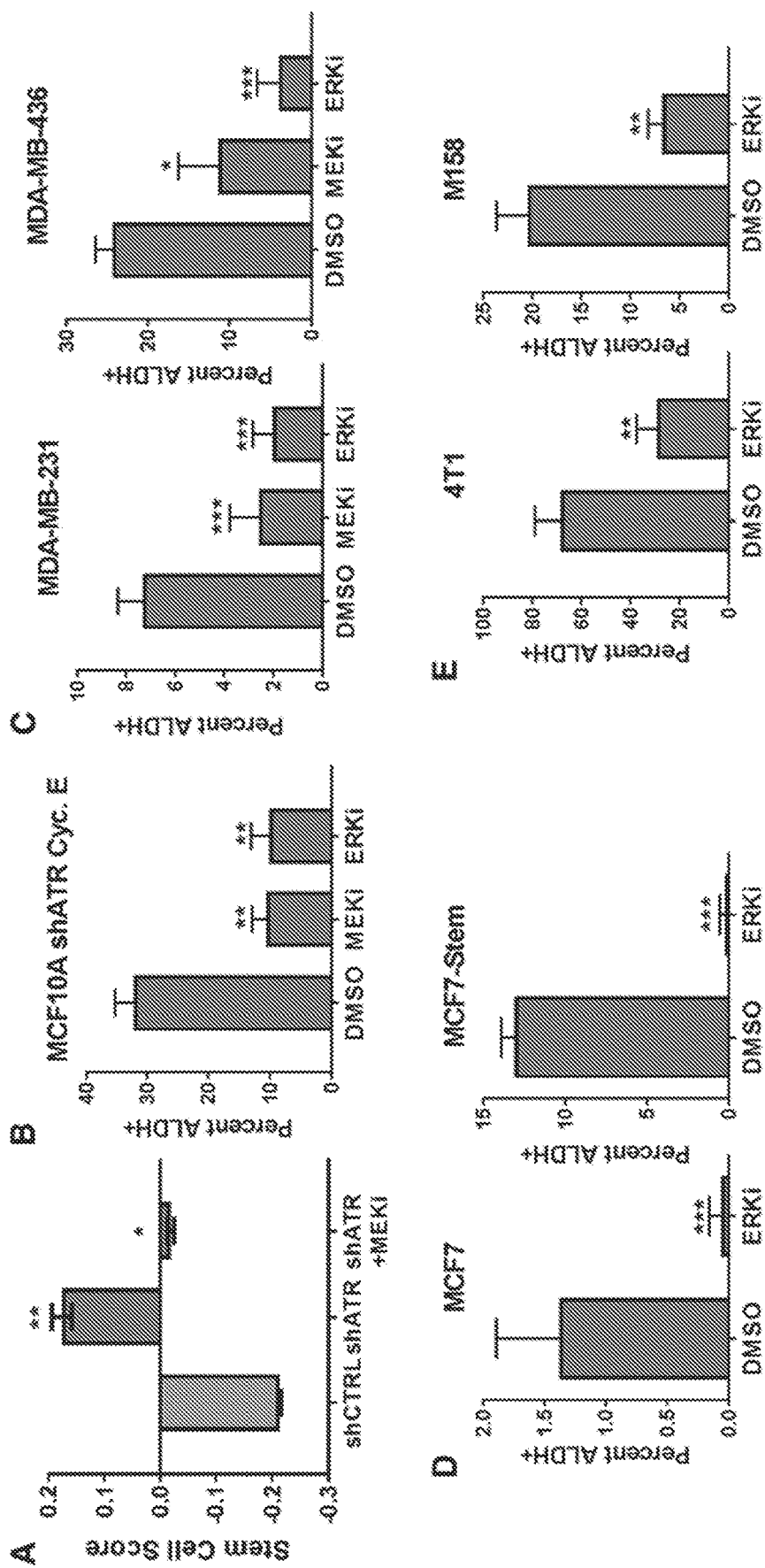
FIGS. 5A-E

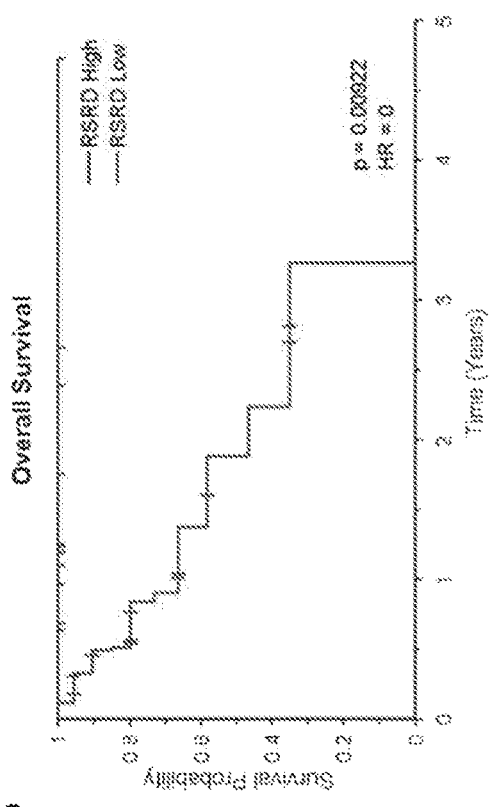
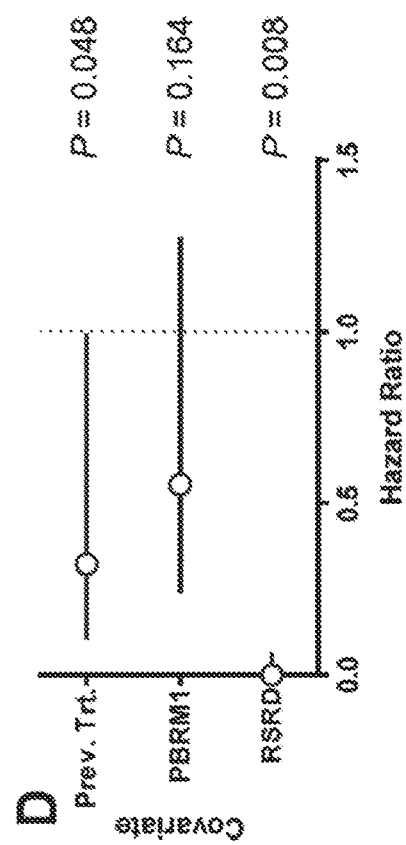
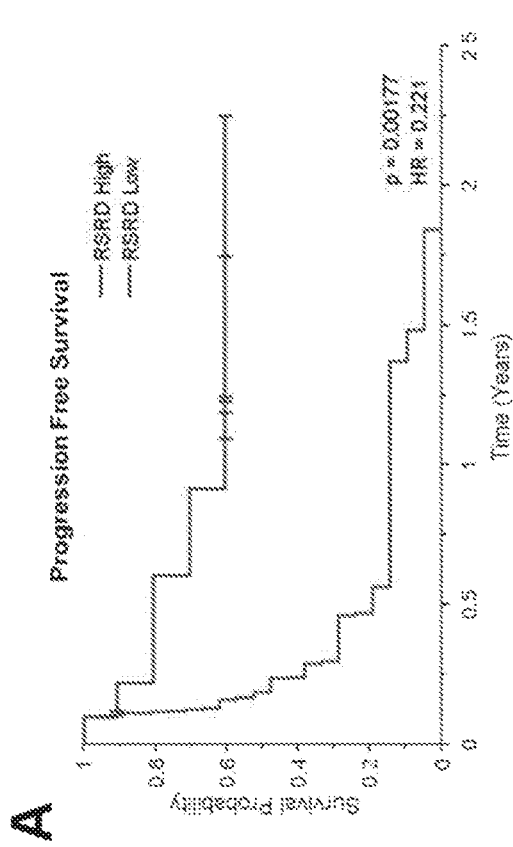
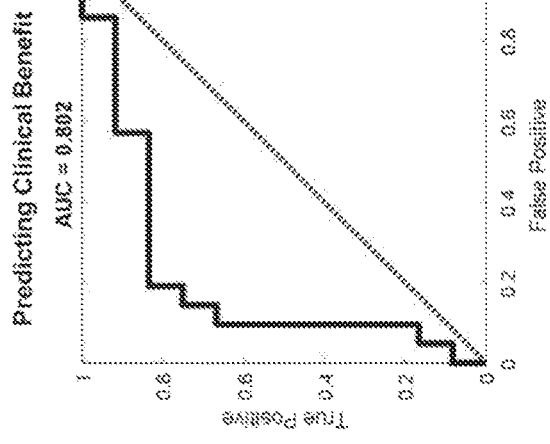
FIGS. 7A-D

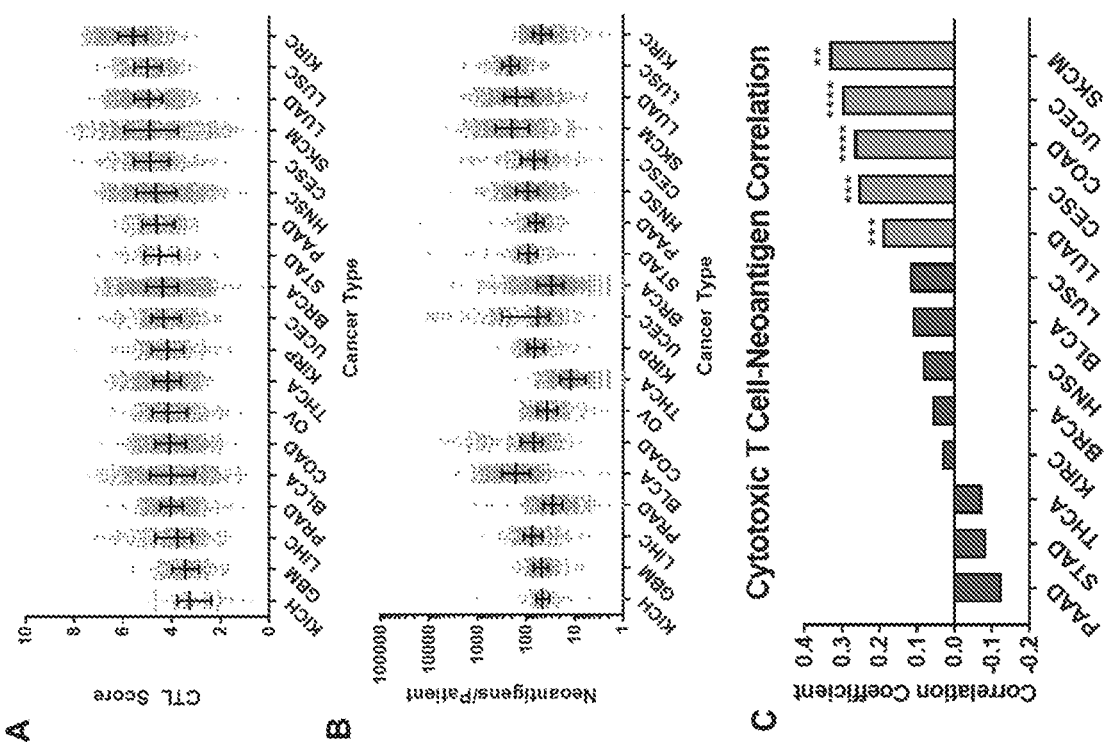
FIGS. 8A-C

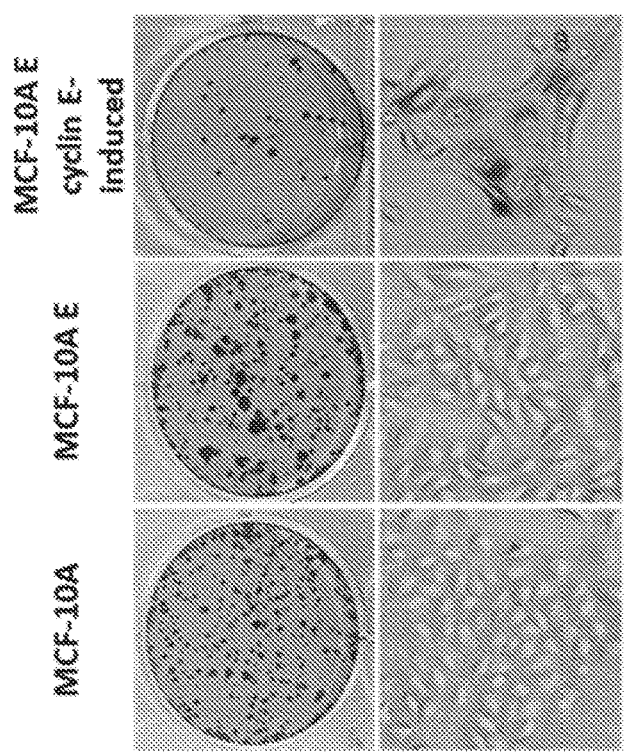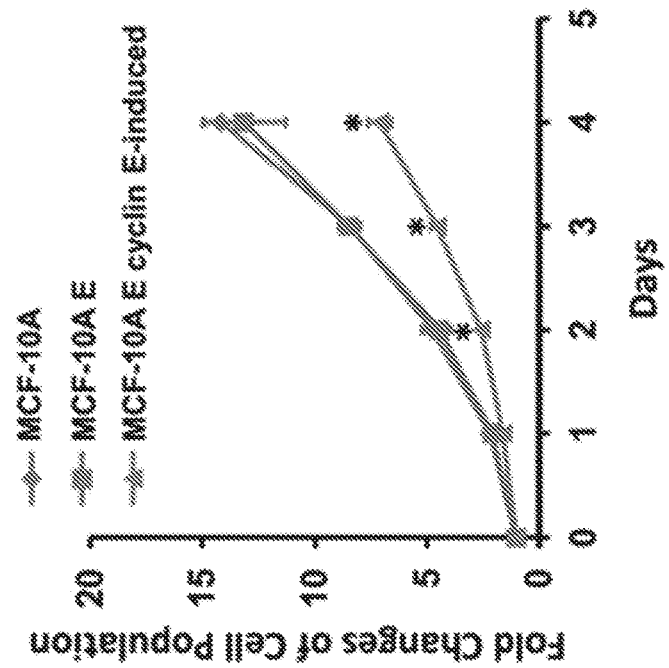
FIGS. 9A-B

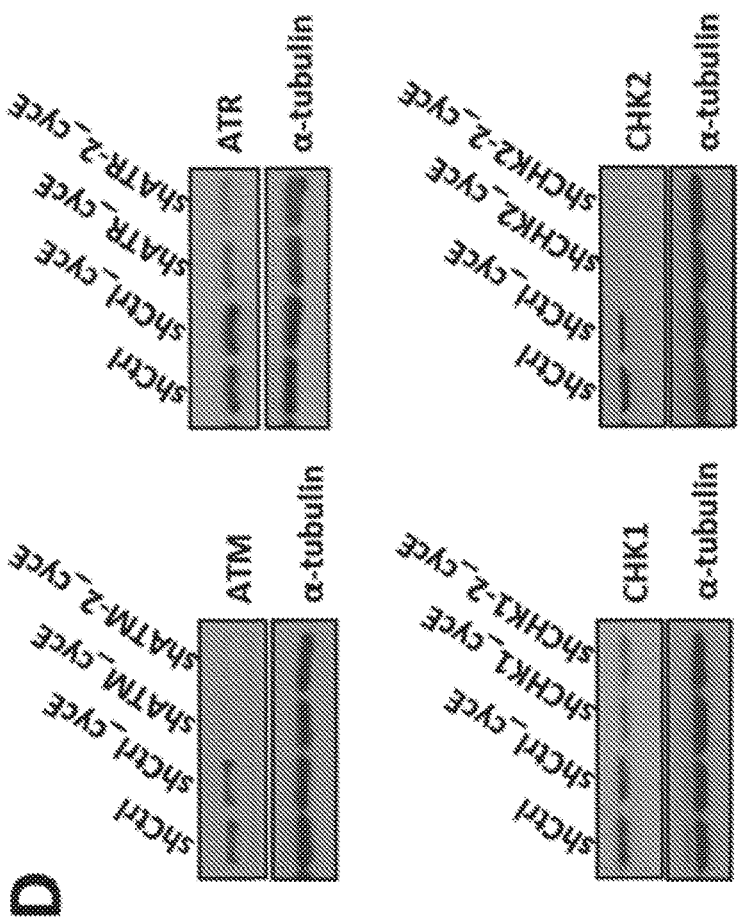
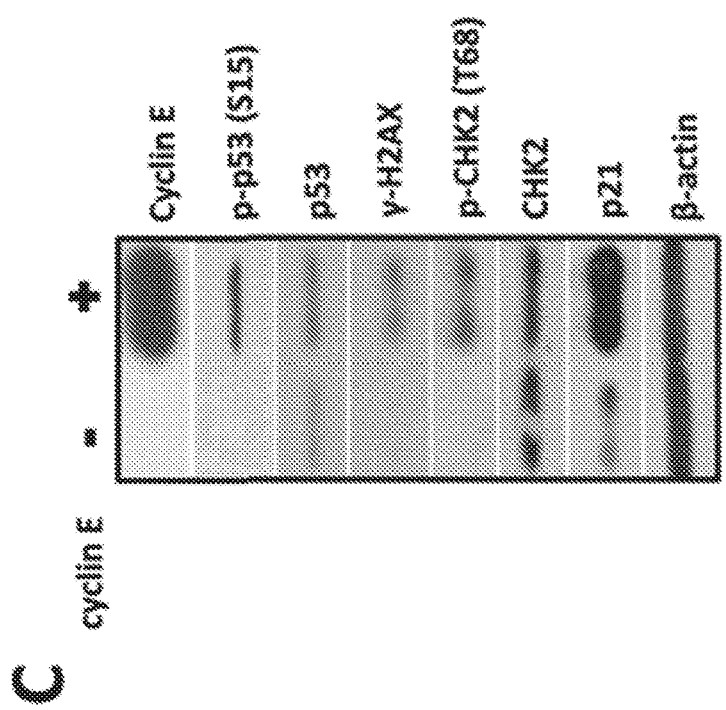
FIGS. 9C-D

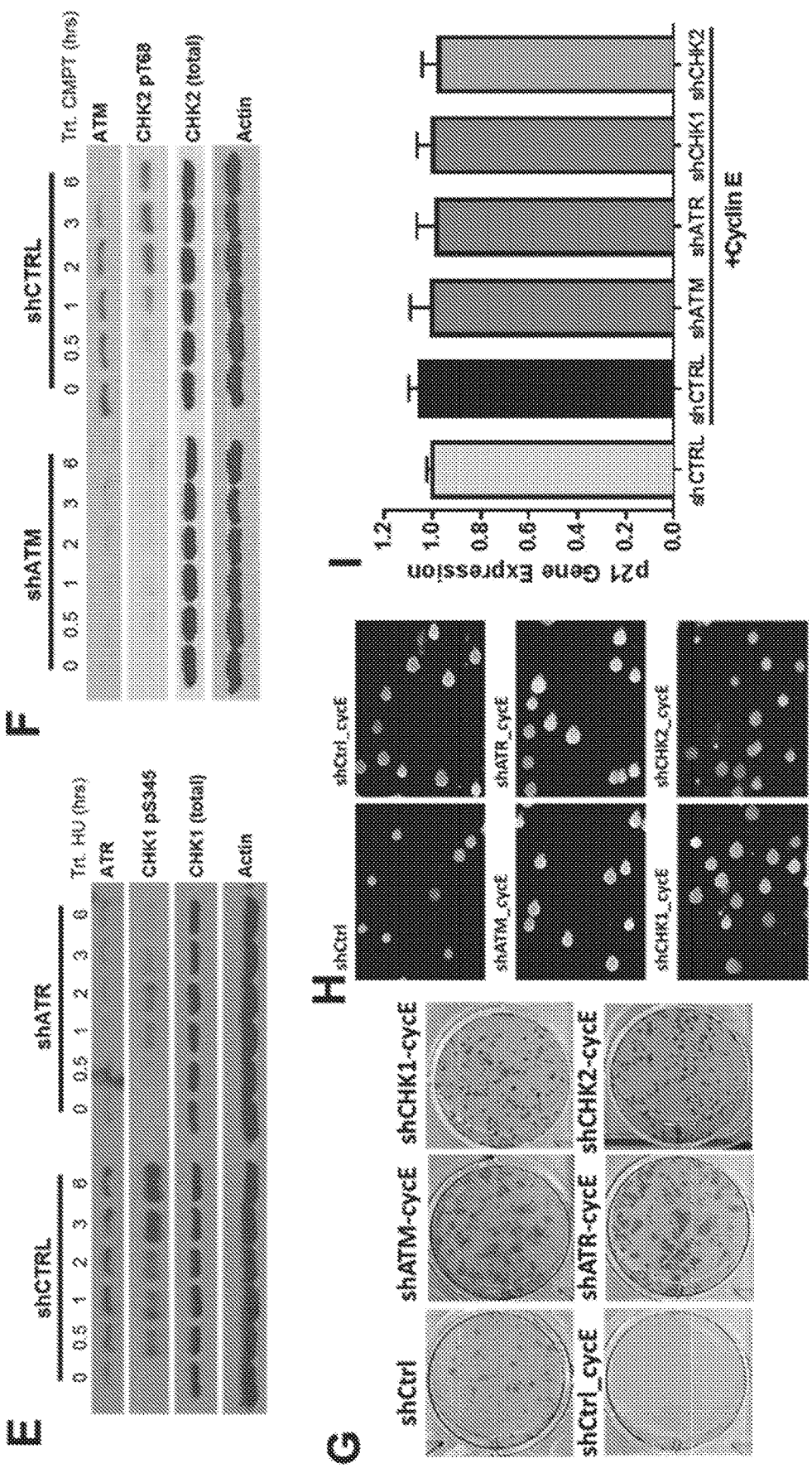
FIGS. 9E-I

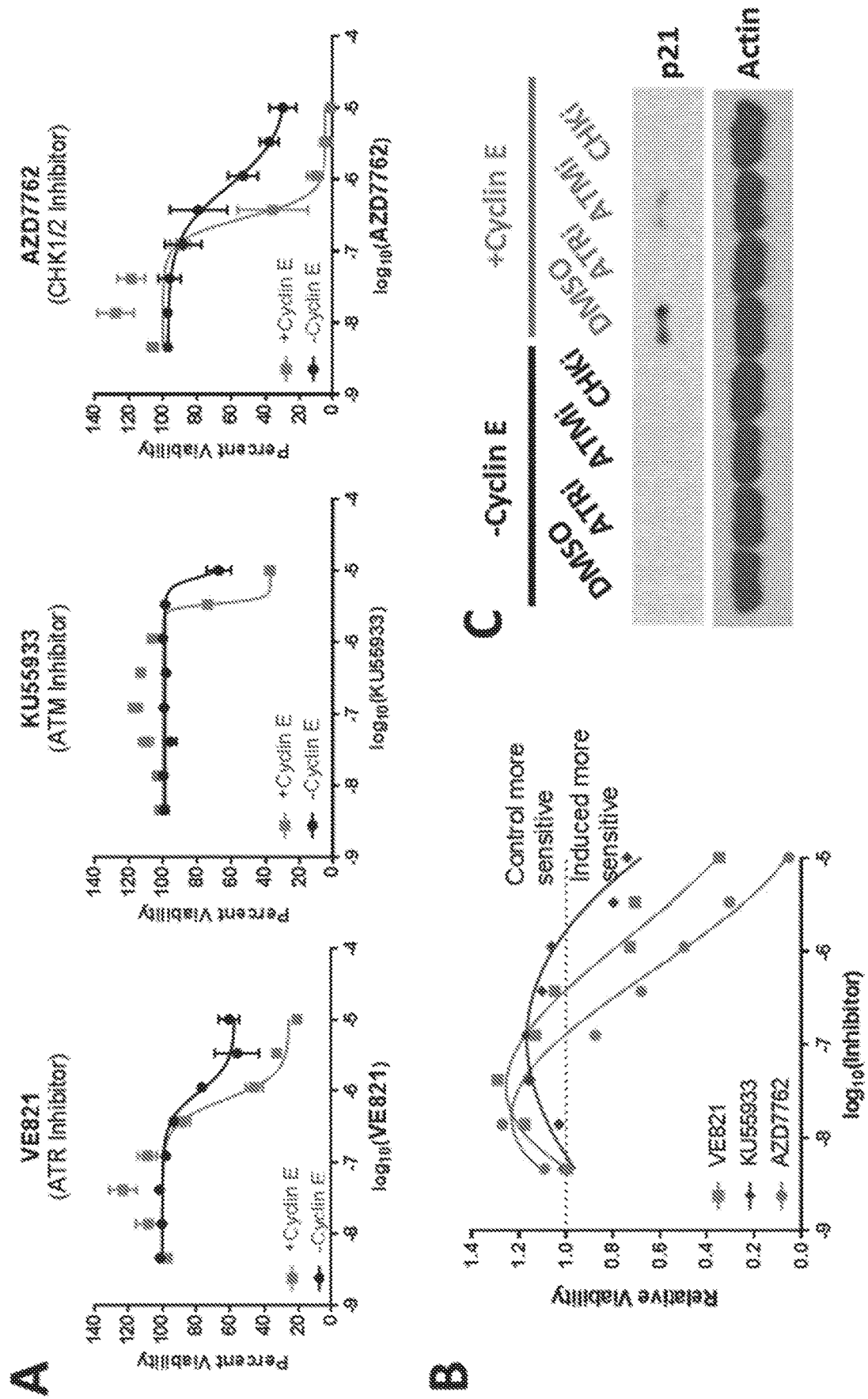
FIGS. 10A-C

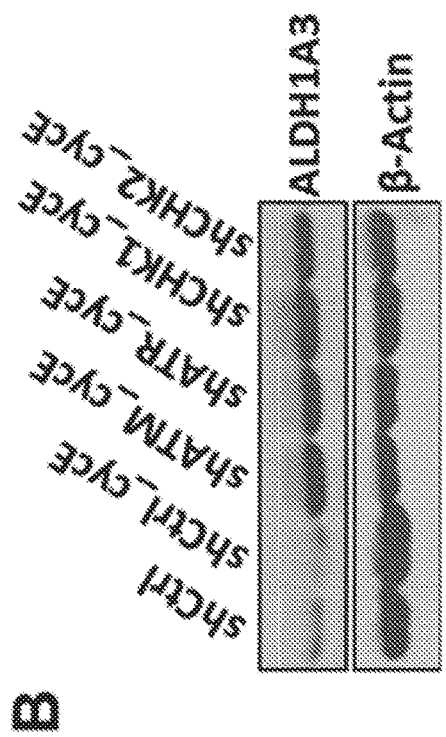
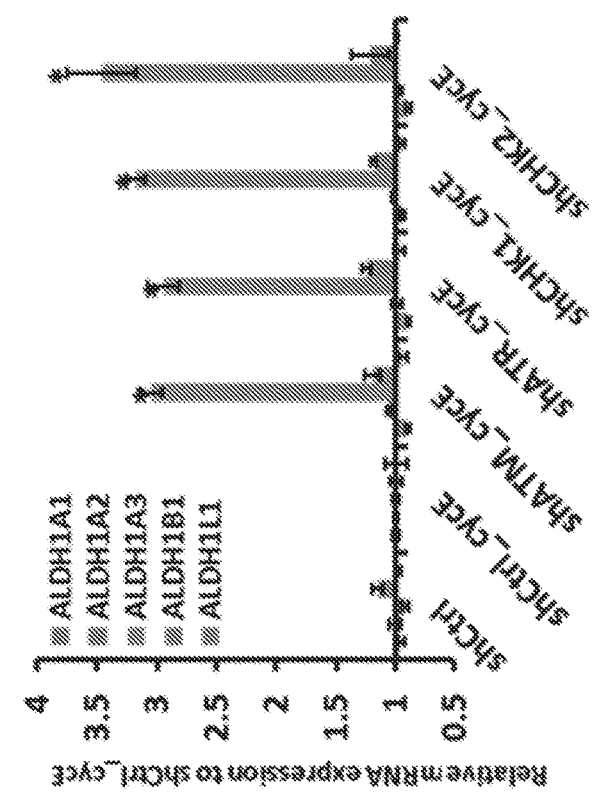
FIGS. 11A-B

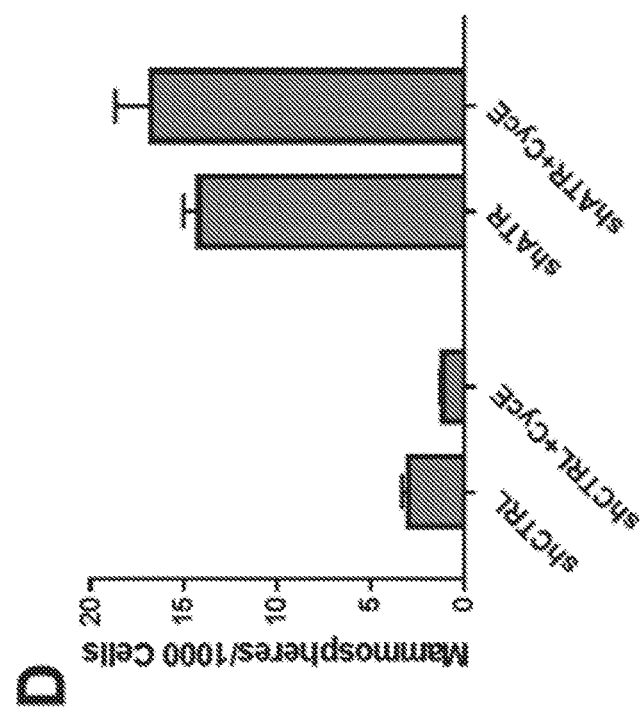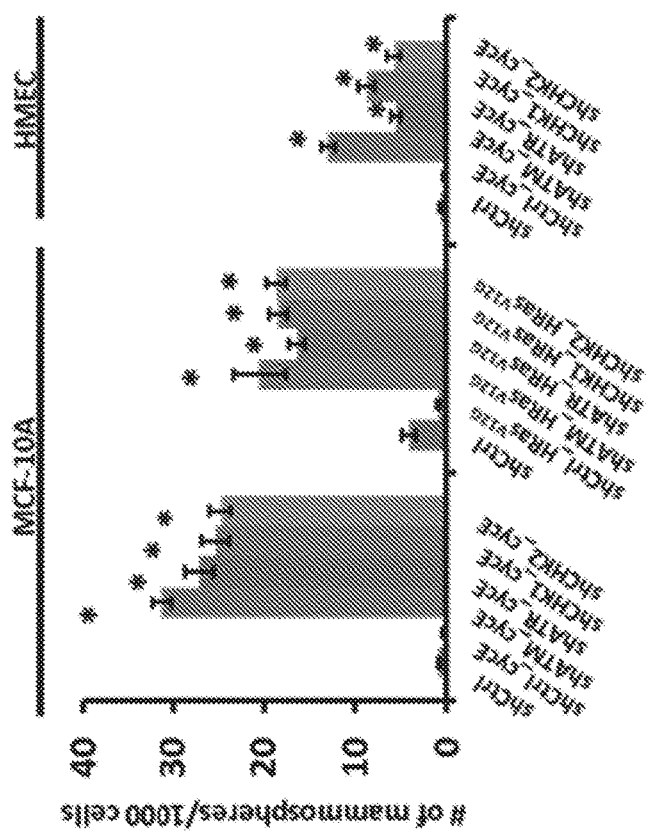
FIGS. 11C-D

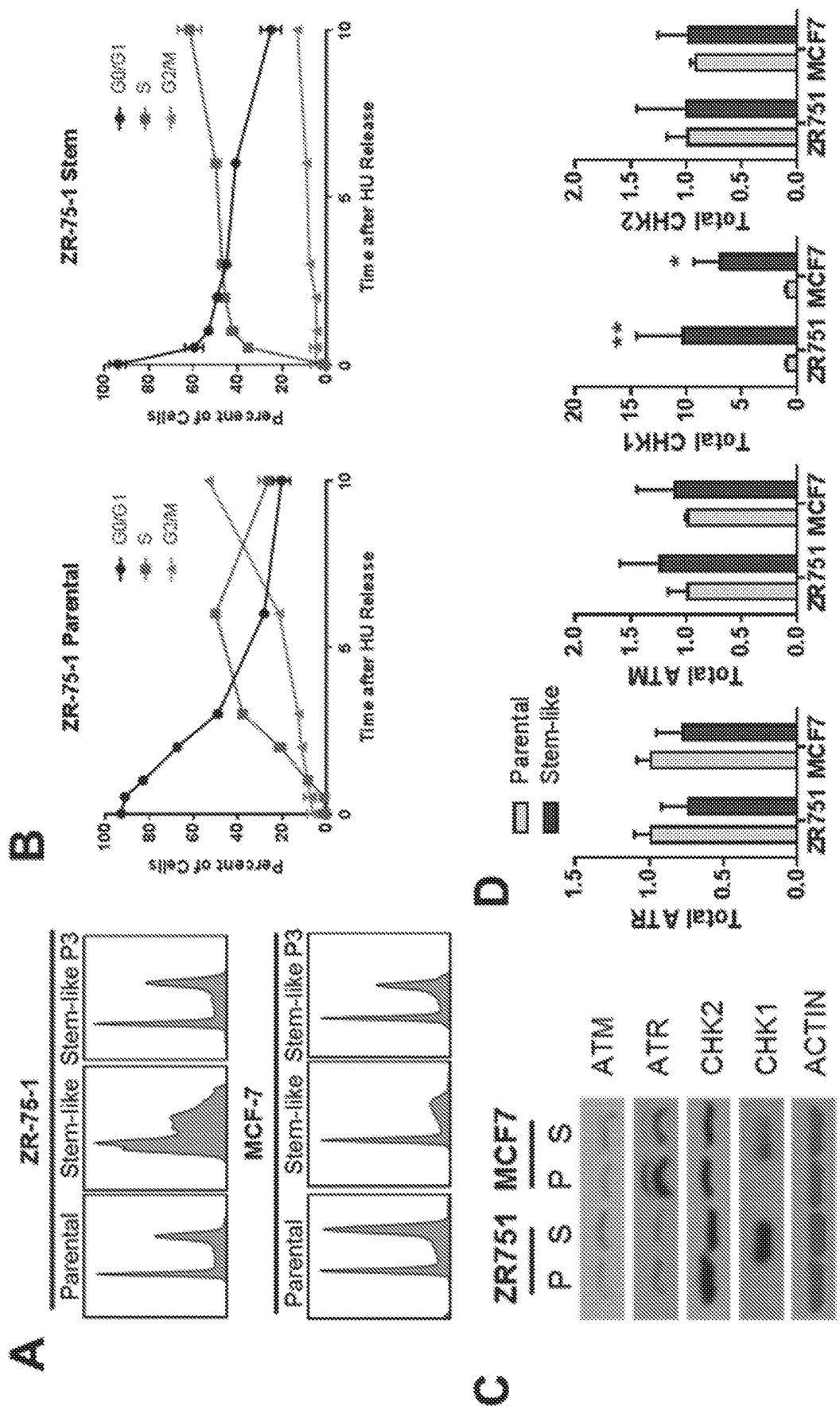
FIGS. 12A-D

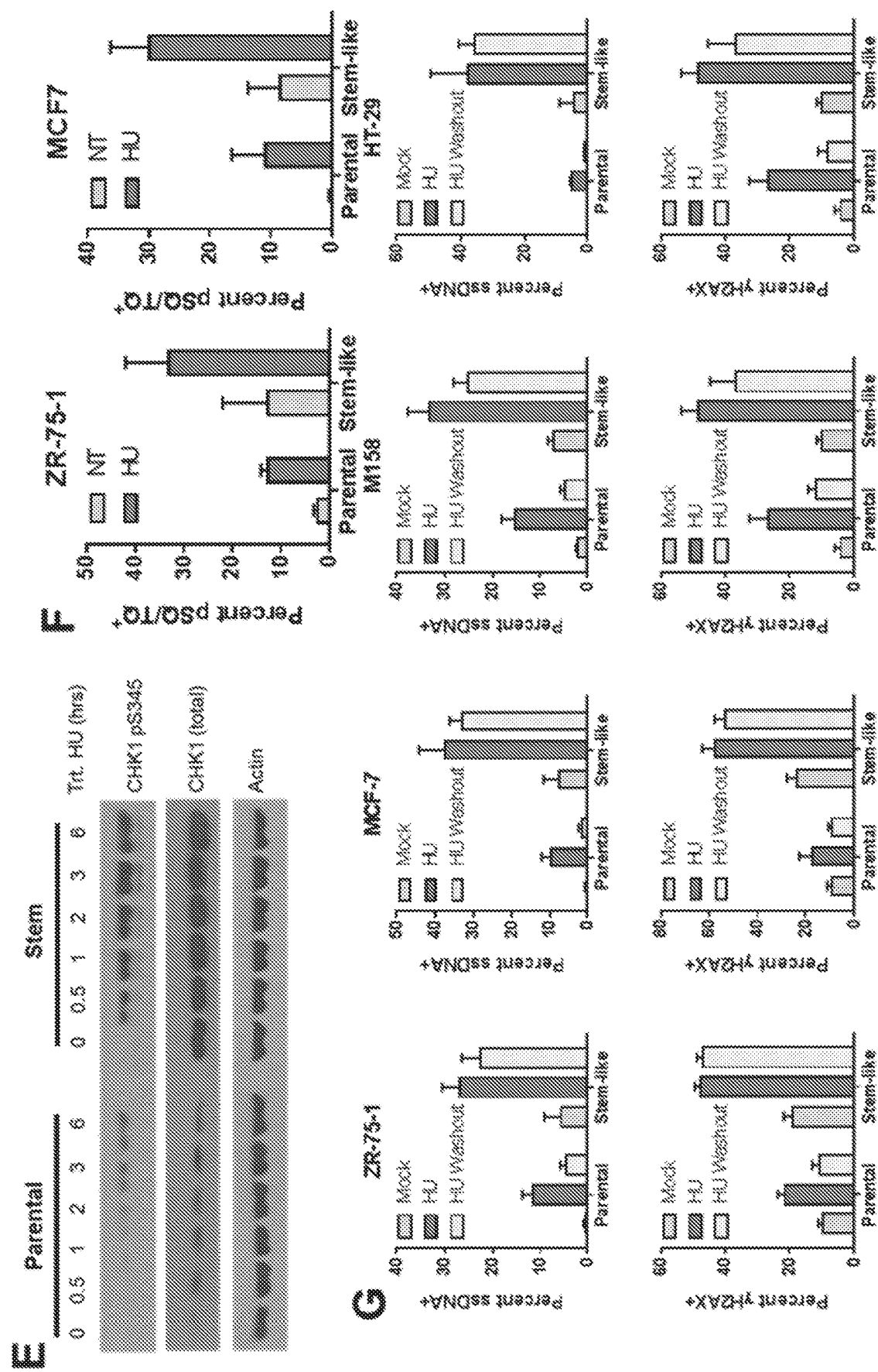
FIGS. 12E-G

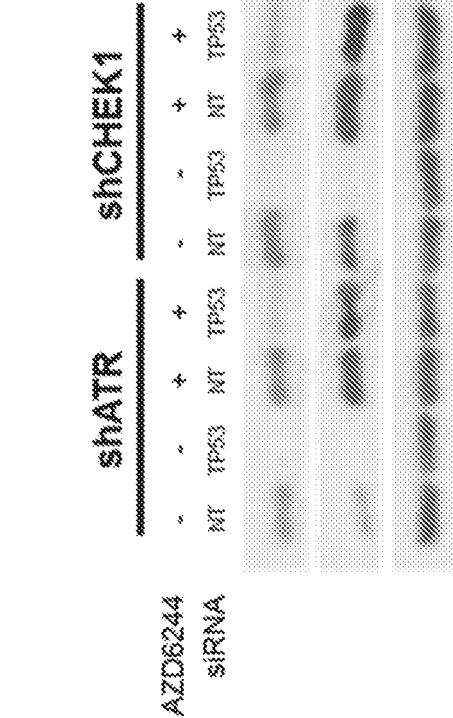
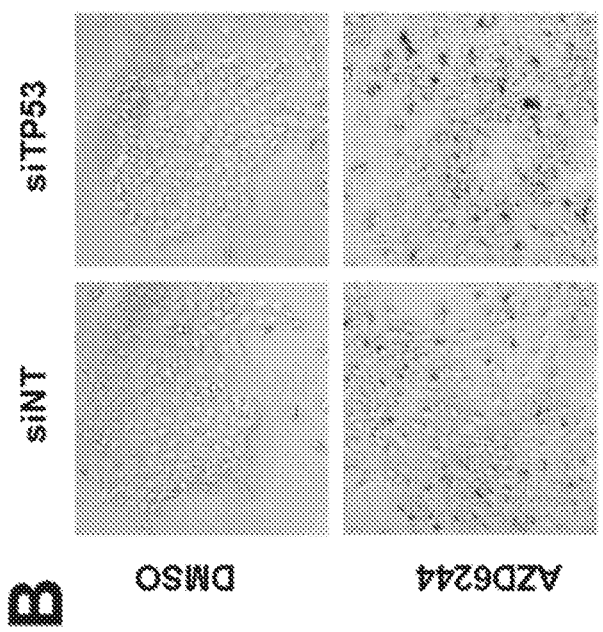
FIGS. 13A-B
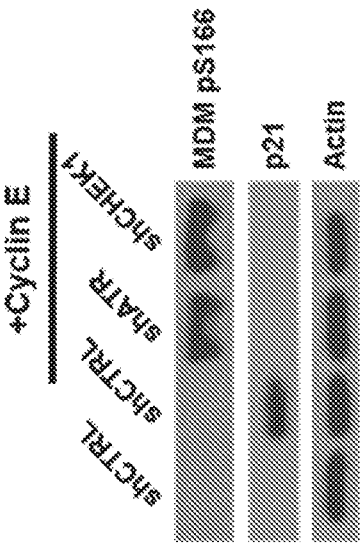
FIG. 13C

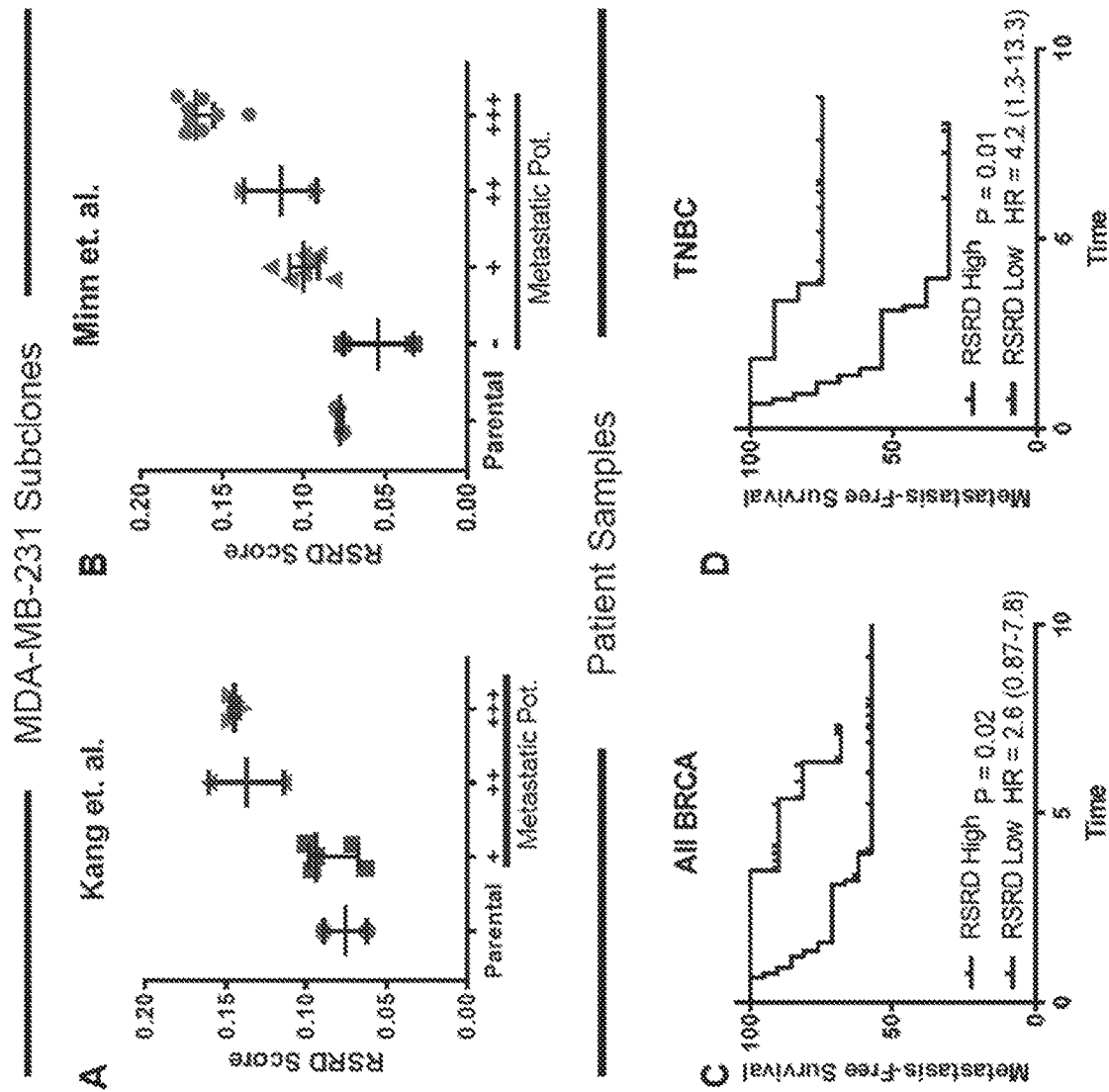
FIGS. 14A-D

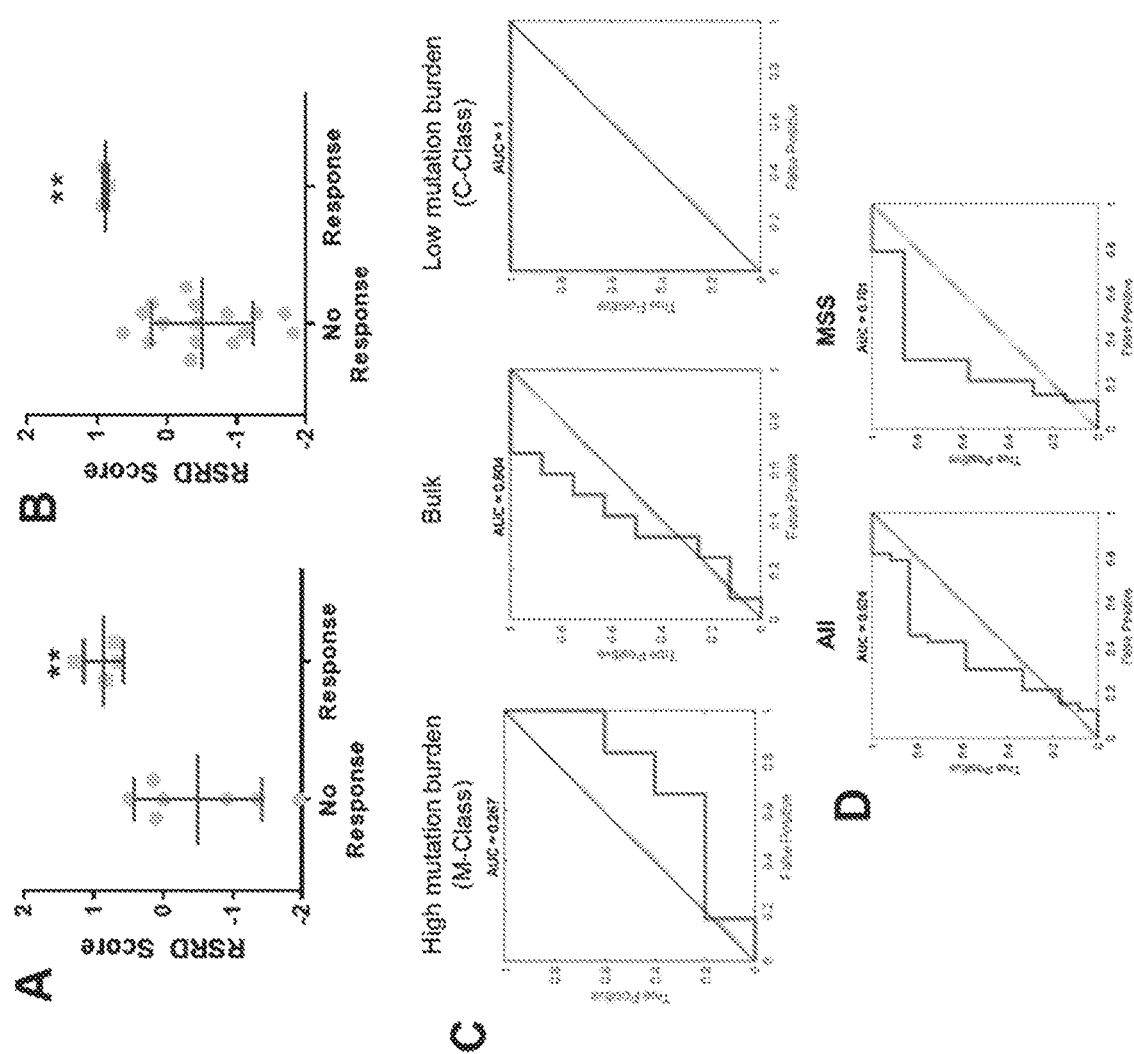
FIGS. 15A-D

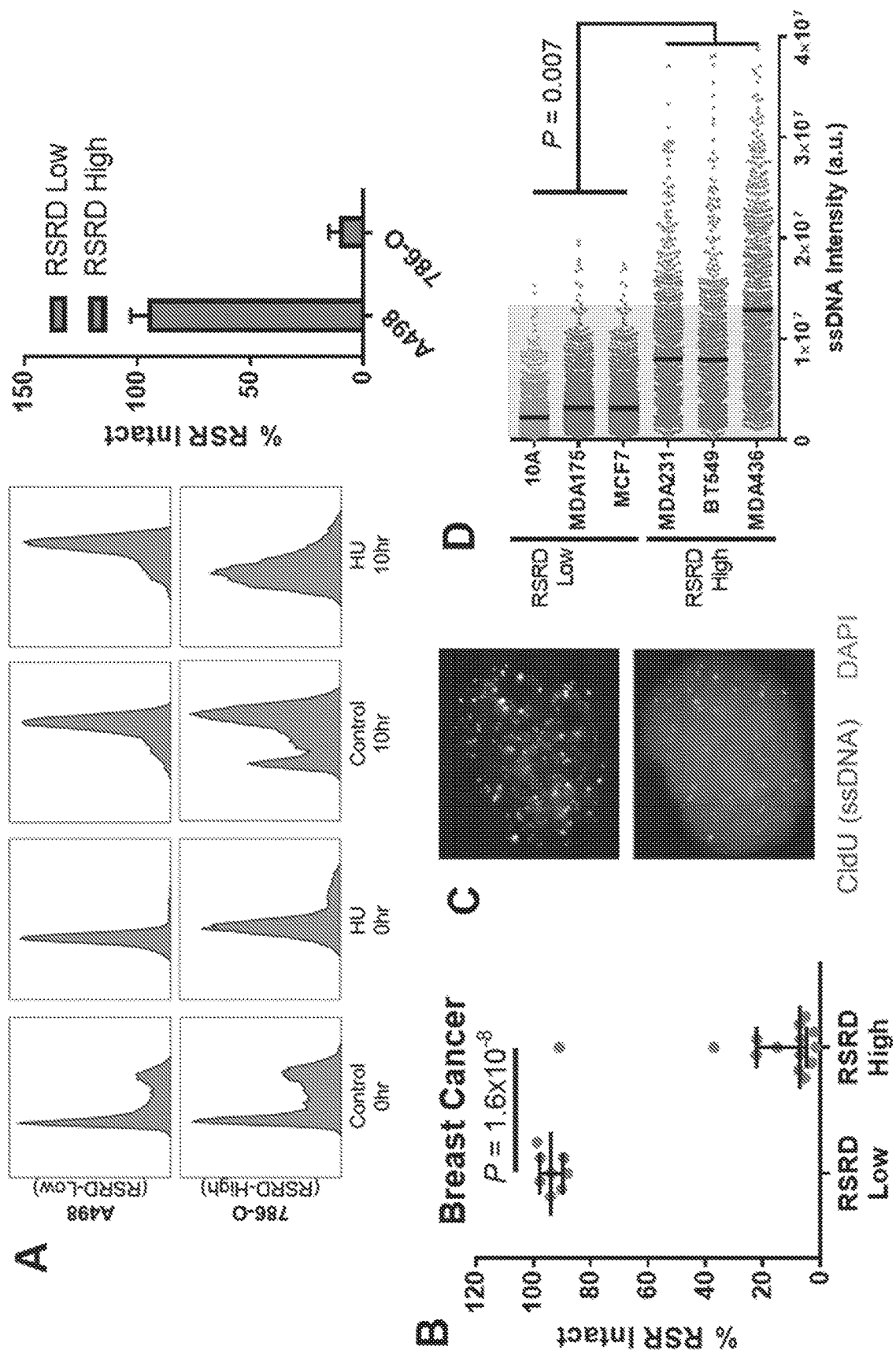
FIGS. 16A-D

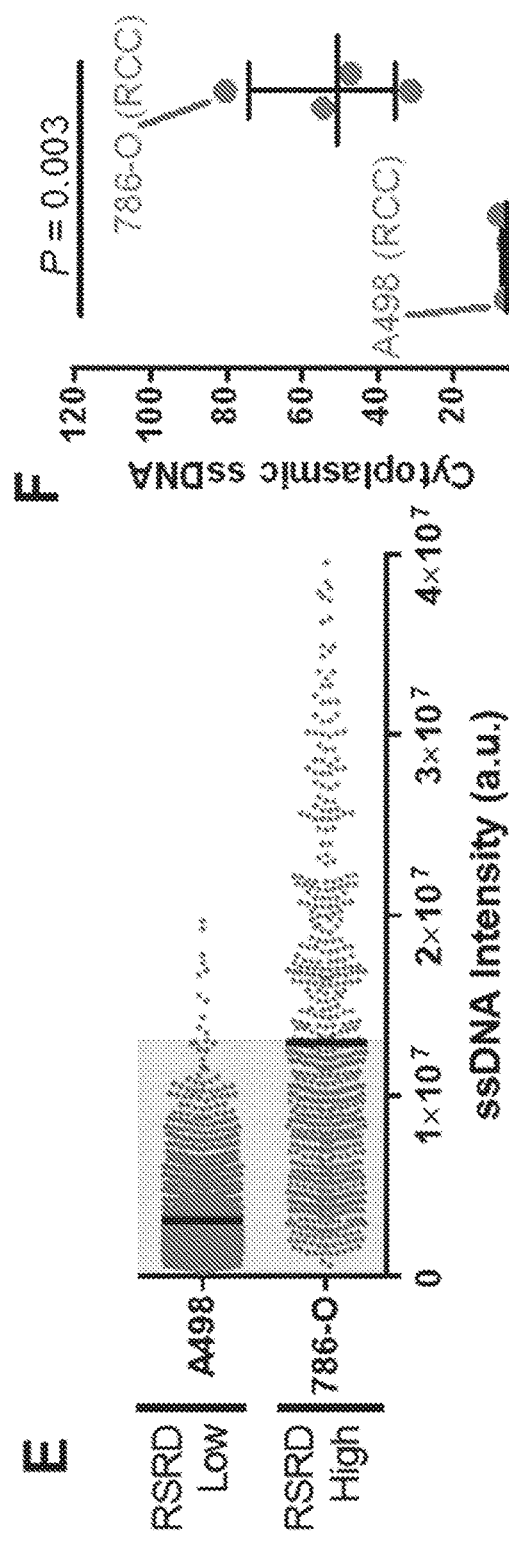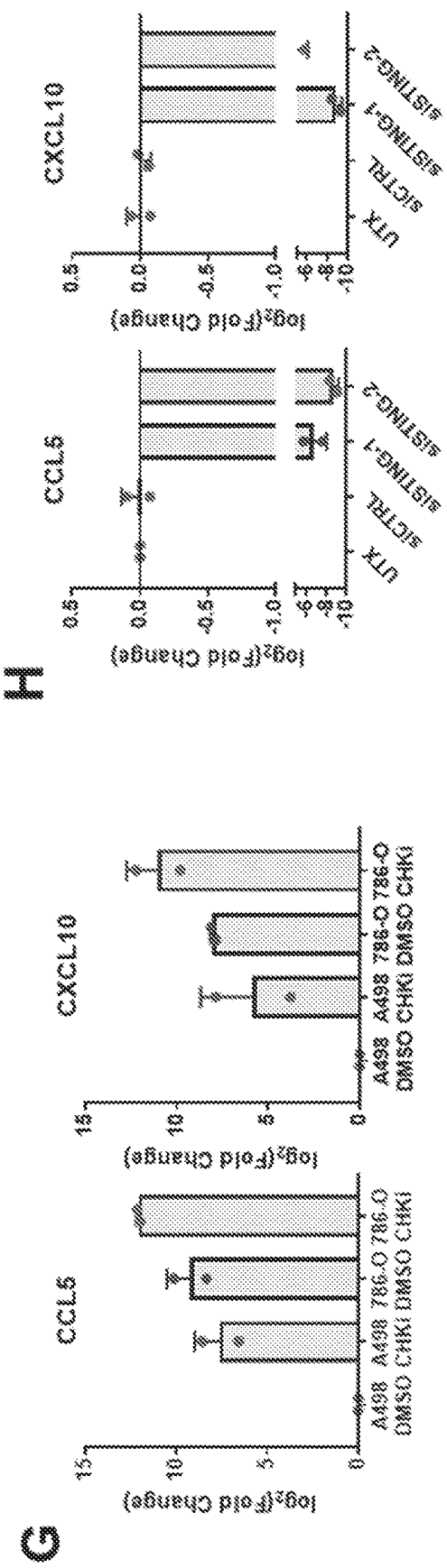
FIGS. 16E-H

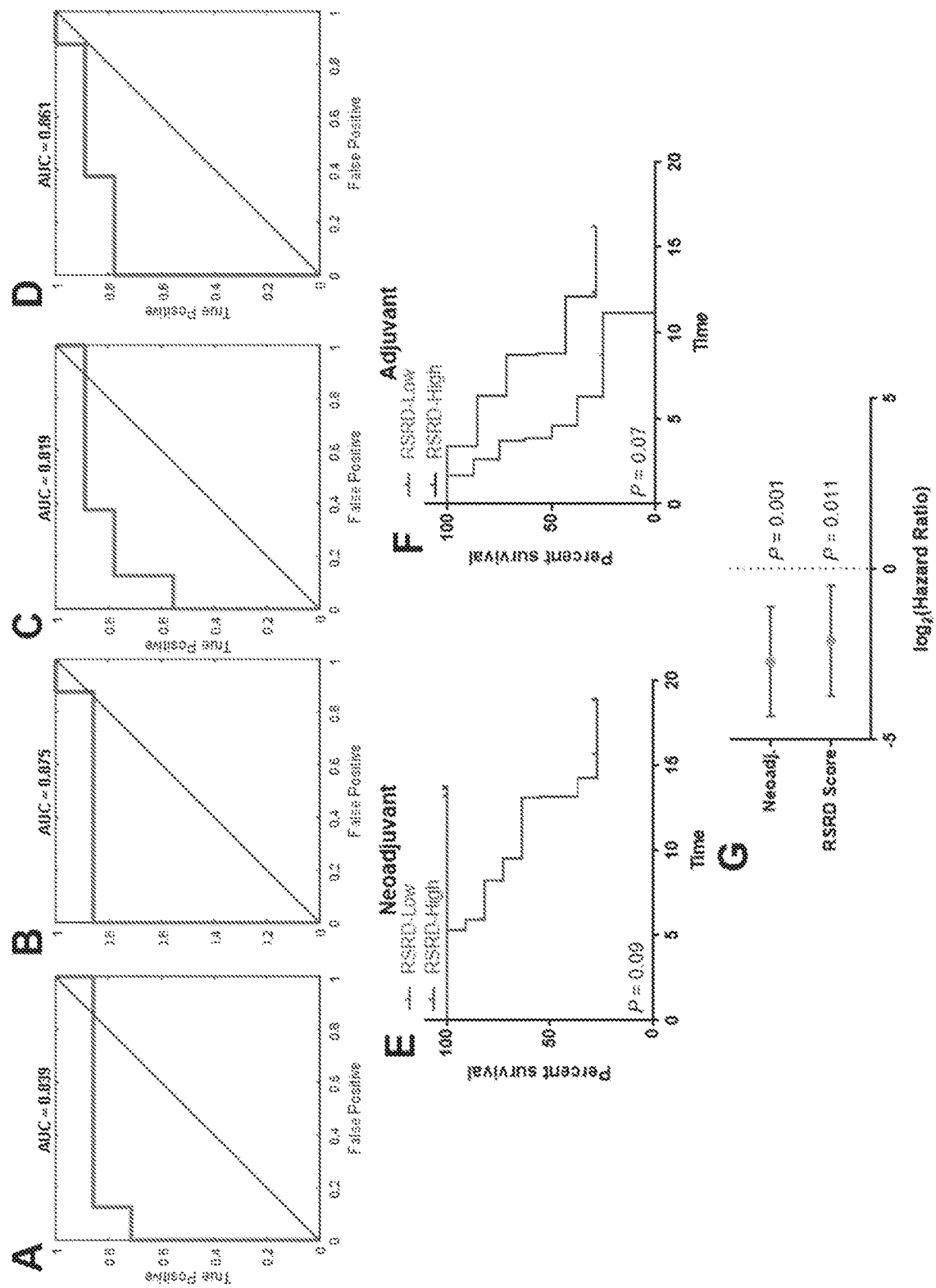
FIGS. 17A-G

REPLICATION STRESS RESPONSE BIOMARKERS FOR IMMUNOTHERAPY RESPONSE

REFERENCE TO RELATED APPLICATIONS

The present application is a national phase application under 35 U.S.C. § 371 of International Application No. PCT/US2019/020921, filed Mar. 6, 2019, which claims the priority benefit of U.S. provisional application Nos. 62/639,439, filed Mar. 6, 2018, and 62/661,383, filed Apr. 23, 2018, the entire contents of each of which is incorporated herein by reference.

STATEMENT REGARDING FEDERALLY SPONSORED RESEARCH

This invention was made with government support under Grant Number W81XWH-10-1-0558 awarded by the U.S. Department of the Army. The Government has certain rights in the invention.

BACKGROUND

1. Field

The present disclosure relates generally to the field of molecular biology and oncology. More particularly, it concerns methods for identifying immune checkpoint inhibitor-sensitive cancers and methods for enhancing immune checkpoint inhibitor treatment.

2. Description of Related Art

Oncogene activation induces hyperproliferation, which consequently triggers replication stress and excessive spontaneous DNA damage. This process causes genomic instability and is a key feature of cancer at its earliest stages (Gorgoulis et al., 2005). Replication stress induces the S-phase checkpoint, or replication stress response (RSR), to ensure DNA replication fidelity and to maintain genome integrity (Berti and Vindigni, 2016). This response is primarily coordinated by two signaling cascades: the ataxia telangiectasia mutated (ATM)-checkpoint kinase 2 (CHK2) pathway and the ataxia telangiectasia and Rad3-related (ATR)-checkpoint kinase 1 (CHK1) pathway. When DNA replication stress and double-strand breaks are excessive, RSR acts as a tumor suppressor mechanism by inducing cell differentiation (Gandarillas, 2012; Wang et al., 2012), apoptosis (Lowe et al., 2004), or oncogene-induced senescence (OIS) (Di Micco et al., 2006). Defects in the replication stress response enable cells to evade OIS and continue proliferating, ultimately leading to early tumorigenesis (Bartkova et al., 2006). However, the phenotypic changes associated with RSR defects and the mechanisms cells use to survive such large levels of replication stress remain unknown, as well as how these defects affect treatment and prognosis.

Personalized treatment and management of cancer relies on the genotypic and phenotypic understanding of various cancer types, and of their subtypes. Pre-clinical pharmaceutical testing in cancer cell line panels has been used to guide early-stage clinical trials, often using single gene assays. Unfortunately, for the majority of therapeutic molecules, a single gene assay is insufficient to accurately predict drug response. Transcriptomic analysis represents one of the most promising approaches to overcome this challenge, and relies on robust gene expression signatures designed to capture the core common features indicative of drug sensitivity, regardless of their precise molecular origin (Costello et al., 2014). Rapid technological advances are quickly making clinical implementation of these multi-gene signatures feasible (Cowin et al., 2010). For example, the 50-gene Prosigna based on the PAM50 gene set has been FDA approved (Wallden et al., 2015) and a 70-gene signature led to the development of MammaPrint, a commercially available DNA microarray that aids in the prediction of low-grade breast cancer prognosis, has recently completed phase III trials (Bogaerts et al., 2006; Cardoso et al., 2008; Cardoso et al., 2016). Other signatures have shown promise to predict genomic instability in cancers (Pitroda et al., 2014). Many studies have suggested that human cancer cell lines model many "omic" aspects of tumors, thereby making them representative proxies for the identification and evaluation of effective therapeutic interventions (Barretina et al., 2012; Heiser et al., 2012; Kao et al., 2009; Neve et al., 2006; Garnett et al., 2012). However, it has been challenging to implement successful approaches that leverage transcriptomic data from cells lines to predict patient responses because many drugs, including immune checkpoint inhibitors, work indirectly, and predicting patient response has been challenging. Thus, a clinical need remains for the improvement of methods to direct and enhance cancer therapies, and particularly immune checkpoint inhibitor therapies.

SUMMARY

In one embodiment, provided herein are in vitro methods of identifying a cancer as replication stress response (RSR) defective comprising: (a) obtaining a sample of the cancer from a patient; (b) assaying the expression levels of at least 3 of the genes listed in Tables 1A-B in the sample of the cancer; and (c) identifying the cancer as RSR defective if the expression level of said genes are up- or down-regulated compared to a control expression level; or identifying the cancer as not RSR defective if said genes are not up- or down-regulated compared to a control expression level.

In some aspects, at least one of the genes is a gene from Table 1A and the cancer is identified as RSR defective if the gene is up-regulated relative to a reference expression level; or the cancer is not identified as RSR defective if the gene is not up-regulated relative to a reference expression level. In certain aspects, the gene from Table 1A is MMP1 and/or DKK3.

In some aspects, at least one of the genes is a gene from Table 1B and the cancer is identified as RSR defective if the gene is down-regulated relative to a reference expression level; or the cancer is not identified as RSR defective if the gene is not down-regulated relative to a reference expression level. In certain aspects, the gene from Table 1B is CYBA.

In some aspects, the methods further comprise assaying the expression levels of at least 4, 5, 6, 7, 8, 9 or 10 of the genes listed in Tables 1A-B. In some aspects, the methods are methods of determining a prognosis and wherein identifying a cancer as RSR defective is indicative of increased risk of metastasis. In some aspects, the cancer is a kidney cancer, a breast cancer, an ovarian cancer, a glioblastoma, a melanoma, a stomach cancer, or a bladder cancer. In some aspects, the assayed gene expression levels comprise MMP1, DKK3, and CYBA expression levels.

In some aspects, the expression levels are analyzed by RNA sequencing. In some aspects, the expression levels are analyzed by microarray analysis. In some aspects, the expression levels are analyzed by labeled reporter probe hybridization and imaging. In certain aspects, the expression levels are analyzed by nanostring analysis. In some aspects, the expression levels are analyzed by qPCR. In some aspects, the expression levels are analyzed by reverse phase protein array analysis. In some aspects, the expression levels are analyzed by Western blot.

In some aspects, identifying the cancer as RSR defective further comprises identifying a patient having the cancer as a candidate for MEK inhibitor therapy and/or immune checkpoint inhibitor therapy. In some aspects, the control expression level is an expression level in a healthy tissue sample. In some aspects, the control expression level is an expression level in a non-cancerous cell obtained from the patient.

In one embodiment, provided herein are methods of classifying a patient having a cancer as being either sensitive or resistant to immune checkpoint inhibitors or MEK/ERK inhibitors, the method comprising: (a) obtaining a sample of the patient's cancer; (b) measuring an expression level of a plurality of genes in the sample, wherein each gene in the plurality of genes is selected from Tables 1A-B; (c) generating an expression profile based on a comparison between the expression level of the plurality of genes in the sample and a corresponding expression level obtained from a reference sample; and (d) classifying the patient as having a lymphoma that is either sensitive or resistant to immune checkpoint inhibitors or MEK/ERK inhibitors based on the expression profile. In some aspects, the cancer is a kidney cancer, a breast cancer, an ovarian cancer, a glioblastoma, a melanoma, a stomach cancer, or a bladder cancer.

In some aspects, the plurality of genes comprises at least 40 genes selected from Tables 1A-B. In some aspects, the plurality of genes comprises at least 45, 50, 55, or 60 genes selected from Tables 1A-B. In some aspects, the plurality of genes comprises all of the genes in Tables 1A-B. In some aspects, the patient is classified as having an immune checkpoint inhibitor sensitive cancer if the expression of MMP1 is upregulated, the expression of DKK3 is upregulated, and the expression of CYBA is downregulated.

In some aspects, the expression level of the plurality of genes is measured by detecting a level of mRNA transcribed from the plurality of genes. In some aspects, the mRNA level is detected by microarray, RT-PCR, qRT-PCR, nanostring assay, or in situ hybridization. In certain aspects, the mRNA level is measured using nanostring probes. In some aspects, the expression level of the plurality of genes is measured by detecting a level of cDNA produced from reverse transcription of mRNA transcribed from the plurality of genes. In some aspects, the expression level of the plurality of genes is measured by detecting a level of polypeptide encoded by the plurality of genes.

In some aspects, the sample is a formalin-fixed, paraffin-embedded sample. In some aspects, the sample is a fresh frozen sample. In some aspects, the reference sample is a sample from a healthy subject. In some aspects, the reference sample is a sample of non-cancerous cells obtained from the patient.

In some aspects, the methods further comprise reporting the classification of the patient. In some aspects, the reporting comprises preparing a written or electronic report. In some aspects, the methods further comprise providing the report to the patient, a doctor, a hospital, or an insurance company.

In some aspects, if the patient is determined to have an immune checkpoint inhibitor sensitive cancer, then the method further comprises administering a therapeutically effective amount of an immune checkpoint inhibitor to the patient. In some aspects, the immune checkpoint inhibitor is a CTLA-4 inhibitor, PD-1 inhibitor, or PD-L1 inhibitor. In certain aspects, the immune checkpoint inhibitor is ipilimumab, pembrolizumab, nivolumab, atezolizumab, avelumab, durvalumab, spartalizumab, AMP-224, or AMP-514.

In some aspects, if the patient is determined to have a MEK/ERK inhibitor sensitive cancer, then the method further comprises administering a therapeutically effective amount of a MEK/ERK inhibitor to the patient. In certain aspects, the MEK/ERK inhibitor is Trametinib, Cobimetinib, Binimetinib, Selumetinib, PD-325901, AZD 6244, or U0126.

In one embodiment, provided herein are methods of treating a cancer patient comprising: (a) selecting a patient determined to have a RSR defective cancer according to the method of any one of claims 1-19; and (b) treating the selected patient with a MEK inhibitor and/or an immune checkpoint inhibitor. In some aspects, the immune checkpoint inhibitor is a CTLA-4 inhibitor, PD-1 inhibitor, or PD-L1 inhibitor. In certain aspects, the immune checkpoint inhibitor is ipilimumab, pembrolizumab, nivolumab, atezolizumab, avelumab, durvalumab, spartalizumab, AMP-224, or AMP-514. In certain aspects, the MEK/ERK inhibitor is Trametinib, Cobimetinib, Binimetinib, Selumetinib, PD-325901, AZD 6244, or U0126. In some aspects, the methods further comprise administering a second anti-cancer therapy. In certain aspects, the second anti-cancer therapy is a DNA damage checkpoint inhibitor, a chemotherapy, a radiation therapy, a hormonal therapy, a targeted therapy, an immunotherapy or a surgical therapy.

In one embodiment, provided herein are methods of treating a cancer patient comprising administering a combined therapeutically effective amount of a DNA damage checkpoint inhibitor and an immune checkpoint inhibitor to the patient. In a further embodiment, methods are provided for treating a cancer patient comprising inducing a defect in replication stress response with by administering a combined therapeutically effective amount of a DNA damage checkpoint inhibitor or other inducing compound and an immune checkpoint inhibitor to the patient. In some aspects, the immune checkpoint inhibitor is a CTLA-4 inhibitor, PD-1 inhibitor, or PD-L1 inhibitor. In some aspects, the immune checkpoint inhibitor is ipilimumab, pembrolizumab, nivolumab, atezolizumab, avelumab, durvalumab, spartalizumab, AMP-224, or AMP-514. In some aspects, the DNA damage checkpoint inhibitor is a CHK inhibitor, a ATR inhibitor, a Wee1 inhibitor, or a DNA-PK inhibitor. In some aspects, the DNA damage checkpoint inhibitor is AZD7762, Prexasertib, GDC-0575, CCT245737, AZD6738, BAY1895344, M4344, Berzosertib, AZD1775, M9831, Nedisertib, or CC-115. In some aspects, the methods further comprise administering a further anti-cancer therapy. In certain aspects, the anti-cancer therapy is a chemotherapy, a radiation therapy, a hormonal therapy, a targeted therapy, an immunotherapy or a surgical therapy.

In some embodiments, the present disclosure provides a method for predicting patient response to therapy comprising analyzing the expression of genes associated with a defect in replication stress response to generate a replication stress response defect (RSRD) score. In some aspects, the genes associated with a defect in replication response are selected from the genes listed in Tables 1A-B. In certain aspects, the RSRD score is generated by comparing the expression coefficients of the genes being analyzed to the expression coefficients listed in Tables 1A-B.

In some aspects of the method, the RSRD score is generated by comparing the expression of genes listed in Tables 1A-B whose expression is either increased or decreased to the expression coefficients listed in Tables 1A-B. In one aspect, the RSRD score is generated by comparing the expression of genes listed in Tables 1A-B whose expression is increased to the expression coefficients listed in Tables 1A-B. In another aspect, the RSRD score is generated by comparing the expression of genes listed in Tables 1A-B whose expression is decreased to the expression coefficients listed in Tables 1A-B. In some aspects, the RSRD score is generated by comparing the expression of every gene listed in Tables 1A-B to the expression coefficients listed in Tables 1A-B. In certain aspects, the RSRD score is generated by comparing the expression of at least 3 genes selected from the genes listed in Tables 1A-B to the expression coefficients listed in Tables 1A-B. In specific aspects, the expression of MMP1, DKK3, and CYBA are analyzed.

In some aspects of the method, the patient has cancer, such as breast, pancreas, bladder, kidney, stomach, thyroid, head and neck, or squamous cell lung cancer, or melanoma or glioblastoma. In certain aspects, the cancer is kidney cancer. In a specific aspect, the cancer is renal clear cell carcinoma. In particular aspects, the genes analyzed are further associated with the cancer.

In some aspects of the method, the therapy is immune checkpoint inhibitor therapy. In certain aspects, the immune checkpoint inhibitor is a CTLA-4 inhibitor, PD-1 inhibitor, or PD-L1 inhibitor. In specific aspects, the immune checkpoint inhibitor is ipilimumab, pembrolizumab, nivolumab, atezolizumab, avelumab, durvalumab, spartalizumab, AMP-224, or AMP-514. In some aspects, the therapy is a MEK/ERK inhibitory therapy. In certain aspects, the MEK/ERK inhibitor comprises Trametinib, Cobimetinib, Binimetinib, Selumetinib, PD-325901, AZD 6244, or U0126. In some aspects, the therapy is a combination therapy. In certain aspects, the combination therapy is immune checkpoint inhibitor therapy, and at least one other anti-cancer therapy. In specific aspects, the at least one other anti-cancer therapy is selected from the group consisting of DNA damage checkpoint inhibitor, radiotherapy, hormonal therapy, gene therapy, immunotherapy, IDO inhibitor therapy, or tumor resection.

In some aspects, the gene expression analysis is performed by RNA sequencing. In another aspect, the gene expression analysis is performed by microarray analysis. In certain aspects, the gene expression analysis is performed by labeled reporter probe hybridization and imaging. In specific aspects, the gene expression analysis is performed by nanostring analysis. In some aspects, the gene expression analysis is performed by qPCR. In another aspect, the gene expression analysis is performed by reverse phase protein array analysis. In yet another aspect, the gene expression analysis is performed by Western blot.

In another embodiment, the present disclosure provides a method for predicting tumor risk in a biological sample comprising analyzing the expression of genes associated with a defect in replication stress response to generate a RSRD score. In some aspects, a high RSRD score is indicative of increased tumor risk.

In another embodiment, the present disclosure provides a method for treating a subject identified by a method in accordance with any of the other aspects or embodiments of the disclosure, further comprising administering an effective amount of an anti-cancer therapy to the subject.

In another embodiment, the present disclosure provides a method for treating a subject who is at risk of, is expected to have, or has cancer, comprising analyzing the expression of genes associated with a defect in replication stress response to generate a RSRD score and, for a subject whose RSRD score is in the upper tertile, administering to the subject a therapeutically effective amount of an immune checkpoint inhibitor to treat the subject. In another embodiment, there is provided a method for treating a subject who is at risk of, is expected to have, or has cancer, comprising analyzing the expression of genes associated with a defect in replication stress response to generate a RSRD score and, for a subject whose RSRD score is greater than 0.04, and administering to the subject a therapeutically effective amount of an immune checkpoint inhibitor to treat the subject. In some aspects, the genes associated with a defect in replication response are selected from the genes listed in Tables 1A-B.

In some aspects of the method, the RSRD score is generated by comparing the expression coefficients of the genes being analyzed to the expression coefficients listed in Tables 1A-B. In certain aspects the RSRD score is generated by comparing the expression of genes listed in Tables 1A-B whose expression is either increased or decreased to the expression coefficients listed in Tables 1A-B. In specific aspects, the RSRD score is generated by comparing the expression of genes listed in Tables 1A-B whose expression is increased to the expression coefficients listed in Tables 1A-B. In particular aspects, the RSRD score is generated by comparing the expression of genes listed in Tables 1A-B whose expression is decreased to the expression coefficients listed in Tables 1A-B. In specific aspects, the RSRD score is generated by comparing the expression of every gene listed in Tables 1A-B to the expression coefficients listed in Tables 1A-B. In some aspects, the RSRD score is generated by comparing the expression of at least 3 genes selected from the genes listed in Tables 1A-B to the expression coefficients listed in Tables 1A-B. In specific aspects, the expression of MMP1, DKK3, and CYBA are analyzed.

In some aspects of the method, the patient has cancer. In certain aspects, the cancer is breast, pancreas, bladder, kidney, stomach, thyroid, head and neck, or squamous cell lung cancer, or glioblastoma, or melanoma. In particular aspects, the cancer is kidney cancer. In specific aspects, the cancer is renal clear cell carcinoma. In some aspects, the genes analyzed are further associated with the cancer.

In some aspects of the method, the therapy is immune checkpoint inhibitor therapy. In certain aspects, the immune checkpoint inhibitor is a CTLA-4 inhibitor, PD-1 inhibitor, or PD-L1 inhibitor. In specific aspects, the immune checkpoint inhibitor is ipilimumab, pembrolizumab, nivolumab, atezolizumab, avelumab, durvalumab, spartalizumab, AMP-224, or AMP-514. In some aspects, the therapy is a MEK/ERK inhibitory therapy. In certain aspects, the MEK/ERK inhibitor comprises Trametinib, Cobimetinib, Binimetinib, Selumetinib, PD-325901, AZD 6244, or U0126. In some aspects, the therapy is a combination therapy. In certain aspects, the combination therapy is immune checkpoint inhibitor therapy, and at least one other anti-cancer therapy. In specific aspects, the at least one other anti-cancer therapy is selected from the group consisting of DNA damage checkpoint inhibitor, radiotherapy, hormonal therapy, gene therapy, immunotherapy, IDO inhibitor therapy, or tumor resection.

In some aspects of the method, the gene expression analysis is performed by RNA sequencing. In certain aspects, the gene expression analysis is performed by microarray analysis. In particular aspects, the gene expression is performed by labeled reporter probe hybridization and imaging. In specific aspects, the gene expression is performed by nanostring analysis. In some aspects, the gene expression analysis is performed by qPCR. In another aspect, the gene expression analysis is performed by reverse phase protein array analysis. In yet another aspect, the gene expression analysis is performed by western blot.

In another embodiment, the present disclosure provides a method for predicting tumor risk in a biological sample comprising analyzing the expression of genes associated with a defect in replication stress response to generate a RSRD score. In some aspects, the genes associated with a defect in replication stress response are selected from the genes listed in Tables 1A-B.

In another embodiment, the present disclosure provides a method for predicting the risk of cancer development in a subject, comprising analyzing the expression of genes associated with a defect in replication stress response to generate a RSRD score. In some aspects, the genes associated with a defect in replication stress response are selected from the genes listed in Tables 1A-B.

In another embodiment, there is provided a method for predicting the risk of metastasis in a subject having cancer comprising analyzing the expression of genes associated with a defect in replication stress response to generate a RSRD score. In some aspects, the genes associated with a defect in replication stress response are selected from the genes listed in Tables 1A-B.

In another embodiment, there is provided a method for measuring the expression of at least 2 genes listed in Tables 1A-B in a subject, comprising determining the amount of mRNA of the at least 2 genes listed in Tables 1A-B present in a sample.

In another embodiment, there is provided a kit for analyzing the expression of at least 2 genes listed in Tables 1A-B, comprising probes or primers directed to the at least 2 genes listed in Tables 1A-B. In some aspects, the kit is for analyzing the expression of at least 3 genes listed in Tables 1A-B. In some aspects, probes are provided for the analysis of at least the MMP1, DKK3, and CYBA genes.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-I: Generation and characterization of a replication stress response defect (RSRD) cell model and establishment of a RSRD gene signature that predicts tumor risk from hyperplastic breast tissue. (FIG. 1A) Schematic of replication stress response defect model. Non-malignant MCF-10A mammary epithelial cells were engineered with an inducible oncogene (Cyclin E) and then stably depleted of key RSR signaling factors ATR, ATM, CHEK1, and CHEK2. Following oncogene induction, the scrambled shRNA undergoes oncogene-induced senescence, but RSR defect model lines escape OIS and continue to proliferate. (FIG. 1B) Growth rates of shCTRL, shCTRL with cyclin E, and RSR defective cell lines. Doxycycline (2 μg/mL) was added 24 hours prior to start of the experiment. (FIG. 1C) Western blot shows that induction of Cyclin E increases p21 protein levels in to in shRNA control, but not in RSR defect lines. Doxycycline (2 μg/mL) was added 48 hours prior to collection of cell lysates. (FIG. 1D) Single cell electrophoresis (comet assay) quantified by tail moment, where a larger tail moment indicates increased double-stranded DNA breaks. See images in FIG. 9H. *$p<0.05$ (FIG. 1E) Cells immunostained for DNA double strand break marker γH2AX. Scale bar=10 μm. (FIG. 1F) Replication restart assay. Cells were treated with hydroxyurea for 16 hours to stall replication forks and then released into nocodazole. Intact RSR is indicated by accumulation of cells with 4N DNA indicative of completing the cell cycle after replication restart, whereas RSR defects manifest by accumulation of S phase cells. (FIG. 1G) Venn diagram of differentially expressed genes in each of the model cell lines (false discovery rate of 5% with 1.25 fold change threshold). The 712 genes common to all four model cell lines were defined as the RSRD gene signature. (FIG. 1H) Quantification of gene signature based RSRD score following induction of cyclin E. The left column of each pair is (− Cyclin E) and the right column is (+ Cyclin E). (FIG. 1I) Enrichment of RSRD score in hyperplastic tissue that would eventually form cancer (cancer) compared to samples that did not go on to form cancer (no cancer). Wilcoxon rank-sum $p<0.01$ (FIG. 2A) Gene set enrichment analysis for the RSRD gene signature show strong enrichment for the mammary stem cell phenotype. Positive net enrichment score (NES) for mammary stem cell up indicates this pathway is up-regulated, negative NES for mammary stem cell down indicates these genes are down-regulated. Significance indicated by FDR q-value. (FIG. 2B) Model cell lines were cultured on Matrigel in presence or absence of serum for 10 days. RSRD were able grow in absence of growth factors (-serum), and formed atypical multiacinar structures as demonstrated by H&E staining. Doxycycline (2 μg/mL) was added 24 hours prior to start of the experiment and maintained throughout the course of the experiment. Scale bar=100 μm. (FIG. 2C) Aldehyde dehydrogenase activity detected using Aldefluor reagent by flow cytometry. Results were plotted with FITC (Aldefluor) on the x-axis and SSC on the y-axis. Graph showing mean+/−S.E.M of three independent experiments. Cells were gated relative to a DEAB-treated negative control and quantified by percent positivity. *$p<0.001$ (FIG. 2D) Increased mammosphere formation in RSRD cells. Cells were grown in ultra-low attachment plates with serum-free mammosphere media for 7 days before counting the number of mammospheres. Doxycycline (2 μg/mL) was added 24 hours prior to start of the experiment and maintained throughout the course of the experiment. Phase-contrast images showing model cell lines after 7 days of growth were obtained. Shown is the quantification of number of mammospheres formed per 1000 cells, displayed as mean+/−S.E.M. of three independent biological replicates. ***$p<0.001$ (FIG. 3A) RSRD score calculated for primary patient tumors, as well as following enrichment of CSCs by culturing mammospheres (MS) in anchorage-independent, low serum conditions from primary tumors.

Stem-like P4 cells were cultured ex vivo for 4 passages before repeating the analysis indicating the phenotype is reversible. *Wilcoxon rank-sum p<0.05. (FIG. 3B) RSRD score calculated from primary patient tumors following sorting for the CSCs (defined as CD44$^{high}$/CD24$^{low}$) compared to the remaining other cells. *Wilcoxon rank-sum p<0.001. (FIG. 3C) RSRD score calculated for MCF7 luminal breast cancer cells transformed to a stem-like state by stable overexpression of SNAIL relative to empty vector control. p<0.01. (FIG. 3D) Replication restart assay in MCF7-SNAIL and vector control cells. Following treatment with hydroxyurea (HU) for 16 hours to stall replication forks or water mock control (CTRL), cells were released into nocodazole to collect cells capable of completing S phase in G2/M. Intact RSR is indicated by equivalent accumulation of cells in G2/M (4N DNA) in control and HU treated cells, whereas RSR defects are indicated by a decreased accumulation of HU-treated cells in G2/M. (FIG. 3E) Percentage of cells with intact RSR, defined as 100·(% 4N DNA)$_{HU}$/(% 4N DNA)$_{CTRL}$. *p<0.001. (FIG. 3F) Replication restart assay in CSC/stem-like cells per FIG. 3D isolated from human mammary tumor cell lines (MCF-7, ZR-75-1), mouse mammary tumor cell line M158, and human colorectal cancer cell line HT-29. Stem-like cells were cultured for two passages in mammosphere conditions before re-isolation in standard growth conditions to allow for the assay to be run under matched conditions. (FIG. 3G) Percentage of cells with intact RSR, defined as 100·(% 4N DNA)1 HU/(% 4N DNA)CTRL. The left column of each pair is "Parental" and the right column is "Stem-like." p<0.01, *p<0.05. (FIG. 3H) Cells were immunostained for native BrdU to detect single-stranded DNA breaks and γH2AX to detect double-stranded DNA breaks in parental and stem-like cell lines isolate per FIG. 3F. Exogenous replication stress was induced by addition of 2 mM hydroxyurea (HU) for 6 hours. Shown is the quantification of the percentage of cells positive for single-stranded DNA (ssDNA) indicative of single-stranded DNA breaks and γH2AX indicative of double stranded breaks. The left column of each pair is "Mock" and the right column is "HU."

(FIG. 4A) Summary results of primary drug screen, with drugs targeting MEK inhibitors shown in red. Relative sensitivity is defined as the average growth inhibition of RSR defect model cells minus the sensitivity of shCTRL cells, with larger values indicating increased specificity towards RSR defective cells. (FIG. 4B) Representative plots for select classes of inhibitors following high-throughput drug screening. Percent growth inhibition is quantified relative to DMSO treated control. For each group of five columns, the bars represent, from left to right: shCTRL, shATR, shCHK1, shATM, and shCHK2. (FIG. 4C) Inhibition of MEK or ERK restores oncogene-induced senescence as show by staining for senescence-associated β galactosidase. Cells were treated with 0.5 μM AZD6244 (MEKi) or 0.1 M ERKi (SCH772984) for 48 hours before staining. For each group of three columns, the bar represent, from left to right: DMSO, AZD6244 (MEKi), and SCH772984 (ERKi).

FIGS. 5A-E: CSCs are depleted by MEK/ERK inhibition in breast cancer cell lines. (FIG. 5A) Stem cell score calculated following MEK inhibition (48 hours, 0.5 μM AZD6244) in MCF10A shATR cells shows MEKi can reverse the stem-cell phenotype. *p<0.05, p<0.01. (FIG. 5B) Quantification of CSC depletion using by aldehyde dehydrogenase (ALDH) positivity as measured using the Aldefluor detection kit by flow cytometry. Positivity was determined relative to a DEAB-treated negative control. MCF10A shATR over-expressing cyclin E were incubated with inhibitors for MEK (0.5 μM AZD6244), ERK (0.1 μM SCH772984), or DMSO solvent control for 48 hours before analysis. Doxycycline (2 μg/mL) was added 24 hours prior to inhibitors and maintained throughout the course of the experiment. p<0.01. (FIG. 5C) Human triple negative breast cancer cell lines MDA-MB-231 and MDA-MB-436 were analyzed per FIG. 5B after treatment with inhibitors for MEK (1.0 μM AZD6244), ERK (0.1 μM SCH772984), or DMSO solvent control for 48 hours before analysis. *p<0.001. (FIG. 5D) Human luminal/ER+ breast cancer cell lines MCF7 and MCF7-stem enriched subpopulation were analyzed per FIG. 5B after treatment with an ERK inhibitor (1.0 μM SCH772984) or DMSO solvent control for 48 hours before analysis. *p<0.001. (FIG. 5E) Murine triple negative mammary tumor cell lines M158 and 1 4T1 were analyzed per FIG. 5B after treatment with an ERK inhibitor (1.0 μM SCH772984) or DMSO solvent control for 48 hours before analysis. **p<0.01

(FIG. 6A) Western blots showing that inhibition of MEK (0.5 μM AZD6244) or ERK (0.1 μM SCH772984) for 48 hours recovers p21 protein expression. Doxycycline (2 μg/mL) was added 24 hours prior to inhibitors and maintained throughout the course of the experiment. (FIG. 6B) Western blots showing induction of p21 following siRNA-mediated depletion of ERK1/2. Lysates were harvested 72 hours after siRNA transfection. (FIG. 6C) Cells were transfected with control siRNA (siCTRL) or p21 siRNA (siP21) 24 hours before addition of 0.5 μM AZD6244 (MEKi) or 0.1 μM ERKi (SCH772984) for 48 hours. The left column of each pair represented "siCTRL" and the right column "siP21. " (FIG. 6D) Unsupervised hierarchical clustering of reverse-phase protein array (RPPA) results for model cell lines following treatment with MEK inhibitors for 48 hours reveal severe depression of phosphorylated MDM2, which clustered near MEK/ERK effector ETS1. (FIG. 6E) Phospho-MDM2 levels in RSRD model cells following treatment with MEK inhibitors AZD6244 and CI1040. For each group of five columns, the bars represent, from left to right: shCTRL, shATR, shCHK1, shATM, and shCHK2. (FIG. 6F) RPPA data from hundreds of cell lines was retrieved from the MD Anderson Cell Line Project (MCLP) and used to determine the Spearman correlation coefficient of phospho-MDM2 with phosphorylated ERK1/2, ETS1, and phosphorylated MEK1. (FIG. 6G) Western blot data following 48 hour treatment with 0.1 μM SCH772984 (ERKi) or DMSO vehicle control for 48 hours verifies suppression of MDM2 phosphorylation and shows negligible changes in p53 levels. Doxycycline (2 μg/mL) was added 24 hours prior to inhibitors and maintained throughout the course of the experiment. (FIG. 6H) Cells were transfected with siRNA for MDM2 or scrambled control 72 hours before collection of lysates. Doxycycline (2 μg/mL) was added immediately post-transfection. Depletion of MDM2 produced equivalent results to those seen by inhibition of MEK/ERK.

FIGS. 7A-D: Replication stress response defect (RSRD) score predicts response to immunotherapy in kidney cancer patients. For all samples, RSRD score was determined by taking the Spearman correlation coefficient between gene coefficients in the RSRD signature and expression values in a given sample. (FIG. 7A) Progression free survival stratified by RSRD score. The top line is RSRD High; the bottom line is RSRD Low. (FIG. 7B) Overall survival stratified by RSRD score. The top line is RSRD High; the bottom line is RSRD Low. (FIG. 7C) Receiver-operating characteristic curve for RSRD score predicting clinical benefit. (FIG. 7D) Multivariate survival analysis taking RSRD score, PBRM1 mutation status, and previous treatment as co-variates.

FIGS. 8A-C: Correlation between cytotoxic T cell infiltration and mutational burden across TCGA cohorts. Neoantigens and CTL score were determined based on RNAseq analysis as described in Charoentong et. al., Cell Reports 2017 (18)248-262. (FIG. 8A) CTL score calculated across 19 cancers, plotted in order of median for each cancer. Dots represent individual patients, and lines are median with interquartile range. (FIG. 8B) Neoantigens per patient across 19 cancers, plotted in order of median CTL score for each cancer. Dots represent individual patients, and lines are median with interquartile range. (FIG. 8C) Spearman correlation between CTL score and neoantigen levels on a per lineage bases. $p<0.01$ *$p<0.001$, ****$p<1\times10^5$.

FIGS. 9A-I: RSR defect model cell lines. (FIG. 9A) Growth curve wild type MCF-10A, MCF-10AE (no doxycycline, non-induced) and MCF-10AE cyclin E induced with doxycycline. (FIG. 9B) Colony forming assay with MCF-10A, MCF-10A E and MCF-10A E cyclin E induced with doxycycline and staining for senescence-associated β galactosidase (SA-βgal) showing cyclin E induced lines are becoming senescent. (FIG. 9C) Activation of DNA damage response following cyclin E expression. (FIG. 9D) Validation of knockdown in RSRD model cell lines. (FIGS. 9E-F) Checkpoint activation in response to genotoxic agents. Cells were treated with either 2 mM hydroxyurea (HU, FIG. 9E) or 1 M camptothecin (CMPT, FIG. 9F) for specified length of time and then probed for down-stream signaling activation by western blot. (FIG. 9G) Colony forming assay showing RSRD cell lines can escape oncogene-induced senescence. (FIG. 9H) Comet assay, related to FIG. 1D. (FIG. 9I) Induction of cyclin E does not significantly alter p21 transcript levels.

FIGS. 10A-D: RSR defects through chemical inhibitors. (FIG. 10A) Dose-response of MCF-10AE to ATR inhibitor VE821, ATM inhibition KU55933, or Chk1/2 inhibitor AZD7762 in with (+Cyclin E, squares) and without (−Cyclin E, circles) cyclin E induction. Doxycyline (2 µg/mL) and inhibitors were co-administered and cells incubated for 5 days before analysis of viability by PrestoBlue, values reported normalized to solvent-treated control. (FIG. 10B) Relative viability of cyclin E induced vs noninduced cells shows that while low doses of inhibitors promote growth of cyclin E-induced cells, higher doses are more lethal to cyclin E-induced cells. (FIG. 10C) Expression of p21 following treatment with ATR inhibitor VE821 (50 nM), ATM inhibition KU55933 (100 nM), Chk1/2 inhibitor AZD7762 (20 nM) or solvent control (DMSO) with (+Cyclin E) and without (−Cyclin E) cyclin E induction. Doxycyline (2 µg/mL) and inhibitors were co-administered and cells incubated for 2 days before protein extraction and analysis by western blot. Inhibitor concentrations were chosen based on maximum viability in FIG. 10A, and closely mirror kinase inhibition IC50 values of 15 nM for VE821, 12.9 nM for KU55933, and 5 nM for AZD7762. (FIG. 10D) Cells were treated per S2C and then stained for senescence associated β-galactosidase. Percentages of SA β-gal positive cells were determined based on 8 fields of view from 3 independent experiments.

FIGS. 11A-D: RSR defects induce a CSC phenotype. (FIG. 11A) Change in gene expression levels of aldehyde dehydrogenase isoforms. For each group of five columns, the bars represent, from left to right: ALDH1A1, ALDH1A2, ALDH1A3, ALDH1B1, and ALDH1L1. (FIG. 11B) Up-regulation of ALDH1A3 verified by western blot. (FIG. 11C) Mammosphere assay replicates using other base cell lines (HMEC) and other oncogenes (HRAS G12D). (FIG. 11D) Equivalent mammosphere results are seen with or without oncogene induction. Cells were induced 24 hours before plating, with continued presence of doxycycline throughout the assay.

FIGS. 12A-G: RSR defects in CSC-like cells. (FIG. 12A) Replication restart assay in CSC/stem-like cells isolated from human breast cancer cell lines MCF-7 and ZR-75-1. Stem-like cells were cultured for two passages in mammosphere conditions before re-isolation in standard growth conditions to allow for the assay to be run under matched conditions (Stem-like) or continually cultured for 3 passages (Stem-like P3). Cells were treated with hydroxyurea for 16 hours to stall replication forks and then released into nocodazole. Intact RSR is indicated by accumulation of cells with 4N DNA indicative of completing the cell cycle after replication restart, whereas RSR defects manifest by accumulation of S phase cells. (FIG. 12B) Recovery from HU-induced stalled replication forks. Stem-like cells were isolated per S4A, and plated into 96 well plates. Replication forks were stalled for 16 hours with hydroxyurea then released for various lengths. S-phase cells were labeled with EdU, which was tagged with biotin (biotin PEG3 azide) using click chemistry and fluorescently labeled with AlexaFluor 596 streptavidin. Nuclei were counterstained with DAPI. Images (16 per well) were acquired on an INCELL 1000 ensuring at least 1000 cells per well, quantified in MATLAB, and exported for cell cycle analysis in FlowJo. (FIG. 12C) Western blot analysis of RSR checkpoint proteins relative to actin loading control in parental (P) and stem-like CSC populations (S) isolated from breast cancer cell lines ZR751 and MCF7. (FIG. 12D) Quantification western blots for RSR checkpoint proteins in parental (left bar of each pair) and stem-like (right bar of each pair) populations from S4D. N=3 independent isolations. **$P<0.01$, *$P<0.05$ computed from post-hoc test following two-way ANOVA with Sidak correction for multiple comparisons. (FIG. 12E) Western blot analysis of CHK1 phosphorylation following treatment with 2 mM HU for indicated times in ZR751 parental and stem-like cells. (FIG. 12F) Quantification of cells positive for phosphorylated substrates of ATM/ATR as indicated by staining for the phospho-SQ/TQ motif, which has shown specificity to substrates of ATM/ATR. (FIG. 12G) Recovery of cells positive for single stranded DNA (ssDNA, as determined by native BrdU staining) and double stranded breaks (γH2AX). Cells were either mock treated with water (left most column of each group) or with hydroxyurea (HU, middle column of each group) for 16 hours. To analyze recovery, cells were washed with media and then returned to fresh, pre-equilibrated growth media for 10 hours (HU washout, right most column of each group).

FIGS. 13A-C: MEK/ERK inhibition induces senescence in RSRD cells via MDM2/p21 independent of p53. (FIG. 13A) Cells were transfected with either non-targeting (NT) or TP53 siRNA. After 24 hours, cells were exposed to 0.5 µM AZD6244 or solvent control for 48 hours before harvesting protein in presence of 2 µg/mL doxycyline. (FIG. 13B) MCF-10AE shATR cells were treated as in FIG. 13A and then stained for p galactosidase. (FIG. 13C) Lysates from model cell lines with cyclin E induced by 48 hour treatment with 2 µg/mL doxycycline or without cyclin E induction were probed for MDM2 pS166 and p21, demonstrating that this phosphorylation site is only upregulated in RSR defect cell lines.

FIGS. 14A-D: RSR defect score is linked with breast cancer metastasis. (FIGS. 14A-B) Subclones of breast cancer cell line MDA-MB-231 with varying degrees of metastatic potential from two separate studies show strong correlation with RSRD score. Metastatic potential grouped as 0% (−), under 30% (+), 30%-70% (++), or above 70% (+++) of mice bearing metastasis after 60 days. (FIGS. 14C-D) RSRD score predicts likelihood of patient metastasis, as indicated by metastasis-free survival of breast cancer patients of all subtypes (FIG. 14C) or only triple-negative (FIG. 14D). HR=hazard ratio, or relative increase in metastasis risk for RSRD High patients. P=log-rank P-value.

FIGS. 15A-D: Validation of signature activity in secondary patient cohorts. (FIG. 15A) RSRD score was evaluated in kidney cancer patients treated with immunotherapy from Ascierto et al. (2016). Patients with clinician-assessed responding patients was significantly higher than non-responding patients. (FIG. 15B) RSRD score was evaluated in low mutation (less than 100 mutations) melanoma patients from Hugo et al. (2016) and Riaz et al. (2017), finding a significantly higher RSRD score in patients who showed response to immunotherapy. (FIG. 15C) Predictive capacity of the RSRD signature score in bladder cancer from patients in Snyder et al. (2017). While no activity was observed in high-mutator/M-class cancers, the response of low mutation C-Class cancers was accurately predicted by RSRD score. (FIG. 15D) Prediction of response to immunotherapy in stomach cancer patients from Kim et al. (2018) by RSRD score. Minimal predictive accuracy was observed in bulk patients (All), but signature activity was observed in the low-mutation microsatellite stable (MSS) patients.

FIGS. 16A-H: Replication stress response defect (RSRD) score predicts functional replication stress response defects in human breast and kidney cancer cell lines, which correspond with increased cytoplasmic DNA and STING-dependent cytokine production. (FIG. 16A) RSR function assessed by fraction of cells capable of completing cell cycle after replication stress. Hydroxyurea-induced replication stress synchronizes cells in G1/early S. Cells are released into nocodazole for collection in G2/M. Cells with intact RSR will complete the cell cycle, whereas RSR-defective cells will remain in G1/S phase. (FIG. 16B) Larger panel of breast cancer cell lines. (FIG. 16C) Example staining of ssDNA foci indicative of replication stress in BT-549 cells, as detected by native BrdU. (FIG. 16D) Quantification of ssDNA nuclear staining in RSRD-high and RSRD-low breast cancer cell lines. (FIG. 16E) Quantification of ssDNA nuclear staining in RCC cell lines. (FIG. 16F) Quantification of cytoplasmic ssDNA by immunostaining in breast (grey dots) and RCC (labeled dots) cell lines. Membranes were selectively permeabilized with saponin, and ssDNA degraded with S1 nuclease as a negative control. (FIG. 16G) RCC cell cytokine expression quantified by qRT-PCR following treatment with either 100 nM AZD-7762 (CHKi) or DMSO vehicle control for 24 hours. (FIG. 16H) Cytokine gene expression in RSRD-high 786-0 RCC cells following transfection with siRNA against TMEM173 (STING) or non-targeting control.

FIGS. 17A-G. Validation of signature activity in GBM patients from Zhao et al. (2019) and Cloughesy et al. (2019). (FIGS. 17A-D) RNA-sequencing gene expression data of GBM patients was acquired from Zhao et al. (2019), which had 1-3 biopsies per patient acquired pre- and/or post-treatment with PD1 inhibitors (nivolumab, N=13, pembrolizumab, N=4). Two patients only had post-treatment biopsies (1 nivolumab and 1 pembrolizumab treated). All plots represent accuracy at predicting objective response. Overall accuracy ranged from 82%-87% depending on conditions described in FIG. 17A-D. (FIG. 17A) ROC plot determined by taking average RSRD score from all available pre-treatment biopsies (15 patients), excluding 2 patients that only had post-treatment expression data. (FIG. 17B) ROC plot for patients in (FIG. 17A), but only using biopsy taken closest to start of treatment to determine RSRD score. (FIG. 17C) ROC plot including 2 patients with only post-treatment biopsies, taking average RSRD score from all biopsies. (FIG. 17D) ROC plot for patients in (FIG. 17C), but only using biopsy taken closest to start of treatment to determine RSRD score. (FIGS. 17E-G) RNA-sequencing gene expression data of GBM patients treated with pembrolizumab was acquired from Cloughesy et al. (2019) with associated overall survival data. Here, one cohort was treated with pembrolizumab in both neoadjuvant and adjuvant setting (FIG. 17E, N=14), and one cohort was only treated in the adjuvant setting (FIG. 17F, N=15). The top lines are RSRD-High; the bottom lines are RSRD-Low. (FIG. 17G) While neoadjuvant treatment showed a 6.2 month improvement in survival, multivariate analysis of entire cohort showed significantly improved outcomes in RSRD high patients (Cox proportional hazards model).

DETAILED DESCRIPTION

Figure 2A:
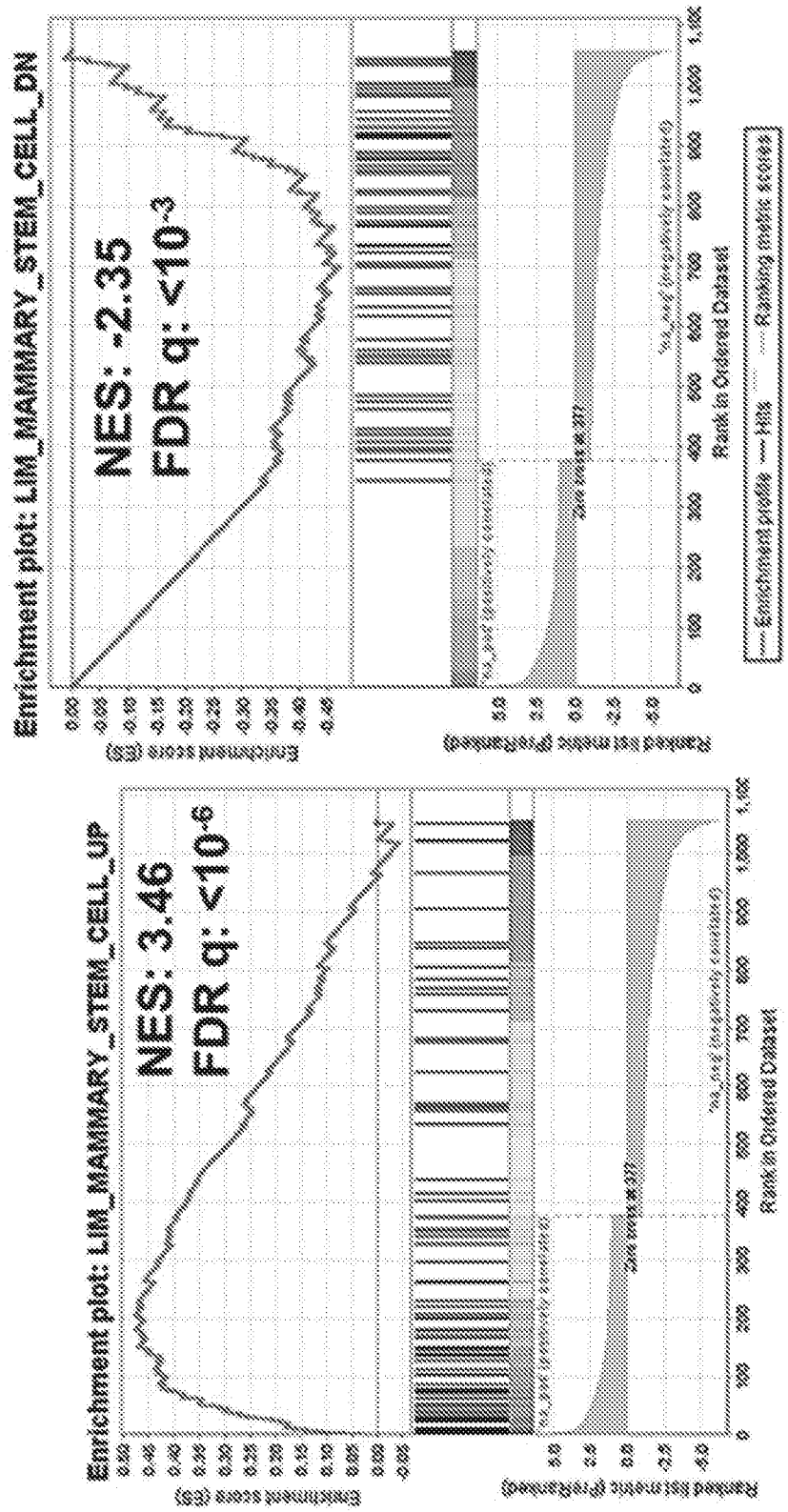
FIGS. 2A-D: RSR defects induce a CSC phenotype.

Despite rapid advancement in generation of large-scale microarray and RNA-seq gene expression datasets, robust multigene expression signatures that are capable of guiding the use of specific therapies have not been routinely implemented into clinical care. The present disclosure overcomes challenges associated with current technologies by developing a gene signature associated with a defect in replication stress response, indicative of immune checkpoint inhibitor therapy sensitivity.

The present studies established an RSR defective cell model in non-transformed mammary epithelial cells by individual depletion of ATR, ATM, CHEK1, or CHEK2. By implementing genome-wide transcriptome profiling to identify unique molecular changes associated with RSR defects, a gene signature was developed that could predict the risk of tumorigenesis from precancerous atypical ductal hyperplasia. This gene signature was enriched for stemness-associated genes by gene set enrichment analysis, and these model cells displayed many characteristics of CSCs.

Moreover, isolation of stem-like cancer cells revealed that they indeed harbored endogenous RSR defects that were not present in parental cell lines. These findings suggest that RSR defects in CSCs may promote early tumorigenesis. High-throughput screening hundreds of compounds revealed that activation of the MEK pathway was required for survival of RSR defective cells. Inhibition of the MEK/ERK pathway selectively targeted RSR defective cells showing both high efficacy and specificity compared to control cells. Mechanistically, RSR defective cells rely on MEK/ERK mediated phosphorylation of MDM2 to degrade p21, thereby escaping senescence. Blockade of MEK/ERK prevents MDM2 phosphorylation leading to p21 accumulation restoring OIS independent of p53. In summary, these findings highlighting the role of replication stress response defects in cancer progenitors, offer new insight into CSC biology, improve cancer risk assessment in precancerous stages, and provide targetable therapeutic pathways for cancer prevention and treatment.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is preferably below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising," the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The term "subject" or "patient" as used herein refers to any individual to which the subject methods are performed. Generally the patient is human, although as will be appreciated by those in the art, the patient may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of patient.

"Treatment" and "treating" refer to administration or application of a therapeutic agent to a subject or performance of a procedure or modality on a subject for the purpose of obtaining a therapeutic benefit of a disease or health-related condition. For example, a treatment may include administration chemotherapy, immunotherapy, radiotherapy, performance of surgery, or any combination thereof.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the invasiveness of a tumor, reduction in the growth rate of the cancer, or prevention of metastasis. Treatment of cancer may also refer to prolonging survival of a subject with cancer.

"Prognosis" refers to as a prediction of how a patient will progress, and whether there is a chance of recovery. "Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression-free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis and/or cancer progression in a patient susceptible to or diagnosed with a cancer. Prognosis also includes prediction of favorable survival following cancer treatments, such as a conventional cancer therapy or immune checkpoint blockade.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The term "immune checkpoint" refers to a molecule such as a protein in the immune system which provides inhibitory signals to its components in order to balance immune reactions. Known immune checkpoint proteins comprise CTLA-4, PD1 and its ligands PD-L1 and PD-L2 and in addition LAG-3, BTLA, B7H3, B7H4, TIM3, KIR. The pathways involving LAG3, BTLA, B7H3, B7H4, TIM3, and KIR are recognized in the art to constitute immune checkpoint pathways similar to the CTLA-4 and PD-1 dependent pathways (see e.g., Pardoll, 2012; Mellman et al., 2011).

An "immune checkpoint inhibitor" refers to any compound inhibiting the function of an immune checkpoint protein. Inhibition includes reduction of function and full blockade. In particular the immune checkpoint protein is a human immune checkpoint protein. Thus the immune checkpoint protein inhibitor in particular is an inhibitor of a human immune checkpoint protein.

Exemplary immune checkpoint inhibitors include, for example, ipilimumab (targeting CTLA-4, marketed as Yervoy®), pembrolizumab (targeting PD-1, marketed as Keytruda®), nivolumab (targeting PD-1, marketed as Opdivo®), atezolizumab (targeting PD-L1, marketed as Tecentriq®), avelumab (targeting PD-L1, marketed as Bavencio®), and durvalumab (targeting PD-L1, marketed as Imfinzi®). Immune checkpoint inhibition encompasses both reduction of function and full blockade.

The term "determining an expression level" as used herein means the application of a gene specific reagent such as a probe, primer or antibody and/or a method to a sample, for example a sample of the subject and/or a control sample, for ascertaining or measuring quantitatively, semi-quantitatively or qualitatively the amount of a gene or genes, for example the amount of mRNA. For example, a level of a gene can be determined by a number of methods including for example immunoassays including for example immunohistochemistry, ELISA, Western blot, immunoprecipitation and the like, where a biomarker detection agent such as an antibody for example, a labeled antibody, specifically binds the biomarker and permits for example relative or absolute ascertaining of the amount of polypeptide biomarker, hybridization and PCR protocols where a probe or primer or primer set are used to ascertain the amount of nucleic acid biomarker, including for example probe based and amplification based methods including for example microarray analysis, RT-PCR such as quantitative RT-PCR, serial analysis of gene expression (SAGE), Northern Blot, digital molecular barcoding technology, for example Nanostring: nCounter™ Analysis, and TaqMan quantitative PCR assays. Other methods of mRNA detection and quantification can be applied, such as mRNA in situ hybridization in formalin-fixed, paraffin-embedded (FFPE) tissue samples or cells. This technology is currently offered by the QuantiGene®ViewRNA (Affymetrix), which uses probe sets for each mRNA that bind specifically to an amplification system to amplify the hybridization signals; these amplified signals can be visualized using a standard fluorescence microscope or imaging system. This system for example can detect and measure transcript levels in heterogeneous samples; for example, if a sample has normal and tumor cells present in the same tissue section. As mentioned, TaqMan probe-based gene expression analysis (PCR-based) can also be used for measuring gene expression levels in tissue samples, and for example for measuring mRNA levels in FFPE samples. In brief, TaqMan probe-based assays utilize a probe that hybridizes specifically to the mRNA target. This probe contains a quencher dye and a reporter dye (fluorescent molecule) attached to each end, and fluorescence is emitted only when specific hybridization to the mRNA target occurs. During the amplification step, the exonuclease activity of the polymerase enzyme causes the quencher and the reporter dyes to be detached from the probe, and fluorescence emission can occur. This fluorescence emission is recorded and signals are measured by a detection system, these signal intensities are used to calculate the abundance of a given transcript (gene expression) in a sample.

The term "sample" as used herein includes any biological specimen obtained from a patient. Samples include, without limitation, whole blood, plasma, serum, red blood cells, white blood cells (e.g., peripheral blood mononuclear cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by fine needle aspiration that is directed to a target, such as a tumor, or is random sampling of normal cells, such as periareolar), any other bodily fluid, a tissue sample (e.g., tumor tissue) such as a biopsy of a tumor (e.g., needle biopsy) or a lymph node (e.g., sentinel lymph node biopsy), and cellular extracts thereof. In some embodiments, the sample is whole blood or a fractional component thereof such as plasma, serum, or a cell pellet. In some embodiments, the sample is a formalin fixed paraffin embedded (FFPE) tumor tissue sample, e.g., from a solid tumor of the breast.

The term "altered" refers to a gene that is present at a detectably up-regulated or down-regulated level in a biological sample, e.g. plasma, from a patient with cancer, in comparison to a biological sample from a patient without cancer. The term includes increased or decreased expression in a sample from a patient with cancer due to transcription, post transcriptional processing, translation, post-translational processing, cellular localization (e.g, organelle, cytoplasm, nucleus, cell surface), and RNA and protein stability, as compared to a sample from a patient without cancer.

Altered expression can be 10%, 20%, 30%, 40%, 50%, 60%, 70%, 80%, 90% or more in comparison to a sample from a patient without cancer.

The terms "increased", "elevated", "overexpress", "overexpression", "overexpressed", "up-regulate", or "up-regulated" interchangeably refer to a gene that is present at a detectably greater level in a biological sample, e.g. plasma, from a patient with cancer, in comparison to a biological sample from a patient without cancer. The term includes overexpression in a sample from a patient with cancer due to transcription, post transcriptional processing, translation, post-translational processing, cellular localization (e.g, organelle, cytoplasm, nucleus, cell surface), and RNA and protein stability, as compared to a sample from a patient without cancer. Overexpression can be detected using conventional techniques for detecting mRNA (i.e., RT-PCR, PCR, hybridization) or proteins (i.e., ELISA, immunohistochemical techniques, mass spectroscopy, Luminex® xMAP technology). Overexpression can be 10%, 20%, 30%, 40%, 50%, 60%, 70%, 80%, 90% or more in comparison to a sample from a patient without cancer. In certain instances, overexpression is 1-fold, 2-fold, 3-fold, 4-fold 5, 6, 7, 8, 9, 10, or 15-fold or more higher levels of transcription or translation in comparison to a sample from a patient without cancer.

A "biopsy" refers to the process of removing a tissue sample for diagnostic or prognostic evaluation, and to the tissue specimen itself. Any biopsy technique known in the art can be applied to the methods and compositions of the present invention. The biopsy technique applied will generally depend on the tissue type to be evaluated and the size and type of the tumor (i.e., solid or suspended (i.e., blood or ascites)), among other factors. Representative biopsy techniques include excisional biopsy, incisional biopsy, needle biopsy (e.g., core needle biopsy, fine-needle aspiration biopsy, etc.), surgical biopsy, and bone marrow biopsy. Biopsy techniques are discussed, for example, in *Harrison's Principles of Internal Medicine*, Kasper, et al., eds., 16th ed., 2005, Chapter 70, and throughout Part V. One skilled in the art will appreciate that biopsy techniques can be performed to identify cancerous and/or precancerous cells in a given tissue sample.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

II. GENE SIGNATURES PREDICTIVE OF DRUG RESPONSE

Certain embodiments of the present disclosure provide a gene signature to predict sensitivity to drugs, including anti-cancer agents such as immune checkpoint inhibitors. Thus, some aspects concern the detection and quantification of certain genes in a sample. The replication stress response defect gene signature comprises a combination of genes disclosed in Tables 1A-B which are used to predict response to an immune checkpoint inhibitor. In some aspects, 3, 4, 5, 6, 7, 8, 9, 10, 11, 12, 13, 14, 15, 16, 17, 18, 19, 20, 25, 30, 40, 50, 75, 100, 125, 140 or more of the genes in Tables 1A-B are used to predict the response to immune checkpoint inhibition. The replication stress response defect signature genes can be normalized to reference genes.

TABLE 1A

Upregulated genes of RSR defect signature

| Gene | Coefficient |
|---|---|
| MMP1 | 6.019471 |
| CCND2 | 5.93647 |
| SERPINB2 | 5.885052 |
| FST | 5.54955 |
| DKK3 | 5.224194 |
| IL1B | 4.396991 |
| KRT6C | 4.114331 |
| KRT14 | 4.102242 |
| GJA1 | 3.887569 |
| PLCH2 | 3.800289 |
| IFITM3 | 3.573715 |
| RAB38 | 3.553869 |
| IL13RA2 | 3.538833 |
| HAS3 | 3.46251 |
| MMP10 | 3.432278 |
| DPYSL3 | 3.413787 |
| DLL1 | 3.411821 |
| FBN2 | 3.405745 |
| BCAT1 | 3.360753 |
| PKP1 | 3.338708 |
| MTAP | 3.282329 |
| WISP3 | 3.216913 |
| ARHGEF5L | 3.170899 |
| SOX7 | 3.148717 |
| PRSS3 | 3.109461 |
| ARTN | 3.103532 |
| NXN | 3.099611 |
| FOXA2 | 3.096642 |
| SLC2A6 | 3.077119 |
| FEZ1 | 3.028302 |
| C1orf24 | 3.025145 |
| LOC651397 | 3.024831 |
| ERAP2 | 3.016765 |
| SLC35E3 | 3.008624 |
| ADAM19 | 3.008512 |
| HMGA2 | 2.968392 |
| RTTN | 2.949358 |
| IGFBP7 | 2.94379 |
| MAOA | 2.927288 |
| LPAR1 | 2.874385 |
| NTM | 2.868449 |
| CNTNAP2 | 2.806813 |
| F2RL1 | 2.800321 |
| FGFBP1 | 2.767235 |
| IL24 | 2.752608 |
| CSF3 | 2.722458 |
| LOC375295 | 2.720158 |
| TUBB6 | 2.683939 |
| WNT7A | 2.659936 |
| SPARC | 2.648366 |
| FERMT1 | 2.579563 |
| RGS2 | 2.57331 |
| SLFN11 | 2.562791 |
| PRSS23 | 2.555394 |
| TMEM22 | 2.52707 |
| XRN2 | 2.52641 |
| MAMDC2 | 2.503511 |
| CYGB | 2.499611 |
| ZBED2 | 2.479938 |
| SNCA | 2.438847 |
| THBS1 | 2.433294 |
| SPHK1 | 2.433189 |
| IL1R2 | 2.432319 |
| FKBP11 | 2.425744 |
| NRG1 | 2.39527 |
| KRT6A | 2.395199 |
| FAM129A | 2.395101 |
| SNAI2 | 2.377021 |
| GPR81 | 2.358272 |
| SRPX | 2.352299 |
| CDKN2A | 2.333958 |
| TFPI2 | 2.303965 |
| LOC643272 | 2.266256 |
| TAGLN3 | 2.244207 |
| GADD45A | 2.232863 |
| PLAU | 2.231598 |

TABLE 1A-continued

Upregulated genes of RSR defect signature

| Gene | Coefficient |
|---|---|
| GSTT1 | 2.199645 |
| TNFRSF19 | 2.178832 |
| NIPAL4 | 2.178551 |
| ISG15 | 2.174197 |
| LIMA1 | 2.174186 |
| KCTD12 | 2.171146 |
| ARHGAP23 | 2.170546 |
| PARD6G | 2.164527 |
| AXL | 2.163405 |
| ENTPD3 | 2.156455 |
| HS3ST2 | 2.133284 |
| KRT5 | 2.129367 |
| SERPINB1 | 2.128476 |
| ANO1 | 2.123061 |
| IGFL1 | 2.101998 |
| MARCH4 | 2.067808 |
| RFTN1 | 2.065367 |
| LAMA3 | 2.065054 |
| KRT6B | 2.050765 |
| DLK2 | 2.045522 |
| SH2B3 | 2.044813 |
| AKAP12 | 2.043587 |
| JAG1 | 2.042345 |
| TMEM16A | 2.020356 |
| WBP5 | 2.009338 |
| TNFRSF6B | 2.00562 |
| ARMCX6 | 2.003583 |
| FLI1 | 1.981735 |
| LPXN | 1.981259 |
| MTSS1 | 1.98109 |
| HES2 | 1.968774 |
| RPS23 | 1.933447 |
| THY1 | 1.927411 |
| SH2D5 | 1.923847 |
| IRF6 | 1.913299 |
| MT1G | 1.893082 |
| IFIT1 | 1.890257 |
| FOSL1 | 1.882111 |
| SOCS2 | 1.874494 |
| HCLS1 | 1.870729 |
| NRCAM | 1.86534 |
| TP73L | 1.843815 |
| TNFRSF25 | 1.831165 |
| ANXA8L2 | 1.821696 |
| IL1A | 1.818907 |
| TPST1 | 1.817018 |
| MTE | 1.816999 |
| NLRP3 | 1.80551 |
| DKK1 | 1.802144 |
| TSPAN5 | 1.802028 |
| CSRP2 | 1.790166 |
| SLC31A2 | 1.776089 |
| KDELR3 | 1.772863 |
| HS3ST1 | 1.772319 |
| LOC100216001 | 1.758058 |
| FAT2 | 1.756199 |
| GNA15 | 1.753298 |
| CYP27B1 | 1.752217 |
| C20orf197 | 1.752074 |
| ARHGAP22 | 1.7424 |
| AFAP1L2 | 1.737032 |
| GALNT5 | 1.730968 |
| GRK5 | 1.725695 |
| RPS6KA4 | 1.72322 |
| SPAG1 | 1.712332 |
| ST3GAL5 | 1.710905 |
| CYR61 | 1.7076 |
| MMP9 | 1.70618 |
| TP63 | 1.706081 |
| UCA1 | 1.683253 |
| TMEM2 | 1.682553 |
| LOC729231 | 1.679654 |
| SNRPN | 1.675893 |
| S100A2 | 1.66266 |
| SYK | 1.646782 |
| COL17A1 | 1.644575 |
| LOC650517 | 1.642282 |
| TPX2 | 1.640368 |
| CTSC | 1.626639 |
| RNASE7 | 1.625552 |
| TINAGL1 | 1.616673 |
| ISG20 | 1.613448 |
| TGFA | 1.613063 |
| FRMD4A | 1.607639 |
| PTHLH | 1.605965 |
| PROCR | 1.593786 |
| PMCA | 1.592488 |
| TMEM156 | 1.587126 |
| SNRPB2 | 1.579954 |
| TMEM138 | 1.574576 |
| ADAMTS1 | 1.570079 |
| TRNP1 | 1.560684 |
| DUSP10 | 1.559847 |
| KRT17P3 | 1.553809 |
| CORO2A | 1.553267 |
| RIN2 | 1.55135 |
| SFTA1P | 1.546885 |
| CDKN2B | 1.546177 |
| APOBEC3F | 1.538322 |
| DFNA5 | 1.533359 |
| SERPINB13 | 1.532475 |
| KCNK6 | 1.530648 |
| TPST2 | 1.528636 |
| CTNNBL1 | 1.524766 |
| TBC1D2 | 1.52464 |
| SDHALP1 | 1.524579 |
| PCSK9 | 1.520311 |
| IL28RA | 1.511287 |
| LOC653110 | 1.506242 |
| SNURF | 1.505904 |
| LOC649679 | 1.501002 |
| SFN | 1.500489 |
| FAM92A1 | 1.497154 |
| SLC2A3 | 1.49592 |
| F2R | 1.49558 |
| LOC387882 | 1.491598 |
| GPR177 | 1.487828 |
| ETS2 | 1.483705 |
| CARD10 | 1.482656 |
| AUTS2 | 1.466928 |
| SLC2A9 | 1.463496 |
| DCBLD2 | 1.458504 |
| SHROOM2 | 1.453507 |
| ANXA8 | 1.45348 |
| CTNNAL1 | 1.450184 |
| RAP1BL | 1.450052 |
| LPAR3 | 1.449972 |
| TRQ1 | 1.443216 |
| LOC642489 | 1.443193 |
| C20orf1 | 1.443146 |
| LOC644330 | 1.441885 |
| NCRNA00153 | 1.439577 |
| RGS12 | 1.437145 |
| ARHGDIB | 1.430884 |
| SRC | 1.428541 |
| CDCA4 | 1.422409 |
| F2F7 | 1.420966 |
| FOXD1 | 1.418161 |
| MYLK | 1.405612 |
| C3orf54 | 1.403175 |
| CMTM7 | 1.402138 |
| IF1T2 | 1.396914 |
| NUDT11 | 1.39579 |
| YWHAB | 1.390412 |
| APOBEC3G | 1.38923 |
| PRNP | 1.388798 |
| SPG3A | 1.384809 |
| KCNG1 | 1.382611 |
| PABPC1L | 1.380346 |
| COL7A1 | 1.378739 |
| TCEAL8 | 1.377184 |
| FKBP1A | 1.372332 |

TABLE 1A-continued

Upregulated genes of RSR defect signature

| Gene | Coefficient |
| --- | --- |
| DLL3 | 1.371813 |
| RRBP1 | 1.363304 |
| MT1X | 1.36282 |
| WDFY2 | 1.362819 |
| PRSS2 | 1.35413 |
| EFNB1 | 1.350366 |
| ARID3B | 1.34769 |
| ANXA10 | 1.341338 |
| LYPD5 | 1.335533 |
| AURKA | 1.334783 |
| PAK6 | 1.334227 |
| MAP1B | 1.330741 |
| ST6GALNAC5 | 1.318445 |
| TPM3 | 1.318277 |
| ABCC4 | 1.311929 |
| ANXA8L1 | 1.307339 |
| NXT1 | 1.307091 |
| IL1RAP | 1.304748 |
| HRAS | 1.303749 |
| DNTTIP1 | 1.302808 |
| ITGA2 | 1.302623 |
| MT1F | 1.302508 |
| UBE2C | 1.301651 |
| CNTN1 | 1.300993 |
| LOC652846 | 1.300709 |
| TUBB4Q | 1.299965 |
| PGM3 | 1.298008 |
| CAPRIN2 | 1.297493 |
| LOC654121 | 1.290621 |
| GOSR2 | 1.2901 |
| SOX15 | 1.289995 |
| TUBB2A | 1.284012 |
| C12orf31 | 1.284 |
| C12orf54 | 1.281208 |
| ANTXR2 | 1.277199 |
| CSE1L | 1.275074 |
| PVRL3 | 1.274872 |
| RAE1 | 1.272764 |
| PRKCDBP | 1.27198 |
| P2RY2 | 1.265976 |
| HOXC4 | 1.264948 |
| CCNA1 | 1.264257 |
| PPP4R4 | 1.257978 |
| ZFP64 | 1.25768 |
| RGS20 | 1.25606 |
| BTBD11 | 1.254448 |
| TSPAN18 | 1.252191 |

TABLE 1B

Down regulated genes of RSR defect signature

| Gene | Coefficient |
| --- | --- |
| SIDT2 | −1.25007 |
| DNAJB12 | −1.25065 |
| KCTD20 | −1.25263 |
| ELL3 | −1.25348 |
| LOC283953 | −1.2536 |
| SLC27A5 | −1.25781 |
| SLC6A14 | −1.25841 |
| PPP2R2C | −1.25868 |
| ART3 | −1.2595 |
| TRIB1 | −1.26411 |
| NPEPL1 | −1.26705 |
| TMEM205 | −1.2746 |
| NOL3 | −1.27632 |
| LOG649853 | −1.27803 |
| LOC388588 | −1.27826 |
| NUCB1 | −1.27902 |
| BTG1 | −1.28816 |
| ID2 | −1.29302 |
| FER1L4 | −1.29718 |
| LOC146439 | −1.29791 |
| IL20RB | −1.29806 |
| FAM195A | −1.30093 |
| CEBPD | −1.30202 |
| RAB40B | −1.30453 |
| NFIC | −1.30759 |
| MAPK3 | −1.30947 |
| EVPL | −1.31087 |
| KLRC2 | −1.31287 |
| PIR | −1.31349 |
| BCMO1 | −1.31372 |
| ALDH3A2 | −1.31677 |
| LOC729660 | −1.31814 |
| GSTZ1 | −1.32226 |
| SPOCK1 | −1.32435 |
| CD36 | −1.32535 |
| NICN1 | −1.33054 |
| PDPK1 | −1.33158 |
| TNFAIP6 | −1.33301 |
| ACAA2 | −1.33487 |
| MGST2 | −1.33566 |
| OXR1 | −1.33718 |
| KIAA1370 | −1.33719 |
| TFPI | −1.33741 |
| IL17C | −1.33764 |
| G6PD | −1.33881 |
| SEPX1 | −1.34385 |
| LOC653778 | −1.34467 |
| PEG10 | −1.34528 |
| UBR5 | −1.34561 |
| LOC653924 | −1.34856 |
| HBP1 | −1.34984 |
| NOX5 | −1.35426 |
| RRM2B | −1.358 |
| ZFPM1 | −1.35856 |
| XIST | −1.35876 |
| ACY1 | −1.35882 |
| MFSD3 | −1.35928 |
| METRNL | −1.35963 |
| SOD2 | −1.36743 |
| VAV3 | −1.36936 |
| SLC16A4 | −1.37005 |
| LOC653506 | −1.37036 |
| LOG147645 | −1.37169 |
| PON2 | −1.37746 |
| ACTA2 | −1.38027 |
| LOX | −1.38235 |
| PDGFC | −1.38447 |
| CRIP1 | −1.38924 |
| PCSK5 | −1.38962 |
| CCNG2 | −1.3897 |
| NEBL | −1.39751 |
| KLK6 | −1.398 |
| SETD6 | −1.3981 |
| PTPN22 | −1.3984 |
| ACOX2 | −1.39885 |
| SLC9A3R1 | −1.40058 |
| C4orf34 | −1.40116 |
| RICS | −1.40623 |
| GSTK1 | −1.4075 |
| GLB1L2 | −1.40891 |
| LOC100133511 | −1.41155 |
| MGST1 | −1.41196 |
| PTGES | −1.41296 |
| ITM2C | −1.41403 |
| KHDRBS3 | −1.41537 |
| NET1 | −1.41847 |
| BCKDHA | −1.42357 |
| NR4A2 | −1.42427 |
| SLC16A14 | −1.42641 |
| SERPINB4 | −1.429 |
| GPR110 | −1.43474 |
| CDC42EP4 | −1.43504 |
| GRTP1 | −1.43714 |
| ETFDH | −1.43715 |
| BIN1 | −1.43906 |

TABLE 1B-continued

Down regulated genes of RSR defect signature

| Gene | Coefficient |
|---|---|
| CYP1A1 | −1.43934 |
| ST6GAL1 | −1.44063 |
| ABLIM3 | −1.44208 |
| KDELC2 | −1.44434 |
| SEMA3C | −1.44886 |
| MGC42367 | −1.44968 |
| PAM | −1.45086 |
| NME3 | −1.45115 |
| DPP7 | −1.45409 |
| C10orf59 | −1.45428 |
| C12orf36 | −1.45914 |
| TMC4 | −1.47052 |
| TM7SF2 | −1.47376 |
| NUP210 | −1.47649 |
| APRT | −1.47851 |
| MYEOV | −1.48136 |
| LIPK | −1.4912 |
| LOC93622 | −1.49419 |
| WNT5A | −1.49525 |
| TMEM187 | −1.49608 |
| MEST | −1.49909 |
| LOC285095 | −1.5005 |
| MFI2 | −1.50193 |
| HIST1H1C | −1.50375 |
| LOC654103 | −1.50543 |
| LOC387825 | −1.50814 |
| TMPRSS3 | −1.50888 |
| LOC646836 | −1.51307 |
| MANSC1 | −1.52117 |
| FAP | −1.5243 |
| HCFC1R1 | −1.52574 |
| FERMT2 | −1.52861 |
| FARP1 | −1.52956 |
| LOC729985 | −1.53115 |
| FLJ12684 | −1.5312 |
| ALDH5A1 | −1.53574 |
| TIMP2 | −1.53806 |
| BNIP3L | −1.54089 |
| TRIM4 | −1.54198 |
| CELSR3 | −1.54238 |
| LOC651524 | −1.54382 |
| NLGN4X | −1.5456 |
| GCNT3 | −1.54835 |
| TSKU | −1.55336 |
| P4HTM | −1.55544 |
| ZFP90 | −1.56052 |
| SPESP1 | −1.56284 |
| BSPRY | −1.56344 |
| SHRM | −1.56387 |
| CST6 | −1.56442 |
| TBL1X | −1.56447 |
| KRT80 | −1.56879 |
| AMFR | −1.57152 |
| OKL38 | −1.5756 |
| YPEL3 | −1.58033 |
| CLCN3 | −1.58649 |
| FLJ20273 | −1.58983 |
| SLITRK6 | −1.59738 |
| GLRB | −1.59833 |
| SEMA6A | −1.5986 |
| UGT1A6 | −1.60479 |
| LUM | −1.60891 |
| TRAPPC6A | −1.6092 |
| SULT1A1 | −1.60981 |
| LOC441453 | −1.61079 |
| LOC653061 | −1.61277 |
| ITFG1 | −1.62202 |
| ETFB | −1.63119 |
| RPL34 | −1.63597 |
| KIAA1147 | −1.63654 |
| HMGCS2 | −1.63656 |
| FTHL3 | −1.64381 |
| PLAC8 | −1.64552 |
| NIPSNAP1 | −1.64713 |
| UBE2D4 | −1.64886 |
| DDIT4L | −1.65098 |
| ASMTL | −1.65632 |
| VGF | −1.66481 |
| ZNF428 | −1.66544 |
| LOC440160 | −1.66704 |
| DECR1 | −1.66811 |
| SCARNA9 | −1.66951 |
| SERPINB3 | −1.67437 |
| LGALS7B | −1.68528 |
| GLS | −1.68902 |
| ANGPT1 | −1.704 |
| ITFG3 | −1.70719 |
| HOXA5 | −1.70834 |
| GABRE | −1.70939 |
| RNF165 | −1.7099 |
| SQSTM1 | −1.71899 |
| CBX2 | −1.72371 |
| FTHL11 | −1.74438 |
| EBP1 | −1.75212 |
| VASN | −1.75452 |
| MFSD1 | −1.75598 |
| GCHFR | −1.76571 |
| CYB5A | −1.77086 |
| LRP3 | −1.77265 |
| TMEM139 | −1.77424 |
| F12 | −1.77727 |
| C3 | −1.77809 |
| LOC643911 | −1.78763 |
| TEAD2 | −1.78829 |
| AKR1B1 | −1.78836 |
| TRIB2 | −1.79424 |
| TLR1 | −1.80311 |
| METTL7A | −1.80347 |
| CD163L1 | −1.80455 |
| RERG | −1.81006 |
| OSGIN2 | −1.81439 |
| SLC22A18 | −1.82168 |
| PPARG | −1.82285 |
| FTHL2 | −1.82637 |
| LY6E | −1.82718 |
| FBLN1 | −1.82782 |
| ARID5B | −1.8289 |
| SHROOM3 | −1.83179 |
| PADI4 | −1.83589 |
| ABCB6 | −1.83635 |
| CLDN8 | −1.8376 |
| SNCAIP | −1.83774 |
| C5orf46 | −1.8471 |
| TMEM45A | −1.84728 |
| PTPN20 | −1.85106 |
| ERBB3 | −1.85619 |
| LYPD3 | −1.85928 |
| IRX3 | −1.86622 |
| SEL1L3 | −1.87413 |
| PCOLCE2 | −1.87471 |
| LOC441282 | −1.8812 |
| PGD | −1.88669 |
| SLC39A8 | −1.88679 |
| TJP3 | −1.88746 |
| TMEM42 | −1.88848 |
| KCNIP3 | −1.88867 |
| CEACAM1 | −1.89099 |
| PLCXD3 | −1.90111 |
| ARSD | −1.90231 |
| LAGE3 | −1.90523 |
| S100A9 | −1.90548 |
| RAP1GAP | −1.91105 |
| PPAP2B | −1.91753 |
| CXADR | −1.91756 |
| CYFIP2 | −1.91973 |
| LOC100129195 | −1.93231 |
| HTATIP2 | −1.93582 |
| GDF15 | −1.94914 |
| FTHL16 | −1.94982 |
| CLCA2 | −1.96034 |
| CTSD | −1.96637 |
| MAFB | −1.9667 |

TABLE 1B-continued

Down regulated genes of RSR defect signature

| Gene | Coefficient |
|---|---|
| GPRC5C | −1.96853 |
| ELF3 | −1.98312 |
| PDE4B | −1.99356 |
| ROS1 | −1.99357 |
| CA2 | −1.99624 |
| CKLF | −2.00374 |
| SYTL2 | −2.00876 |
| LOC652669 | −2.00877 |
| D2HGDH | −2.00988 |
| ZNF323 | −2.02361 |
| PINK1 | −2.02562 |
| P8 | −2.03177 |
| HSPBL2 | −2.0376 |
| PLXDC2 | −2.04194 |
| ALDH3B1 | −2.04483 |
| SRGN | −2.05321 |
| EGFLAM | −2.05335 |
| TRIM2 | −2.05481 |
| RBM47 | −2.05675 |
| RPL28 | −2.06101 |
| TNFAIP2 | −2.06307 |
| MXD4 | −2.06512 |
| DECR2 | −2.067 |
| TSTD1 | −2.0696 |
| PTK6 | −2.07171 |
| LPL | −2.07483 |
| GCLC | −2.07579 |
| CXCR7 | −2.07754 |
| STC1 | −2.07758 |
| KRT15 | −2.08545 |
| NOTCH3 | −2.09072 |
| LOC645553 | −2.09675 |
| CD97 | −2.09813 |
| RAB26 | −2.11208 |
| CYBRD1 | −2.1122 |
| KIAA0182 | −2.11686 |
| RPS29 | −2.11973 |
| S100A8 | −2.12337 |
| LOC341230 | −2.12426 |
| FBXL16 | −2.1345 |
| KLK5 | −2.14707 |
| NCOA7 | −2.15121 |
| LOC642567 | −2.15887 |
| CYP4F3 | −2.16983 |
| PPAP2C | −2.18057 |
| ATP6V1B1 | −2.18671 |
| LOC653879 | −2.1886 |
| COL8A1 | −2.18988 |
| TNFSF9 | −2.19233 |
| NAT14 | −2.19731 |
| TNS3 | −2.19903 |
| AIF1L | −2.20592 |
| GPNMB | −2.20791 |
| FBXO32 | −2.22136 |
| HS6ST2 | −2.22216 |
| GNE | −2.23163 |
| IL6 | −2.23938 |
| ARL14 | −2.24761 |
| FLJ10916 | −2.2482 |
| LOC642399 | −2.25312 |
| LOC392437 | −2.25492 |
| NQO1 | −2.26476 |
| ECH1 | −2.26508 |
| ECHDC3 | −2.27512 |
| DENND2D | −2.28753 |
| FAM113B | −2.3119 |
| LOC340274 | −2.31309 |
| ANKRD33 | −2.3134 |
| CITED2 | −2.31488 |
| ICA1 | −2.32352 |
| FXYD3 | −2.32445 |
| CHDH | −2.33027 |
| COBL | −2.34943 |
| LOC392871 | −2.35532 |
| NINJ1 | −2.36078 |
| NAMPT | −2.36398 |
| LOC255326 | −2.36684 |
| NUPR1 | −2.38559 |
| CHURC1 | −2.40718 |
| CSGALNACT1 | −2.42362 |
| KRT24 | −2.42874 |
| HOXA10 | −2.42907 |
| DCN | −2.43486 |
| FGF2 | −2.44874 |
| WFDC2 | −2.47232 |
| BAMBI | −2.4731 |
| LXN | −2.47583 |
| PNLIPRP3 | −2.47676 |
| CLDN1 | −2.49263 |
| TAGLN | −2.4939 |
| ZDHHC4 | −2.50564 |
| GRB14 | −2.50864 |
| NMB | −2.52317 |
| SERPINE2 | −2.5253 |
| CYP24A1 | −2.52793 |
| FLJ39632 | −2.5382 |
| IMPA2 | −2.54024 |
| CTSH | −2.54169 |
| TNFRSF11B | −2.54174 |
| NCCRP1 | −2.5676 |
| FTH1 | −2.57333 |
| CPVL | −2.59237 |
| DIO2 | −2.59289 |
| EPHX1 | −2.60114 |
| ABCC2 | −2.61024 |
| SGPP2 | −2.61584 |
| DBNDD1 | −2.6264 |
| PDK4 | −2.6418 |
| AZGP1 | −2.64587 |
| CRABP2 | −2.65469 |
| IRX5 | −2.66835 |
| LEMD1 | −2.67905 |
| CD14 | −2.69071 |
| CHCHD10 | −2.71103 |
| CTXN1 | −2.71849 |
| CLIC3 | −2.72086 |
| ASS1 | −2.72177 |
| LOC642477 | −2.72528 |
| C15orf48 | −2.75697 |
| USMG5 | −2.76448 |
| TXNIP | −2.77737 |
| LCP1 | −2.80254 |
| C19orf46 | −2.80483 |
| KRTCAP3 | −2.80668 |
| PDZK1IP1 | −2.82218 |
| ITGB2 | −2.82404 |
| BGN | −2.8352 |
| LOC146909 | −2.84129 |
| C14orf147 | −2.86793 |
| ACSL1 | −2.87582 |
| SLC16A5 | −2.88693 |
| LOC100131139 | −2.88792 |
| ATP6V0E2 | −2.92823 |
| BCL6 | −2.94233 |
| BAIAP2L2 | −2.95783 |
| LOC400879 | −2.96268 |
| LAPTM4B | −2.99261 |
| LCN2 | −3.00429 |
| GBP2 | −3.0049 |
| M160 | −3.0522 |
| NME4 | −3.0784 |
| CCL20 | −3.11266 |
| CFD | −3.14784 |
| MARCKSL1 | −3.15445 |
| ECGF1 | −3.17279 |
| AKR1C2 | −3.18726 |
| CES1 | −3.21532 |
| CYP4X1 | −3.21604 |
| CA9 | −3.27981 |
| FABP4 | −3.30851 |
| FAM46A | −3.3574 |
| QPCT | −3.43044 |

TABLE 1B-continued

Down regulated genes of RSR defect signature

| Gene | Coefficient |
|---|---|
| ANPEP | −3.4683 |
| GDPD3 | −3.55358 |
| LMTK3 | −3.55399 |
| EPDR1 | −3.58645 |
| PAPPA | −3.59478 |
| CD70 | −3.63127 |
| HOXA9 | −3.67879 |
| C1QTNF1 | −3.68801 |
| PSCA | −3.69377 |
| DEFB1 | −3.70137 |
| HRASLS3 | −3.70468 |
| CXXC5 | −3.73906 |
| LOC645638 | −3.74009 |
| AKR1B15 | −3.74711 |
| KYNU | −3.8076 |
| AKR1C4 | −3.84358 |
| REPIN1 | −3.85231 |
| COX7A1 | −3.87248 |
| CFB | −3.91693 |
| ABCC3 | −3.99835 |
| AKR1C3 | −4.01752 |
| LOC100134265 | −4.05549 |
| CYP1B1 | −4.07481 |
| S100P | −4.22853 |
| TCN1 | −4.2988 |
| AKR1B10 | −4.30839 |
| MGP | −4.3921 |
| CALB2 | −4.45378 |
| SERPINA3 | −4.47358 |
| MUC1 | −4.50468 |
| S100A7 | −4.54208 |
| ALDH3A1 | −4.63814 |
| MSLN | −5.11429 |
| S100A4 | −5.1996 |
| IGFBP3 | −5.38355 |
| RARRES1 | −5.90473 |
| CYBA | −6.16047 |

A. Isolation of RNA

Aspects of the present disclosure concern the isolation of RNA from a patient sample for use in determining the expression level of a drug sensitivity gene signature, such as an immune checkpoint inhibitor signature. The patient sample may blood, saliva, urine, or a tissue biopsy. The tissue biopsy may be a tumor biopsy that has been flash-frozen (e.g., in liquid nitrogen), formalin-fixed and paraffin-embedded (FFPE), and/or preserved by an RNA stabilization agent (e.g., RNAlater®). In some aspects, isolation is not necessary, and the assay directly utilizes RNA from within a homogenate of the tissue sample. In certain aspects the homogenate of FFPE tumor sample is enzymatically digested.

RNA may be isolated using techniques well known to those of skill in the art. Methods generally involve lysing the cells with a chaotropic agent (e.g., guanidinium isothiocyanate) and/or detergent (e.g., N-lauroyl sarcosine) prior to implementing processes for isolating particular populations of RNA. Chromatography is a process often used to separate or isolate nucleic acids from protein or from other nucleic acids. Such methods can involve electrophoresis with a gel matrix, filter columns, coated magnetic beads, alcohol precipitation, and/or other chromatography.

B. Expression Assessment

In certain aspects, methods of the present disclosure concern measuring expression of replication stress response defect signature genes as well as one or more reference genes in a sample from a subject with cancer, such as breast cancer, ovarian cancer, kidney cancer, melanoma, bladder cancer, stomach cancer, or glioblastoma. The expression information may be obtained by testing cancer samples by a lab, a technician, a device, or a clinician. In a certain embodiment, the differential expression of one or more genes selected from those of Tables 1A-B may be measured.

Expression levels of the genes can be detected using any suitable means known in the art. For example, detection of gene expression can be accomplished by detecting nucleic acid molecules (such as RNA) using nucleic acid amplification methods (such as RT-PCR, droplet-based RT amplification, exon capture of RNA sequence library, next generation RNA sequencing), array analysis (such as microarray analysis), or hybridization methods (such as ribonuclease protection assay, bead-based assays, or Nanostring®). Detection of gene expression can also be accomplished using assays that detect the proteins encoded by the genes, including immunoassays (such as ELISA, Western blot, RIA assay, or protein arrays).

The pattern or signature of expression in each cancer sample may then be used to generate a cancer prognosis or classification, such as predicting cancer survival or recurrence, using the replication stress response defect gene signature. The expression of one or more of the replication stress response defect signature genes could be assessed to predict or report prognosis or prescribe treatment options for cancer patients, especially breast cancer patients.

The expression of one or more of the genes may be measured by a variety of techniques that are well known in the art. Quantifying the levels of the messenger RNA (mRNA) of a gene may be used to measure the expression of the gene. Alternatively, quantifying the levels of the protein product of replication stress response defect-related genes may be to measure the expression of the genes. Additional information regarding the methods discussed below may be found in Ausubel et al., (2003) Current Protocols in Molecular Biology, John Wiley & Sons, New York, NY, or Sambrook et al. (1989) Molecular Cloning: A Laboratory Manual, Cold Spring Harbor Press, Cold Spring Harbor, NY. One skilled in the art will know which parameters may be manipulated to optimize detection of the mRNA or protein of interest.

A nucleic acid microarray may be used to quantify the differential expression of a plurality of genes. Microarray analysis may be performed using commercially available equipment, following manufacturer's protocols, such as by using the Affymetrix GeneChip® technology (Santa Clara, CA) or the Microarray System from Incyte (Fremont, CA). Typically, single-stranded nucleic acids (e.g., cDNAs or oligonucleotides) are plated, or arrayed, on a microchip substrate. The arrayed sequences are then hybridized with specific nucleic acid probes from the cells of interest. Fluorescently labeled cDNA probes may be generated through incorporation of fluorescently labeled deoxynucleotides by reverse transcription of RNA extracted from the cells of interest. Alternatively, the RNA may be amplified by in vitro transcription and labeled with a marker, such as biotin. The labeled probes are then hybridized to the immobilized nucleic acids on the microchip under highly stringent conditions. After stringent washing to remove the non-specifically bound probes, the chip is scanned by confocal laser microscopy or by another detection method, such as a CCD camera. The raw fluorescence intensity data in the hybridization files are generally preprocessed with a robust statistical normalization algorithm to generate expression values.

Quantitative real-time PCR (qRT-PCR) may also be used to measure the differential expression of a plurality of genes.

In qRT-PCR, the RNA template is generally reverse transcribed into cDNA, which is then amplified via a PCR reaction. The amount of PCR product is followed cycle-by-cycle in real time, which allows for determination of the initial concentrations of mRNA. To measure the amount of PCR product, the reaction may be performed in the presence of a fluorescent dye, such as SYBR Green, which binds to double-stranded DNA. The reaction may also be performed with a fluorescent reporter probe that is specific for the DNA being amplified.

For example, extracted RNA can be reverse-transcribed using a GeneAmp® RNA PCR kit (Perkin Elmer, Calif., USA), following the manufacturer's instructions. In some embodiments, gene expression levels can be determined using a gene expression analysis technology that measure mRNA in solution. Methods of detecting gene expression are described for example in U.S. Patent Application Nos. US20140357660, and US20130259858; incorporated herein by reference. Examples of such gene expression analysis technologies include, but not limited to RNAscope™, RT-PCR, Nanostring®, QuantiGene®, gNPA®, HTG®, microarray, and sequencing. For example, methods of Nanostring use labeled reporter molecules, referred to as labeled "nanoreporters," that are capable of binding individual target molecules. Through the nanoreporters' label codes, the binding of the nanoreporters to target molecules results in the identification of the target molecules. Methods of Nanostring are described in U.S. Pat. No. 7,473,767 (see also, Geiss et al., 2008). Methods may include the RainDance droplet amplification method such as described in U.S. Pat. No. 8,535,889, incorporated herein by reference. Sequencing may include exon capture, such as Illumina targeted sequencing after the generation of a tagged library for next generation sequencing (e.g. described in International Patent Application No. WO2013131962, incorporated herein by reference).

A non-limiting example of a fluorescent reporter probe is a TaqMan® probe (Applied Biosystems, Foster City, CA). The fluorescent reporter probe fluoresces when the quencher is removed during the PCR extension cycle. Multiplex qRT-PCR may be performed by using multiple gene-specific reporter probes, each of which contains a different fluorophore. Fluorescence values are recorded during each cycle and represent the amount of product amplified to that point in the amplification reaction. To minimize errors and reduce any sample-to-sample variation, qRT-PCR is typically performed using a reference standard. The ideal reference standard is expressed at a constant level among different tissues, and is unaffected by the experimental treatment. The system can include a thermocycler, laser, charge-coupled device (CCD) camera, and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

To minimize errors and the effect of sample-to-sample variation, RT-PCR can be performed using an internal standard. The ideal internal standard is expressed at a constant level among different tissues, and is unaffected by an experimental treatment. RNAs commonly used to normalize patterns of gene expression are mRNAs for the housekeeping genes GAPDH, β-actin, and 18S ribosomal RNA.

A variation of RT-PCR is real time quantitative RT-PCR, which measures PCR product accumulation through a dual-labeled fluorogenic probe (e.g., TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Heid et al., 1996). Quantitative PCR is also described in U.S. Pat. No. 5,538,848. Related probes and quantitative amplification procedures are described in U.S. Pat. Nos. 5,716,784 and 5,723,591. Instruments for carrying out quantitative PCR in microtiter plates are available from PE Applied Biosystems (Foster City, CA).

The steps of a representative protocol for quantitating gene expression level using fixed, paraffin-embedded tissues as the RNA source, including mRNA isolation, purification, primer extension and amplification are given in various published journal articles (see Godfrey et al., 2000; Specht et al., 2001). Briefly, a representative process starts with cutting about 10μm thick sections of paraffin-embedded neoplasm tissue samples or adjacent non-cancerous tissue. The RNA is then extracted, and protein and DNA are removed. Alternatively, RNA is isolated directly from a neoplasm sample or other tissue sample. After analysis of the RNA concentration, RNA repair and/or amplification steps can be included, if necessary, and RNA is reverse transcribed using gene specific primers, followed by preparation of a tagged RNA sequencing library, and paired-end sequencing. In another example, the RNA is not reverse transcribed, but is directly hybridized to a specific template and then labeled with oligonucleotides and/or chemical or fluorescent color to be detected and counted by a laser.

Immunohistochemical staining may also be used to measure the differential expression of a plurality genes. This method enables the localization of a protein in the cells of a tissue section by interaction of the protein with a specific antibody. For this, the tissue may be fixed in formaldehyde or another suitable fixative, embedded in wax or plastic, and cut into thin sections (from about 0.1 mm to several mm thick) using a microtome. Alternatively, the tissue may be frozen and cut into thin sections using a cryostat. The sections of tissue may be arrayed onto and affixed to a solid surface (i.e., a tissue microarray). The sections of tissue are incubated with a primary antibody against the antigen of interest, followed by washes to remove the unbound antibodies. The primary antibody may be coupled to a detection system, or the primary antibody may be detected with a secondary antibody that is coupled to a detection system. The detection system may be a fluorophore or it may be an enzyme, such as horseradish peroxidase or alkaline phosphatase, which can convert a substrate into a colorimetric, fluorescent, or chemiluminescent product. The stained tissue sections are generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for the gene.

An enzyme-linked immunosorbent assay, or ELISA, may be used to measure the differential expression of a plurality of genes. There are many variations of an ELISA assay. All are based on the immobilization of an antigen or antibody on a solid surface, generally a microtiter plate. The original ELISA method comprises preparing a sample containing the proteins of interest, coating the wells of a microtiter plate with the sample, incubating each well with a primary antibody that recognizes a specific antigen, washing away the unbound antibody, and then detecting the antibody-antigen complexes. The antibody-antibody complexes may be detected directly. For this, the primary antibodies are conjugated to a detection system, such as an enzyme that produces a detectable product. The antibody-antibody complexes may be detected indirectly. For this, the primary antibody is detected by a secondary antibody that is conjugated to a detection system, as described above. The microtiter plate is then scanned and the raw intensity data may be converted into expression values using means known in the art.

An antibody microarray may also be used to measure the differential expression of a plurality of genes. For this, a plurality of antibodies is arrayed and covalently attached to the surface of the microarray or biochip. A protein extract containing the proteins of interest is generally labeled with a fluorescent dye.

The labeled proteins may be incubated with the antibody microarray. After washes to remove the unbound proteins, the microarray is scanned. The raw fluorescent intensity data may be converted into expression values using means known in the art.

Luminex multiplexing microspheres may also be used to measure the differential expression of a plurality of genes. These microscopic polystyrene beads are internally color-coded with fluorescent dyes, such that each bead has a unique spectral signature (of which there are up to 100). Beads with the same signature are tagged with a specific oligonucleotide or specific antibody that will bind the target of interest (i.e., mRNA or protein, respectively). The target, in turn, is also tagged with a fluorescent reporter. Hence, there are two sources of color, one from the bead and the other from the reporter molecule on the target. The beads are then incubated with the sample containing the targets, of which up 100 may be detected in one well. The small size/surface area of the beads and the three dimensional exposure of the beads to the targets allows for nearly solution-phase kinetics during the binding reaction. The captured targets are detected by high-tech fluidics based upon flow cytometry in which lasers excite the internal dyes that identify each bead and also any reporter dye captured during the assay. The data from the acquisition files may be converted into expression values using means known in the art.

In situ hybridization may also be used to measure the differential expression of a plurality of genes. This method permits the localization of mRNAs of interest in the cells of a tissue section. For this method, the tissue may be frozen, or fixed and embedded, and then cut into thin sections, which are arrayed and affixed on a solid surface. The tissue sections are incubated with a labeled antisense probe that will hybridize with an mRNA of interest. The hybridization and washing steps are generally performed under highly stringent conditions. The probe may be labeled with a fluorophore or a small tag (such as biotin or digoxigenin) that may be detected by another protein or antibody, such that the labeled hybrid may be detected and visualized under a microscope. Multiple mRNAs may be detected simultaneously, provided each antisense probe has a distinguishable label. The hybridized tissue array is generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for each gene.

C. Methods of Use

Aspects of the present disclosure include methods for predicting the response of cancer in a subject to an anti-cancer agent by, for example, obtaining cell or tissue samples from a subject and assessing such samples for the presence of altered expression of the genes in the drug response signature provided herein. As used herein, the term "cancer" refers to an uncontrolled growth of cells that may interfere with the normal functioning of the bodily organs and systems, and includes both primary and metastatic tumors. Primary tumors or cancers that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject.

Cancers include, but are not limited to, basal cell carcinoma, biliary tract cancer; bladder cancer; bone cancer; brain and CNS cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; glioblastoma; intra-epithelial neoplasm; kidney cancer; larynx cancer; leukemia, liver cancer; lung cancer (e.g. small cell and non-small cell); lymphoma including Hodgkin's and Non-Hodgkin's lymphoma; melanoma, myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas. In particular embodiments, a subject who is diagnosed or treated by the present methods, is a subject with breast cancer or ovarian cancer.

The methods described herein can be used to screen patients for response to certain anti-cancer agents, such as immune checkpoint inhibitors. The methods described herein can be used alone, or in conjunction with other tests. In general, microarray analysis is performed on a plasma sample, a tissue sample, or isolated exosomes, and the altered expression of the gene signature is determined by measuring either mRNA or protein levels. Patients that have altered expression of signature genes receive appropriate treatment.

III. METHODS OF TREATING

Certain aspects of the present disclosure can be used to identify, delay progression and/or treat a disease or disorder, such as cancer, based on the presence of a gene signature provided herein. Other aspects of the present disclosure provide for sensitizing a subject with cancer to treatment with immune checkpoint inhibitors, for example, by administering DNA damage checkpoint inhibitors.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect. A tissue, tumor, or cell can be contacted with one or more compositions or pharmacological formulation(s) comprising one or more of the agents, or by contacting the tissue, tumor, and/or cell with two or more distinct compositions or formulations. Also, it is contemplated that such a combination therapy can be used in conjunction with chemotherapy, radiotherapy, surgical therapy, or immunotherapy.

The methods described herein are useful in treating cancer, particularly, replication stress response deficient cancer. More specifically, cancers that are treated using any one or more immune checkpoint inhibitors, or variants thereof, and in connection with the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer (including clear cell renal cell carcinoma), prostate cancer, vulval cancer, thyroid cancer, various types of head and neck cancer, melanoma, superficial spreading melanoma, lentigo maligna melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

An effective response of a patient or a patient's "responsiveness" to treatment refers to the clinical or therapeutic benefit imparted to a patient at risk for, or suffering from, a disease or disorder. Such benefit may include cellular or biological responses, a complete response, a partial response, a stable disease (without progression or relapse), or a response with a later relapse. For example, an effective response can be reduced tumor size or progression-free survival in a patient diagnosed with cancer.

Regarding neoplastic condition treatment, depending on the stage of the neoplastic condition, neoplastic condition treatment involves one or a combination of the following therapies: surgery to remove the neoplastic tissue, radiation therapy, and chemotherapy. Other therapeutic regimens may be combined with the administration of the anticancer agents, e.g., therapeutic compositions and chemotherapeutic agents. For example, the patient to be treated with such anti-cancer agents may also receive radiation therapy and/or may undergo surgery.

For the prevention or treatment of disease, the appropriate dosage of a therapeutic composition, e.g., an immune checkpoint inhibitor, will depend on the type of disease to be treated, as defined above, the severity and course of the disease, whether the agent is administered for preventive or therapeutic purposes, previous therapy, the patient's clinical history and response to the agent, and the discretion of the physician. The agent is suitably administered to the patient at one time or over a series of treatments.

A. Pharmaceutical Compositions

Also provided herein are pharmaceutical compositions and formulations comprising an immune checkpoint inhibitor, optionally an additional anti-cancer agent, and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22nd edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn— protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

B. Combination Treatments

The methods and compositions, including combination therapies, enhance the therapeutic or protective effect, and/or increase the therapeutic effect of another anti-cancer or anti-hyperproliferative therapy. The additional therapy may be radiation therapy, surgery (e.g., lumpectomy and a mastectomy), chemotherapy, targeted molecular inhibitor, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant, neoadjuvant, or palliative therapy. Examples of combination treatments, include, for example, a PD-L1 inhibitor (e.g., atezolizumab) with a VEGF inhibitor (e.g., bevacizumab) or a DNA damage checkpoint inhibitor with an immune checkpoint inhibitor.

Therapeutic and prophylactic methods and compositions can be provided in a combined amount effective to achieve the desired effect, such as the killing of a cancer cell and/or the inhibition of cellular hyperproliferation. A tissue, tumor, or cell can be contacted with one or more compositions or pharmacological formulation(s) comprising one or more of the agents or by contacting the tissue, tumor, and/or cell with two or more distinct compositions or formulations. Also, it is contemplated that such a combination therapy can be used in conjunction with radiotherapy, surgical therapy, or immunotherapy.

Administration in combination can include simultaneous administration of two or more agents in the same dosage form, simultaneous administration in separate dosage forms, and separate administration. That is, the subject therapeutic composition and another therapeutic agent can be formulated together in the same dosage form and administered simultaneously. Alternatively, subject therapeutic composition and another therapeutic agent can be simultaneously administered, wherein both the agents are present in separate formulations. In another alternative, the therapeutic agent can be administered just followed by the other therapeutic agent or vice versa. In the separate administration protocol, the subject therapeutic composition and another therapeutic agent may be administered a few minutes apart, or a few hours apart, or a few days apart.

An anti-cancer first treatment may be administered before, during, after, or in various combinations relative to a second anti-cancer treatment. The administrations may be in intervals ranging from concurrently to minutes to days to weeks. In embodiments where the first treatment is provided to a patient separately from the second treatment, one would generally ensure that a significant period of time did not expire between the time of each delivery, such that the two compounds would still be able to exert an advantageously combined effect on the patient. In such instances, it is contemplated that one may provide a patient with the first therapy and the second therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an immune checkpoint inhibitor therapy is "A" and an anti-cancer therapy is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include DNA damage checkpoint inhibitors, such as CHK inhibitors (AZD7762, Prexasertib, GDC-0575, CCT245737), ATR inhibitors (AZD6738, BAY1895344, M4344, Berzosertib), Wee1 inhibitors (AZD1775), DNA-PK inhibitors (M9831, Nedisertib, CC-115); alkylating agents, such as thiotepa and cycosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); temozolomide; bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen (Carter et al., 2008; Teicher 2014; Leal et al., 2014). Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach (Teicher 2009) and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis*, *Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints are molecules in the immune system that either turn up a signal (e.g., co-stimulatory molecules) or turn down a signal. Inhibitory checkpoint molecules that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), programmed death ligand 1 (PD-L1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. 20140294898, 2014022021, and 20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is PDR-001 (spartalizumab), AMP-224 or AMP-514. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342. In some embodiments, the PD-1 axis inhibitor is an anti-PD-L1 antibody, such as atezolizumab, avelumab, durvalumab, BMS-936559, or CK-301.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al., 1998; Camacho et al., 2004; Mokyr el al., 1998 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WOO 1/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesions such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. ARTICLES OF MANUFACTURE OR KITS

Further embodiments of the present disclosure include kits for the measurement, analysis, and reporting of gene expression and transcriptional output. A kit may include, but is not limited to microarray, quantitative RT-PCR, or other genomic platform reagents and materials, as well as hardware and/or software for performing at least a portion of the methods described. For example, custom microarrays or analysis methods for existing microarrays are contemplated. As another example, panels of Nanostring probes are contemplated. Accordingly, an article of manufacture or a kit is provided comprising a customized assay for determining the gene signature score also provided herein. The article of manufacture or kit can further comprise a package insert comprising instructions for using the customized assay to determine the gene signature score and to then treat or delay progression of breast cancer or ovarian cancer in an individual. Probes for any of the genes described herein may be included in the article of manufacture or kits. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. Suitable containers for the one or more agent include, for example, bottles, vials, bags and syringes.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Microarrays. Microarray analysis was conducted as described previously (Peng et al., 2014). Specifically, total RNA was extracted from the cells 48 hours after plating in presence or absence of doxycycline using a QIAGEN RNeasy RNA isolation kit. Complementary RNA was generated using a TotalPrep RNA amplification kit and loaded onto a HumanHT-12 v4 Expression BeadChip for analysis using the manufacturer's procedure.

Generation of RSR defect signature. Differentially expressed genes between shCTRL and each model cell line (shATR, shATM, shCHEK1, shCHEK2) were determined with a false discovery rate of 5% and fold change threshold of 1.25. Genes that were commonly differentially expressed between all 4 model lines were taken to be the RSR defect gene signature, with coefficients for each gene defined by the average fold change between the four model lines.

Expression signature score. Expression signature scores were computed based on correlation coefficient between the coefficients in the gene signature and corresponding expression level in a given sample (McGrail et al., 2017; van de Vijver et al., 2002), with higher values representing a stronger correlation.

Cell cycle restart assay. The ability of cells to recover from replication stress was performed as previously described (Ercilla et al., 2016; Liu et al., 2011; Mordes et al., 2008; Puddu et al., 2011). Replication forks were stalled by treatment with 2 mM hydroxyurea (HU) for 16 hours, or mock treated with water. Cells were then washed to remove HU and released into pre-equilibrated media containing 1 μg/mL nocodazole for 10 hours to collect cells in G2/M phase. Cells were then harvested, ethanol fixed, stained with propidium iodide, and analyzed by flow cytometry.

Aldehyde dehydrogenase assay. Aldehyde dehydrogenase was detected using the Aldefluor kit (STEMCELL Technologies) per the manufacturer's instructions. In brief, $1\times10^6$ cells/mL were incubated with Aldefluor reagent in presence or absence of ALDH inhibitor DEAB for 45 minutes at 37° C. Cells were washed, re-suspended in ALDH buffer, and analyzed by flow cytometry. Positive cells were gated relative to the DEAB-treated negative control. In some instances, cells were treated with AZD6244, SCH772984, or 2 μg/mL doxycycline 48 hours prior to analysis.

Enrichment of cancer stem cells. MCF-7 or ZR-75-1 cells (50,000) were seeded in an ultra-low-attachment surface 10 cm plates (Corning), incubated with mammosphere medium (RPMI 1640, 20 ng/μL EGF, 10 ng/μL FGF, and 1× B27), and cultured for 1 week before dissociation by trypsin and re-plating in the same media. After an additional week of culture, resulting clones were isolated, dissociated by trypsin, and plated in standard growth conditions for use in experiments.

Statistics. Unless otherwise noted, all values are plotted as mean+/−S.E.M. of three independent biological replicates, with significance determined by one-way ANOVA followed by a Holm-Sidak post-hoc test. If only two groups were being compared, a student's t-test was used instead of ANOVA.

Cell culture and reagents. MCF-10A, MDA-MB-231, MDA-MB-436, MCF-7, ZR-75-1, and HMEC cell lines were purchased from American Type Culture Collection (ATCC). MDA-MB-231, MCF-7, and ZR-75-1 were cultured in RPMI 1640 supplemented with 10% fetal bovine serum. MDA-MB-436 were cultured in DMEM supplemented with 10 µg/mL insulin. MCF-7 SNAIL (SNAIL-6SA) and empty vector control cells were cultured as previously described (Zhou et al., 2004). MCF-10A and HMEC cells were cultured in mammary epithelial growth medium (1:1 DMEM:F12 supplemented with 5% horse serum, 0.5 mg/mL hydrocortisone, 10 µg/mL insulin, 20 ng/mL recombinant EGF, 100 ng/mL cholera toxin, 1:100 penicillin:streptomycin). Antibodies against cyclin E (HE12; sc-247), p21 (C-19; sc-397), CHK1 (G4; sc-8408), and p53 (DO-1; sc-126) were purchased from Santa Cruz Biotechnology. Antibodies against CHK2 (2662), phosphorylated CHK2 (Thr68; 2661), phosphorylated p53 (Ser15; 9284), and a senescence β-galactosidase staining kit (9860) were purchased from Cell Signaling Technology. Antibodies against ALDH1A3 (ab80176) and BrdU (ab6326, clone BU1/75 (ICR1)) were purchased from Abcam. Antibodies against phosphorylated histone H2A.X (Ser139; clone JBW301, 05-636) were purchased from EMD Millipore. An ALDEFLUOR kit (01700) was purchased from STEM-CELL Technologies. TotalPrep RNA amplification kit (AM1561) and HumanHT-12 v4 Expression BeadChip kit (BD-103-0204) were purchased from Illumina. A CometAssay® kit (4250-050-K) was purchased from Trevigen. AZD6244 (S1008) and CI-1040 (S1020) were purchased from Selleck Chemicals. SCH772984 (CT-SCH772) and VRT-11e (CT-VX11e) were purchased from ChemieTek. trans-Retinoic acid (ab120728) was purchased from Abcam. MTT (M2128) and a monoclonal anti-BrdU antibody (B8434) were purchased from Sigma-Aldrich. Matrigel Basement Membrane Matrix (BD 354234) was purchased from BD Biosciences. Richard-Allan Scientific HistoGel Specimen Processing Gel (HG-4000-012) was purchased from Thermo Scientific. The transfection reagents Lipofectamine 2000 (11668019) and Lipofectamine 3000 (L3000015) were purchased from Life Technologies. ON-TARGETplus human CDKN1A siRNA (L-003471-00-0020), ON-TARGETplus human MAPK1 siRNA (L-003555-00-0020), and ON-TARGETplus human MAPK3 siRNA (L-003592-00-0020) were purchased from GE Dharmacon.

Lentiviral infection and siRNA transfection. MCF-10A cyclin E, HMEC cyclin E, and MCF-10A HRAS G12D cells were generated using the pLenti6/TO/V5-Dest vector (Invitrogen) per the manufacturer's instructions. In brief, cDNA for either cyclin E or HRAS G12D was cloned into pENTR/D-TOPO vector using a BP reaction. This pENTR Cyclin E or HRAS G12D vector was then used for the LR recombination reaction to transfer the gene of interest into the pLenti6/TO/V5-Dest backbone. The cells infected with individual MISSION lentiviral particles (Sigma) targeting ATM, ATR, CHEK1, and CHEK2 according to the manufacturer's instructions. After infection, cells were selected by using puromycin (1 µg/mL). For transient transfection, expression of p21 was knocked down by using ON-TARGETplus SMARTpool siRNA with Lipofectamine 3000 following the manufacturer's instructions.

Senescence assay. shCTRL, shCTRL_cycE, and RSRD cells ($5\times10^4$) were seeded in 6 wells for 48 h prior to treatment with MEK or ERK inhibitors in presence or absence of 2 µg/mL doxycycline to induce cyclin E expression. After the addition of these inhibitors, cells were cultured for another 48 h. Next, a senescence assay was performed using the senescence β-galactosidase staining kit according to the manufacturer's protocol. The percentage of senescent cells was calculated using the ratio of SA-βgal-positive cells to total cells. Mammosphere Formation Assay RSR defect model cells (5000) were seeded in an ultra-low-attachment surface 6-well plate (Corning) in mammosphere medium (50% DMEM, 50% DMEM/F12, 0.5 mg/mL hydrocortisone, 10 µg/mL insulin, 20 ng/mL recombinant EGF, 100 ng/mL cholera toxin) for 7 days in presence or absence of 2 µg/mL doxycycline to induce cyclin E expression. Spheres with diameters larger than 50 µm were scored as mammospheres.

Three-dimensional cell culture. shCTRL, shCTRL_cycE, and RSRD cells (5000) were seeded into a tissue culture-treated 8-chamber glass slide containing 200 µL of Matrigel Basement Membrane Matrix (#354234; BD Biosciences). The cells were cultured in MCF-10A medium with or without 5% horse serum for 10 days. Additional culture medium was added to each chamber every 2 days to prevent chamber drying. Three-dimensional cultures were further embedded into Histogel Specimen Processing Gel (Thermo Scientific) as described previously (Pinto et al., 2011). Paraffin embedding, sectioning, and hematoxylin and eosin staining of 3-dimensional cultures of shCTRL, shCTRL-_cycE, and RSRD cells were conducted at the MD Anderson CCSG Tissue Biospecimen and Pathology Resource.

Reverse Phase Protein Array (RPPA). shCTRL and RSRD cells ($2\times10^5$) were seeded in a 100-mm dish and collected after culture for 48 h. Lysates were extracted using a lysate buffer (1% Triton X-100, 50 mM HEPES, pH 7.4, 150 mM NaCl, 1.5 mM MgCl$_2$, 1 mM EGTA, 100 mM NaF, 10 mM sodium pyrophosphate, 1 mM Na$_3$VO$_4$, 10% glycerol, protease and phosphatase inhibitors). RPPA analysis of shCTRL and RSRD cells was performed at the MD Anderson Functional Proteomics RPPA Core Facility. Mean expression values by log 2 transformation were used to indicate the protein and phosphoprotein expression levels. Cell line screening data for determining phosphorylated MDM2 correlations was retrieved form the MD Anderson Cell Lines Project (Li et al., 2017).

Kinase inhibitor screening and dosage response assay. shCTRL, shCTRL_cycE, and RSRD cells (250) were seeded into black 384-well optical bottom plates (Nunc). For kinase inhibitor screening, a panel of 591 kinase inhibitors was used (Center for Translational Cancer Research, Institute of Biosciences and Technology, Texas A&M University, and Texas Screening Alliance for Cancer Therapeutics). For a dosage response assay, target kinase inhibitors were prepared in a series of 1 to 3 dilutions. Kinase inhibitors (1 µM) or diluted target inhibitors (10, 3.3, 1.1, 0.37, 0.123, 0.041, 0.014, 0.005, and 0.002 µM) were added to shCTRL, shCTRL_cycE, and RSRD cells after 24 h by using the multichannel pod of a Biomek FX robotic platform (Beckman Coulter). Cells were incubated with compounds for 48 h prior to being fixed with 0.5% paraformaldehyde and stained with DAPI (0.2 µg/mL). DAPI stained cells were imaged using an IN Cell Analyzer 6000 (GE Healthcare Life Sciences) with a 4× objective lens. Nuclear-stained cells were counted using the IN Cell Investigator software program (GE Healthcare Life Sciences) with nuclear segmentation parameters based on a kernel size of 5 and sensitivity of 50. Immunofluorescence Staining and Quantification Immunofluorescence staining was performed as previously described (Peng et al., 2012). In brief, following extraction of insoluble proteins by sequential incubation in cytoskeletal buffer (10 mM Pipes pH 6.8, 100 mM NaCl, 300 mM sucrose, 3 mM MgCl$_2$, 1 mM EGTA, 0.5% Triton-X100) and stripping buffer (10 mM TrisHCl pH 7.4, 10 mM NaCl, 3 mM MgCl$_2$, 1% Tween 40, 0.25% sodium deoxycholate) cells were fixed with formaldehyde. Fixed cells were permeabilized with 1% Triton-X100, blocked in 5% horse serum, and then stained for double strand breaks by γH2AX and single strand breaks by native BrdU (Pathania et al., 2014). Cells were imaged by fluorescence microscopy (Eclipse TE2000E, Nikon), capturing all images for a given replicate simultaneously to assure no variances in light intensity. For quantification, foci and nuclei were segmented, and then the integrated intensity of all foci normalized to cell area was taken as staining intensity. All analysis was performed in MATLAB (MathWorks).

Example 2—a Replication Stress Response Defect Cell Model Displays Cancer Stem Cell Characteristics MCF-10A, a well-characterized non-transformed human mammary epithelial cell line, was used to establish an isogenic replication stress response (RSR) defective model system (FIG. 1A). To model oncogene-induced replication stress, cyclin E-inducible MCF-10A (MCF10A-E) cells were engineered. Cyclin E is an important oncogene in breast cancer (Koboldt et al., 2012), and overexpression of cyclin E effectively induces DNA replication stress (Bartkova et al., 2006). In the absence of cyclin E induction, MCF10A-E cells had the same growth kinetics as wild-type MCF-10A cells, but following cyclin E induction, their growth rate was dramatically reduced (FIGS. 1B and 9A). Long-term colony formation potential was also abrogated, which corresponded to induction of senescence as shown by expression of senescence-associated β galactosidase (FIG. 9B). Consistent with the literature, onset of senescence coincided with increased DNA damage and checkpoint activation as shown by γH2AX, p-CHK2, p-p53, and p21 (FIG. 9C).

Figure 10D:
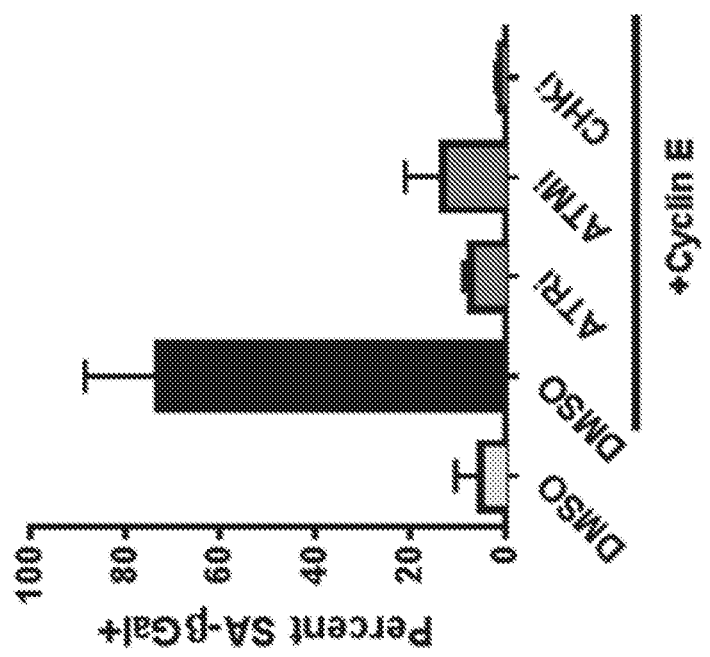
Figure 18:
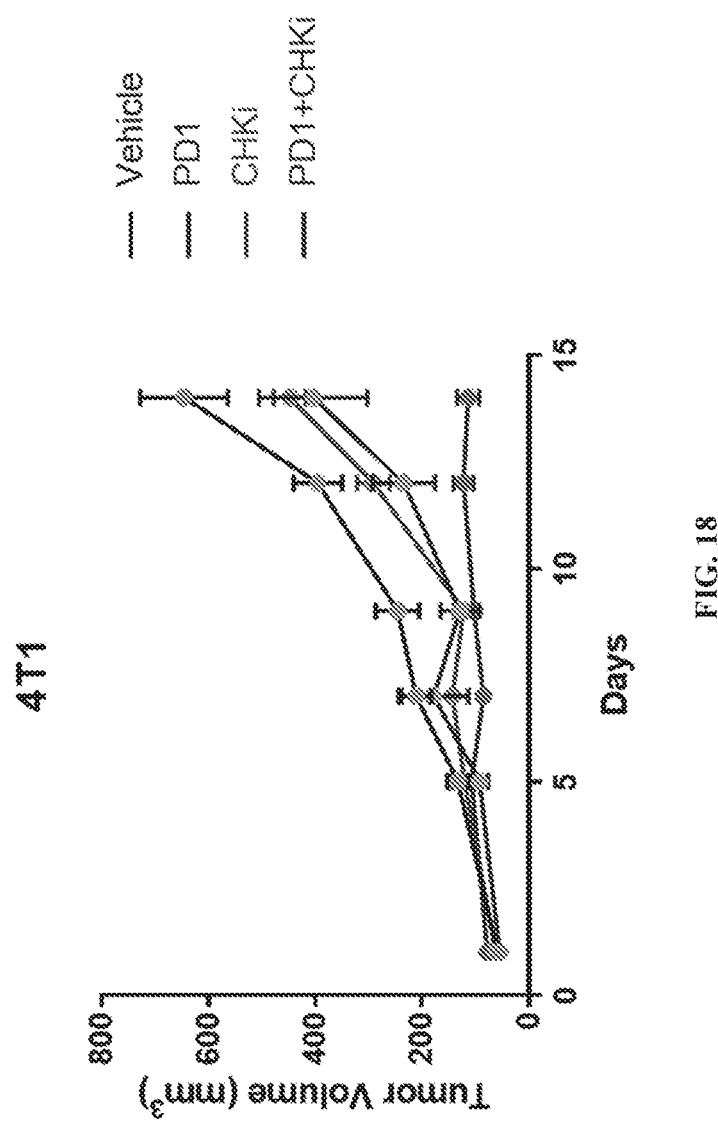
FIG. 18. Pharmaceutical induction of RSR defects sensitizes cells to immunotherapy. The 4T1 murine mammary carcinoma was implanted into syngeneic (Balb\C) mice and allowed to grow to ~100 $m^3$ before randomization. Mice were treated with either (1) 10 mg/kg anti-PD1 (clone RMP1-14) plus 25 mg/kg CHK inhibitor AZD7762 (CHKi, dissolved in beta-cyclodextrin), (2) CHKi alone with 10 mg/kg IgG control antibody, (3) PD1 alone with beta-cyclodextrin vehicle control, or (4) 10 mg/kg IgG control antibody plus beta-cyclodextrin vehicle control. At the 15 day time point, the lines represent, from top to bottom, Vehicle, CHKi, PD1, and PD1+CHKi.

In this background, defects were then induced in RSR by individually suppressing the expression of four main signaling proteins responsible for the replication stress response: ATR, ATM, CHEK1, and CHEK2 (FIG. 9D). This suppression blunted, but did not entirely mitigate, checkpoint signaling following exposure to genotoxic stress (FIGS. 9E-F), allowing cells to escape from OIS and continue proliferating following induction of cyclin E (FIGS. 1B and 9G). This coincided with repression of p21 protein levels (FIG. 1C) despite persistence of DNA damage (FIGS. 1D-E and 9H) and no changes in p21 mRNA expression (FIG. 9I). A similar effect was observed using specific kinase inhibitors against ATM, ATR, and Chk1/2 signaling, where low dose signaling suppression promoted cell growth with induction of cyclin E (FIGS. 10A-B), reduced expression of p21 (FIG. 10C), and prevented senescence (FIG. 10D). Consistent with the previous observations that complete loss of checkpoint signaling is lethal upon oncogene induced replication stress, higher inhibitor concentrations were more toxic towards cyclin E induced cells (FIGS. 10A-B). These model cell lines were functionally verified, indicating RSR was defective, by probing for recovery of cell cycle progression following hydroxyurea (HU) induced replication fork arrest, a well-established assay to determine if RSR is functionally intact (Ercilla et al., 2016; Liu et al., 2011; Mordes et al., 2008; Puddu et al., 2011). As shown in FIG. 1F, each of the RSRD model cell systems showed severe defects in the ability to recover from stalled replication forks. In addition, induction of replication stress response defects using kinase inhibitors sensitized tumors to immune checkpoint inhibitor therapy (FIG. 18).

To generate a representative RSR defective gene signature, the genes differentially expressed for each RSR defective model line relative to shCTRL cells were determined. Genes that were differentially expressed in all four model lines were then defined as the RSR defect signature (FIG. 1G, Tables 1A-B).

A similar approach has previously been used to generate a robust signature to detect defects in homologous recombination repair (Peng et al., 2014). The RSRD signature identified above was not affected by Cyclin E induction (FIG. 1H). Moreover, when applying this signature to patients with breast hyperplasia (Poola et al., 2005), it was able to correctly stratify those that would go on to form cancer versus those who would not (FIG. 1). Gene set enrichment analysis of this signature (Subramanian et al., 2005) identified mammary stem cell genes as one of the top enriched pathways (FIG. 2A), with genes identified to be up-regulated in mammary stem cells (LIM_MAMMARY_STEM_CELL_UP) showing a positive net enrichment score (NES) (FDR q-value<$10^{-4}$) indicating they are generally up-regulated. Likewise, genes down regulated in mammary stem cells (LIM_MAMMARY_STEM_CELL_DOWN) showed a negative NES (FDR q-value<$10^{-4}$), indicating they were down-regulated in the gene signature.

Figure 2B:
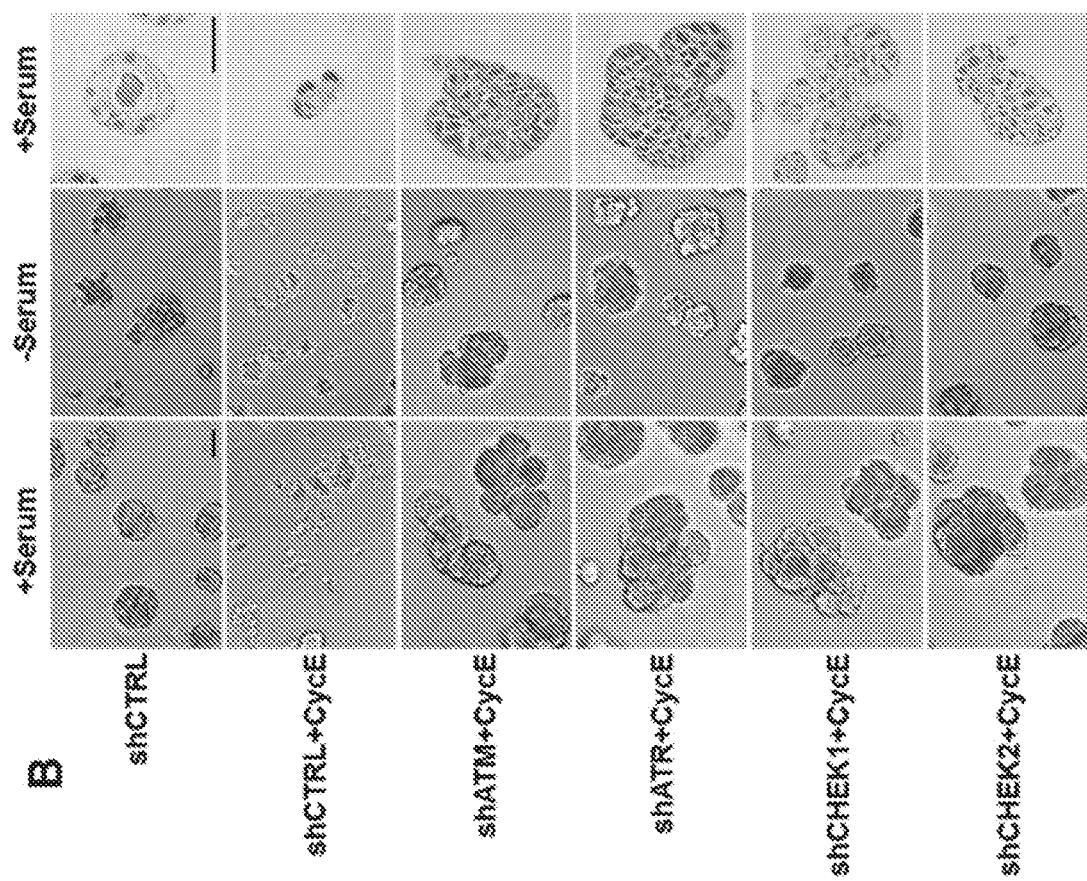
Figure 2C:
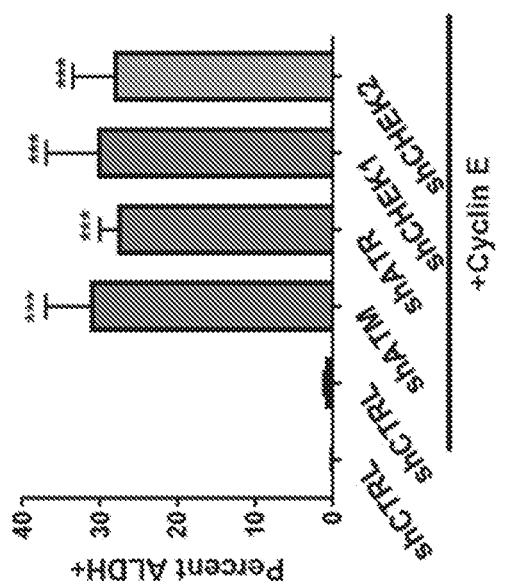
Figure 2D:
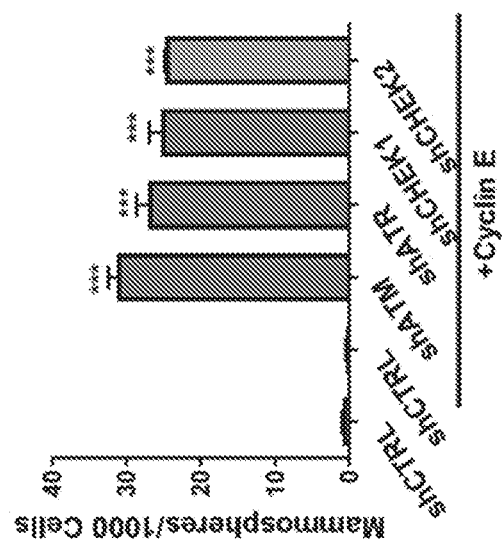

Functionally, the RSR defective model cells expressing cyclin E with knockdown of ATR, ATM, CHEK1 or CHEK2 displayed many characteristics of early tumorigenesis and cancer stem cells. An early tumorigenic phenotype was indicated by abnormal multiacinar structures in three-dimensional culture and ability to grow in absence of serum (FIG. 2B). To evaluate if the RSR defect model cells had acquired stem cell like features, the CSC marker aldehyde dehydrogenase was first evaluated (Brooks et al., 2015; Charafe-Jauffret et al., 2009; Ginestier et al., 2007; Li et al., 2017a). Detection of aldehyde dehydrogenase activity by flow cytometry showed negligible detection in shCTRL cells, which was increased to over 25% positivity in RSRD model cells (FIG. 2C). This increase in aldehyde dehydrogenase activity corresponded with increased ALDH1A3 gene and protein expression (FIGS. 11A-B). To further verify this increase in CSC character functionally, the ability of RSRD cells to form mammospheres in reduced-serum anchorage-independent growth conditions was analyzed (Creighton et al., 2009; Gupta et al., 2009; Lu et al., 2013; Wielenga et al., 2015), finding that RSRD model cells showed robust mammosphere formation ability, which was not observed in control knockdown cells (FIG. 2D). This phenotype was conserved by stable depletion of ATM, ATR, CHEK1, and CHEK2 in a different cell line background, with expression of different oncogenes (FIG. 11C), as well as in absence oncogene induction (FIG. 11D).

Example 3—Cancer Stem-Like Cells Harbor RSR Defects

Figures 3A, 3B, 3C:
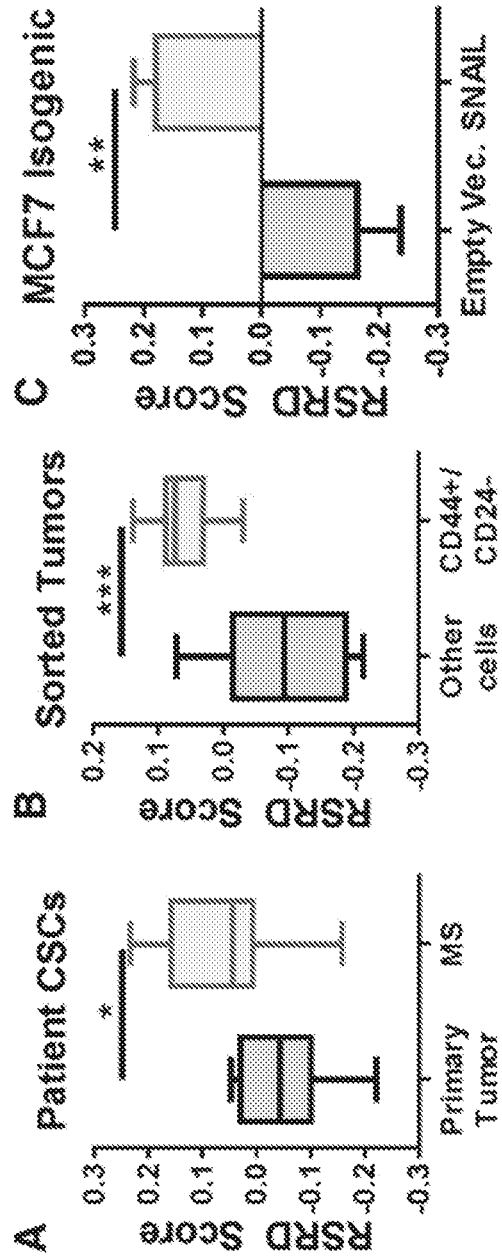
FIGS. 3A-H: CSCs have inherent defects in replication stress response.

While increased CSC characteristics were seen in the RSR defective cell lines, it remained unclear if RSR defects were inherently present in CSCs. To determine if the RSR defect signature was conserved in CSCs from patients, data from breast cancer patients following CSC enrichment was analyzed via two different mechanisms (Creighton et al., 2009). In the first approach, tumors were dissociated and cultured in reduced serum anchorage-independent conditions to enrich for CSCs. The resulting CSC-enriched mammospheres had a significantly higher RSR defect score than their primary tumor counterparts (FIG. 3A). This result was verified in a second approach, utilizing FACS of primary tumors to isolate CSCs defined as $CD44^{high}/CD24^{low}$ cells from the bulk tumor cells, which also showed enrichment in RSR defect score (FIG. 3B). Finally, it was examined whether this transcriptional re-wiring could be recapitulated in vitro, using an isogenic model of MCF7 cells overexpressing a stable mutant of SNAIL (McGrail et al., 2015; Zhou et al., 2004). Epithelial-to-mesenchymal transition (EMT) is known to induce CSC characteristics (Shibue and Weinberg, 2017), and previous studies have indicated SNAIL expression is sufficient to produce this phenotype in human mammary cells (Mani et al., 2008). As shown in FIG. 3C, the CSC-like MCF7-SNAIL cells exhibit an increased RSRD score compared to an empty vector control.

Figures 3D, 3E:
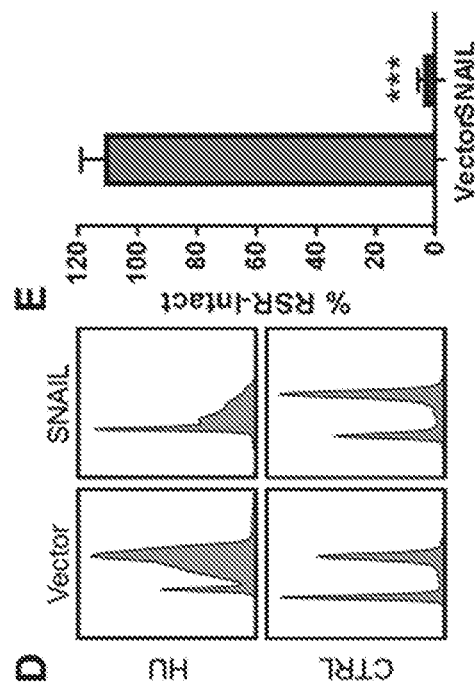
Figure 3F:
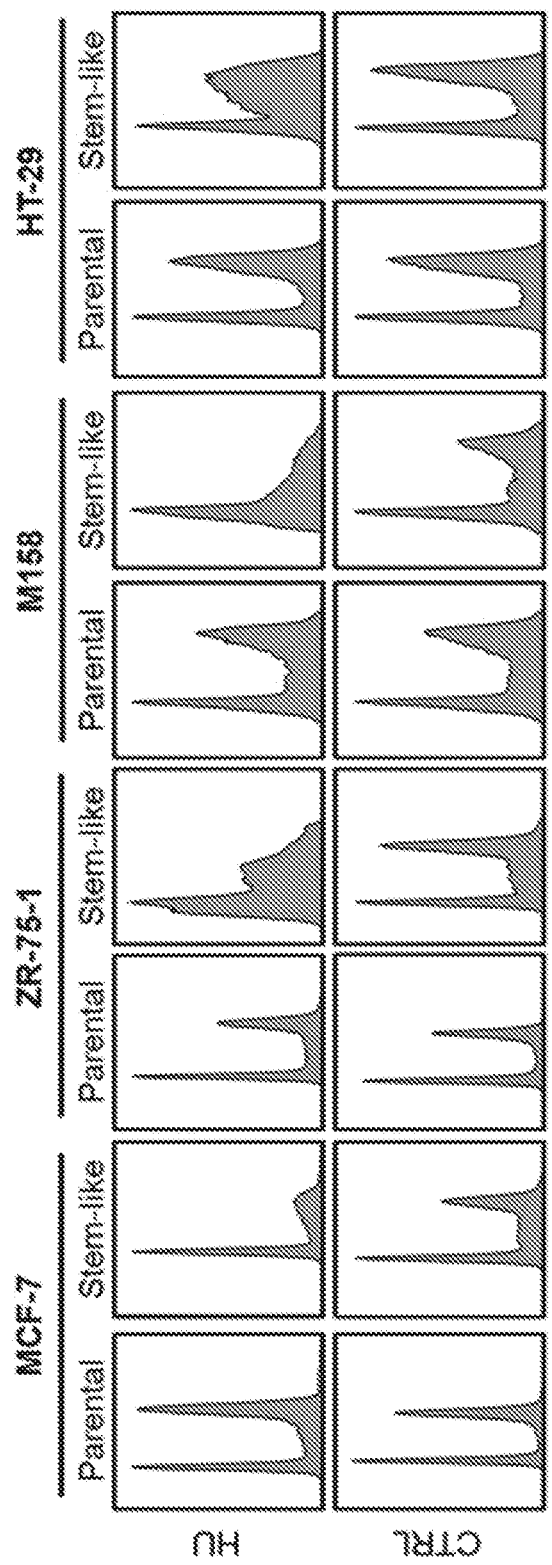
Figure 3G:
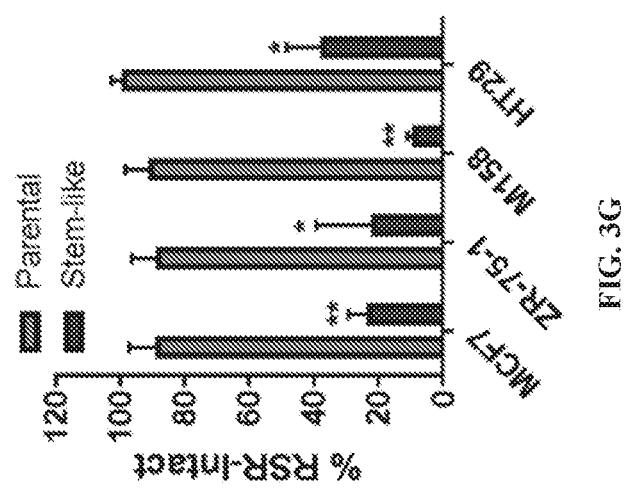

To functionally validate this phenotype, the cell cycle restart assay was repeated with hydroxyurea (FIG. 1F) in the isogenic MCF7-SNAIL line, which had an increase in RSR defect score (FIG. 3C). Consistent with the prediction from the RSRD signature score, these cells display functional defects in recovering from hydroxyurea-stalled forks (FIGS. 3D-E). To verify this genetically engineered model, human mammary tumor cell lines MCF7 and ZR-75-1, murine breast cancer cell line M158, and human colorectal cancer cell line HT-29 were cultured in reduced serum, anchorage-independent conditions (Creighton et al., 2009; Li et al., 2008) for two passages before re-isolating the resulting cells to enrich for a CSC phenotype. These CSC7 enriched populations likewise harbored defects in ability to recover from hydroxyurea-stalled replication forks (FIGS. 3F-G). Continued culture in normal growth conditions restored their original phenotype indicating this is not a permanent alteration (FIG. 12A). Time-resolved cell cycle analysis following release from HU indicated that while stem-like cells rapidly re-initiated DNA synthesis, these cells failed to complete S-phase; in contrast, parental cells showed a slower re-entry into cell cycle and a larger fraction able to complete DNA synthesis (FIG. 12B). Probing protein levels of ATM, ATR, CHK1, and CHK2 did not identify loss of any particular check-point protein (FIG. 12C). Surprisingly, these cells overexpressed CHK1 (FIG. 12D), which showed robust phosphorylation following HU treatment (FIG. 12E). Consistent results were found by immunofluorescent staining for global phosphorylation of ATM and ATR substrates using an anti-pSQ/TQ antibody (Matsuoka et al., 2007) (FIG. S4F). These results suggest that the RSR defect is not due to a failure in primary checkpoint proteins.

Figure 3H:
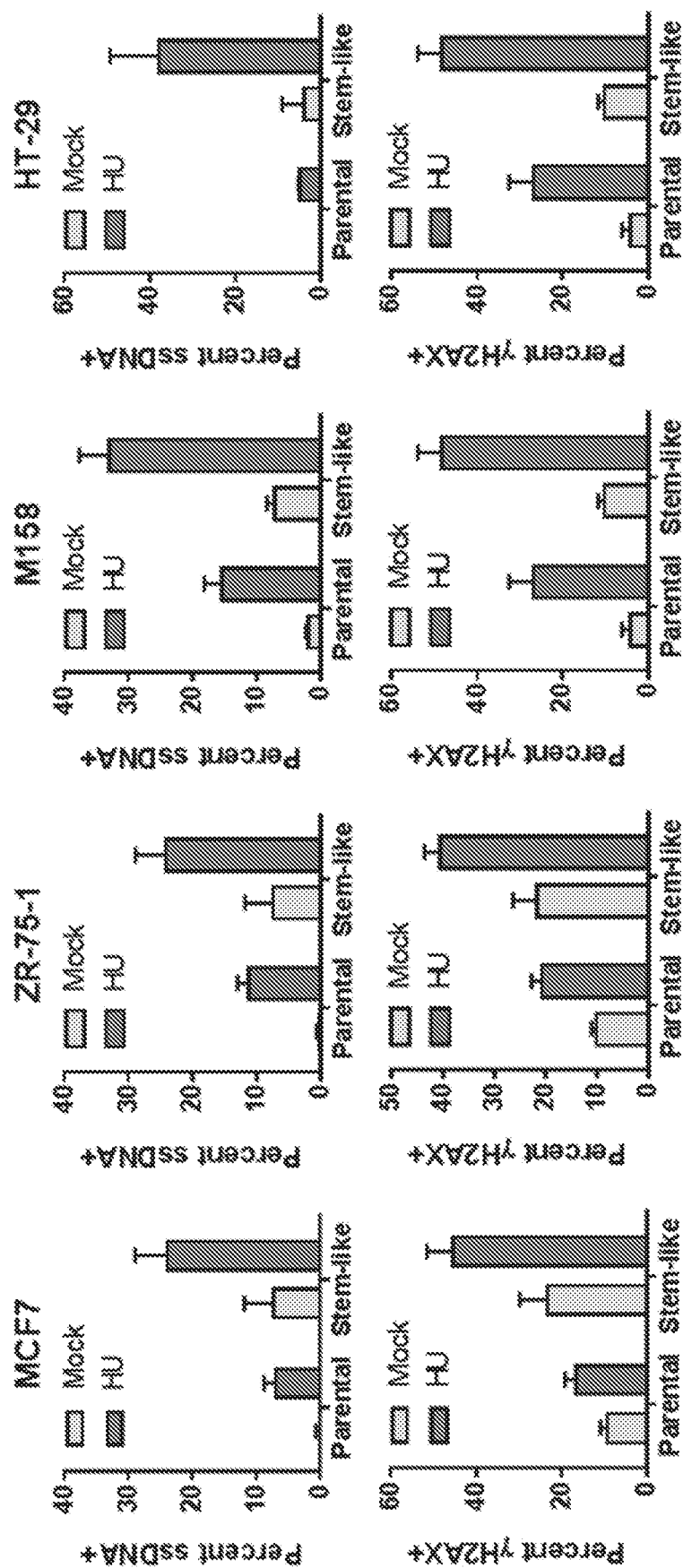

Next, DNA damage following fork stalling from HU treatment in the CSC-enriched populations was interrogated. CSC-enriched populations from all four cell line models exhibited increased single-stranded DNA breaks indicative of replication stress, which failed to recover and degenerated into double strand breaks as indicated by γH2AX foci (FIG. 3H). Quantification revealed increased single-stranded DNA both in untreated and HU-treated stem-like cells, as well as more double-stranded DNA breaks following treatment with HU (FIG. 3H). While parental cell lines were able to repair damage induced following washout of HU, this damage persisted in stem-like cells (FIG. 12C).

Example 4—MEK/ERK Inhibition Targets RSR Defective Cells and Depletes CSCs

Figure 4A:
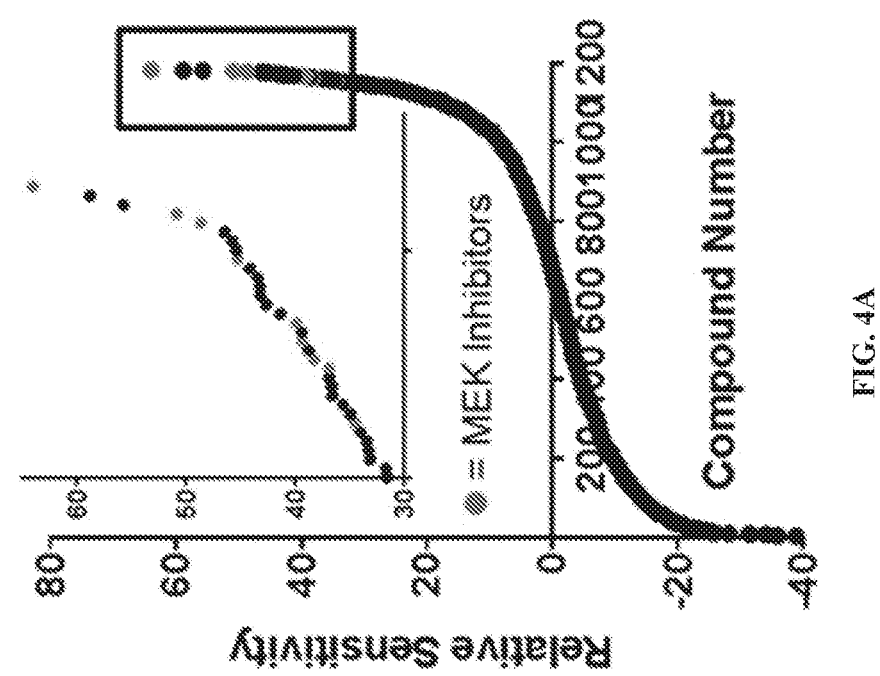
FIGS. 4A-C: High-throughput screening reveals MEK/ERK inhibition targets RSR defect cells.
Figure 4B:
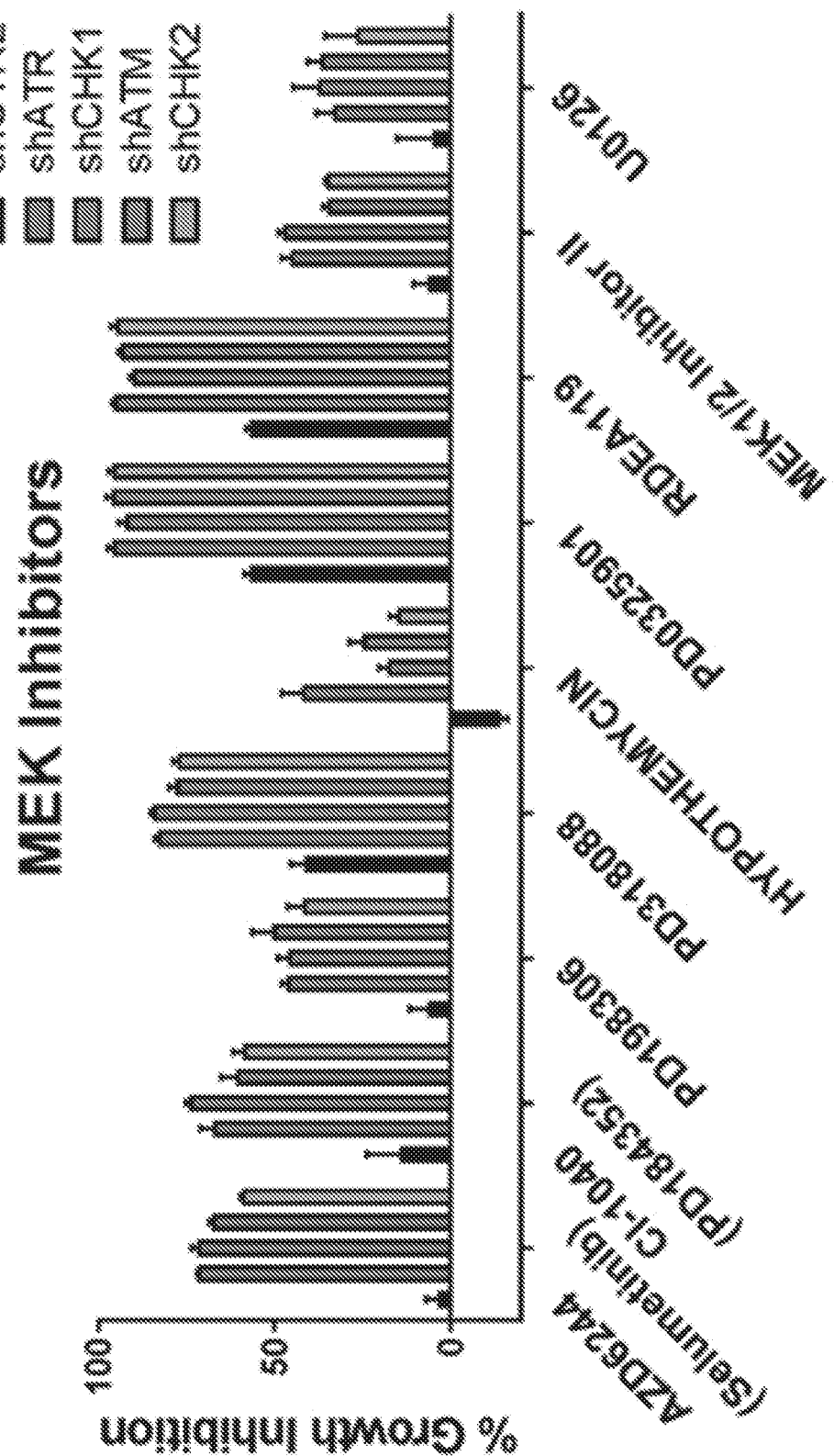
Figure 4C:
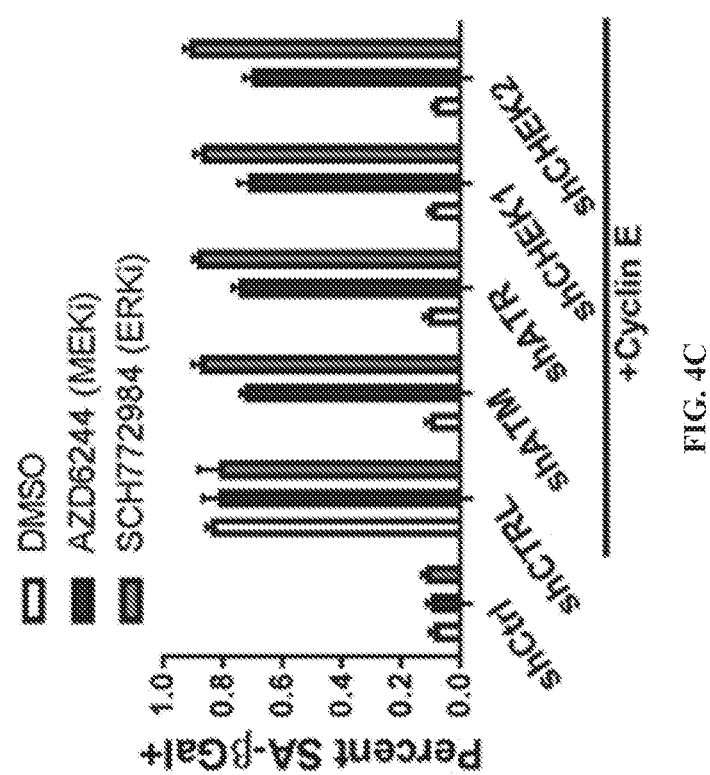

Using this RSR defect model system, by performing a high throughput screen of over 1000 compounds, molecules were identified that could specifically target the RSR defective phenotype. This screen identified multiple MEK inhibitors amongst the most potent compounds targeting RSR defective cells (FIG. 4A). While inhibitors targeting MEK consistently blocked the growth of only the RSR defective cell lines, this was not true for any other therapeutic pathways (FIG. 4B). Upon treatment with inhibitors of MEK, or its downstream effector ERK, senescence was induced to the same degree as in RSR competent cells, suggesting MEK pathway inhibition effectively recovered the ability of cells to undergo OIS (FIG. 4C).

Based on observations of inherent RSR defects in CSCs, it was hypothesized that MEK/ERK inhibition may offer a strategy to target this population. Transcriptionally, MEK inhibition correlated with a decrease in stem cell score indicating that cancer stemness was suppressed (FIG. 5A). To determine if inhibition with MEK/ERK was able to deplete CSCs, cells were treated with MEK/ERK inhibitors for 48 hours and then CSC populations were monitored based on aldehyde dehydrogenase (ALDH) activity via flow cytometry. Concentrations were chosen to be sub-lethal to the bulk population to optimally analyze targeting of CSC populations without excessive overall toxicity. As shown in FIG. 5B, MEK/ERK inhibition was able to deplete ALDH+ cells from RSRD shATR model cell line. Importantly, follow up analysis demonstrated that it could also deplete CSCs from two human triple negative breast cancer cell lines (FIG. 5C) and a CSC-enriched luminal cell line (FIG. 5B). Similar results were also observed in murine triple negative breast cancer cell lines (FIG. 5E). Taken together, these results indicate that inhibition of MEK/ERK can specifically target the RSR defect phenotype and offer a therapeutic target for CSCs.

Figures 6A, 6B, 6C:
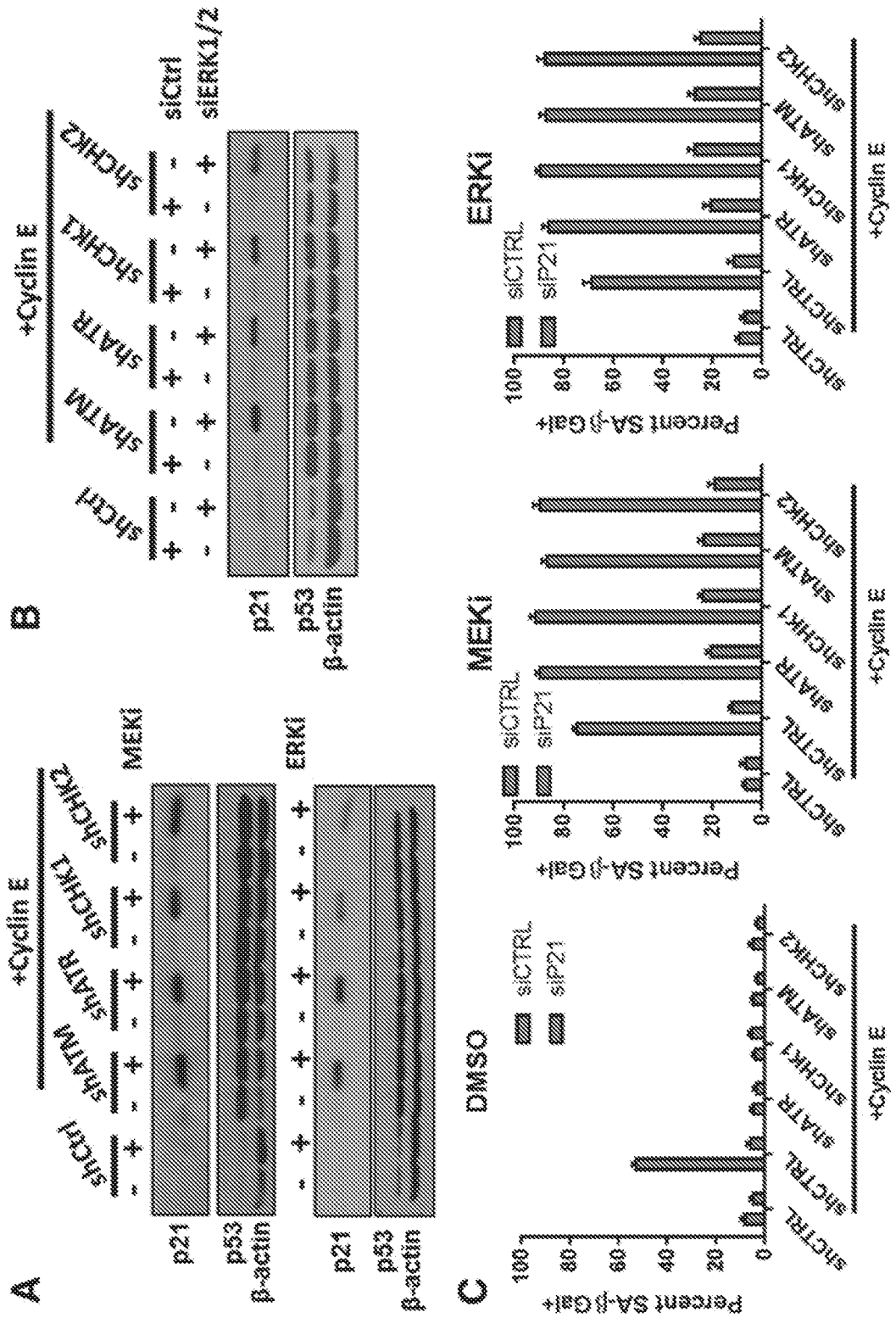
FIGS. 6A-H: Blockade of the MEK/ERK axis restores oncogene-induced senescence via a MDM2/p21 axis.

Example 5—Blockade of the MEK/ERK Axis Restores Oncogene-Induced Senescence Via the MDM2/p21 Axis As MEK/ERK inhibition induced senescence in RSR defective cells, it was hypothesized that it may be acting via p21 as previously observed in shCTRL cells undergoing OIS (FIG. 1C). Consistent with this, there was an observed increase in p21 following MEK/ERK inhibition (FIG. 6A) or genetic depletion of ERK1/2 (FIG. 6B). This increase in p21 did not coincide with increased p53 levels, and while depletion of p53 suppressed baseline p21 levels it did not inhibit the p21 upregulation following MEK inhibition (FIG. 13A) or subsequent induction of senescence (FIG. 13B). The p21 dependence of OIS restoration was verified using siRNA knockdown of p21, which blocked the ability of MEK/ERK inhibition to induce senescence (FIG. 6C).

Figures 6D, 6E, 6F, 6G, 6H:
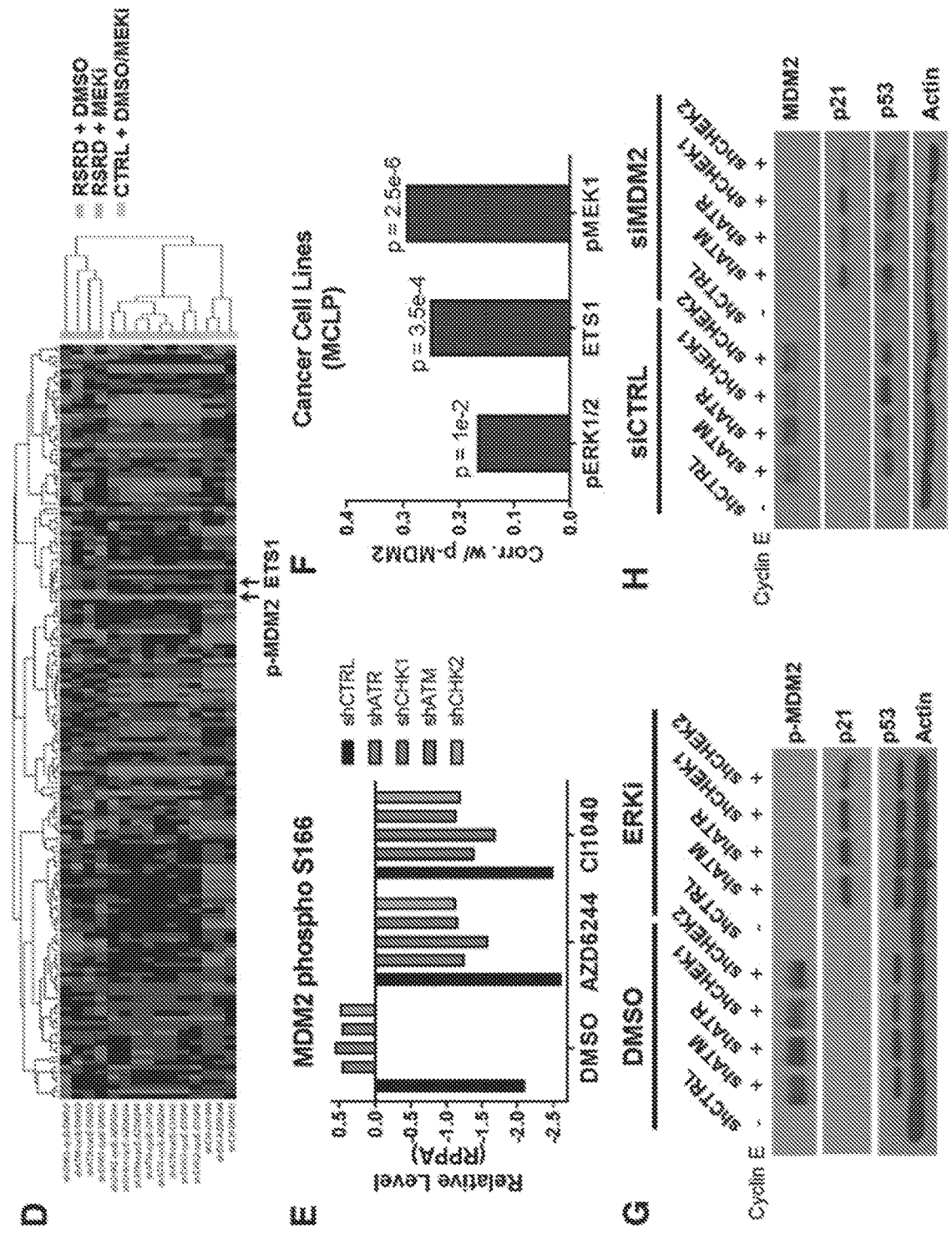

To determine the mechanism behind increased p21 stability, reverse phase protein array (RPPA) analysis was performed to simultaneously quantify over 200 proteins (FIG. 6D). Among the most up-regulated proteins in RSRD cells was phospho-MDM2, which was subsequently suppressed following MEK inhibition (FIG. 6E). In contrast, RSR-intact shCTRL cells showed no upregulation of phospho-MDM2 following induction of cyclin E (FIG. 13D). Previous studies have shown that MDM2 can be phosphorylated by MEK/ERK, and analysis of hundreds of cell lines from the MD Anderson Cell Line Project demonstrated that MDM2 phosphorylation positively correlated with phosphorylated MEK, phosphorylated ERK, and downstream effector ETS1 (Li et al., 2017b) (FIG. 6F). This result was confirmed by Western blot analysis, where ERK inhibition blocked MDM2 phosphorylation and increased p21 levels (FIG. 6G). To verify that MDM2 was the primary regulator of p21 expression, MDM2 was depleted, which was found to be sufficient to restore p21 expression in RSR-defect cells (FIG. 6H). Taken together, these results indicate that MDM2 negatively regulates p21 independent of p53, consistent with previous reports (Zhang et al., 2004).

These data demonstrate an inherent connection between defects in replication stress response and the cancer stem cell phenotype, and identify new therapeutic modalities to target these defects. Replication stress is known to be a primary driver of genomic instability in cancer (Gaillard et al., 2015). In normal cells, replication stress from oncogene activation, nucleotide depletion, DNA lesions and other causes activates the replication stress response pathway to maintain genomic integrity. Defects in RSR allow pre-malignant cells to escape oncogene-induced senescence (Di Micco et al., 2006), ultimately leading to the survival and proliferation of genomically unstable cancer cells (Dapic et al., 2005; Halazonetis et al., 2008; Osborn et al., 2002). In this study, isogenic RSR defect cell line models were generated to study this process. Using these model cell lines, a robust RSR defect gene expression signature was developed by analyzing the conserved transcription changes in cells with suppressed ATR, ATM, CHEK1, and CHEK2. Previous studies have found that defects in S-phase DNA repair can activate the STING pathway, which could contribute to this re-wiring (Parkes et al., 2017). Another potential driving candidate is AP-1, which is activated down-stream of DNA damage as well as ERK (Christmann and Kaina, 2013), both of which are elevated in RSR defect cell lines. Indeed, the most up-regulated gene in the signature, MMP1, is a target of AP-1 (Eferl and Wagner, 2003).

This RSRD gene signature may serve as a powerful biomarker for early detection of cancer, particularly in high risk patients, and could help motivate more aggressive prevention strategies, as it correctly stratified biopsies of breast hyperplasia by which patients would ultimately develop cancer (FIG. 1I). Alternatively, a lack of a RSRD gene signature could be used to identify patients who could be treated conservatively. With gene signatures such as Prosigna (Wallden et al., 2015) and MammaPrint (Cardoso et al., 2016) transitioning into the clinic, the necessary infrastructure to perform this screening is becoming more well-developed making this preventative testing a realistic goal.

This study discovered a close link between RSR defects and cancer sternness. Importantly, it provides the first evidence that cancer stem cells have inherent defects in their ability to respond to replication stress. Analysis of patient-derived CSCs showed an enrichment in RSR defect character (FIGS. 3A-B), which was also observed by overexpressing the sternness driver SNAIL in MCF7 cells (FIG. 3C). This prediction was validated in the stem-like MCF7-SNAIL cells (FIGS. 3D-E), as well as CSC-like cells isolated from cancer cell lines of various species and lineages (FIGS. 3F-G). Recent work has shown that cultured embryonic stem cells are likewise plagued by high levels of replication stress leading to genomic instability (Ahuja et al., 2016), and that replication stress is a key driver of declining fitness of hematopoietic stem cells with age (Flach et al., 2014). Taken together with the above, these studies raise the prospect that normal stem cells may harbor an innate ability to suppress the replication stress response, possibly to enable rapid proliferation in response to tissue injury, which could pre-dispose stem/progenitor cells to tumorigenesis relative to more differentiated counterparts. A growing body of evidence suggests many cancers arise from stem or progenitor cells within a given tissue (Van Keymeulen et al., 2015). In intestinal cancers, genetically engineered mouse models have demonstrated that only that most primitive Lgr5+ crypt stem cells can give rise to tumors following APC deletion (Barker et al., 2009). In more terminally differentiated cells, APC loss resulted in growth of microscopic lesions that failed to progress to form tumors, which could be explained by activation of the replication stress response and oncogene-induced senescence. Similar results were recently obtained using $BRAF^{V600E}$ as the oncogenic driver (Tong et al., 2017). There were no obvious defects detected in RSR checkpoint protein levels or activation to explain RSR defects in stem-like populations (FIGS. 12C-F). It may be possible that the defect is regulated at the replication fork level instead of the checkpoint response level, or that an opposing signal overrides any retardation of the cell cycle downstream of CHK1 phosphorylation. Replication fork stability may be analyzed by DNA fiber combing assays in response to hydroxyurea (Ying et al., 2012), and differential recruitment of proteins to stalled forks could be monitored precipitation of nascent DNA using iPOND (Sirbu et al., 2012). Alternatively, SILAC-based mass spectrometry could be used to monitor whole proteome changes in response to hydroxyurea to probe if there is differential response in parental and stem-like populations (Stokes et al., 2007). These future studies investigating the origins of this defect may shed more light on CSC biology and aid in targeting CSCs without unwanted toxicity to normal stem cells.

Clinically, CSCs exhibit inherent chemotherapeutic resistance (Li et al., 2008, Tanei et al., 2009), and their presence correlates with poor prognosis (Ginestier et al., 2007; Zhou et al., 2009). To address this problem, pathways were identified that may be synthetically lethal with defects in RSR, analogous to how cells with defective homologous recombination repair may be targeted by PARP inhibitors (Bryant et al., 2005). Inhibition of the MEK/ERK axis was found to specifically target RSRD cells as well as CSCs. Treatment of RSRD cells with MEK/ERK inhibitors restored oncogene-induced senescence by increasing protein levels of p21 (FIGS. 4C and 6A-C), without any modulation of its primary transcription factor p53. RSR defect model cell lines universally expressed higher levels of p53, even in cells with suppression of ATM, a primary activator of p53 down-stream of genotoxic stress. This increased p53 in shATM cells may be through ATR, or could be through unrelated pathways, such as depletion of ribonucleotides or reactive oxygen species (Eferl & Wagner, 2003). To verify that p53 was dispensable for p21 upregulation, p53 was depleted with siRNA and MEK inhibition still robustly increased p21 levels and induced senescence (FIGS. 13A-B), suggesting a post-translational regulatory mechanism. Functional proteomics by RPPA showed that not only do RSRD cell lines overexpress phosphorylated MDM2, but that this overexpression is lost following MEK/ERK inhibition (FIGS. 6D-E). Previous studies have shown MDM2 to be a substrate of MEK/ERK (Malmlof et al., 2007), and across hundreds of cell lines, phosphorylated MEK and ERK corresponded with increased phospho-MDM2 (FIG. 6F). Taken together, this suggests that MDM2 may act to degrade p21. Indeed, MDM2 has been shown to negatively regulate p21 protein independent of p53 by increasing binding of p21 to proteosomal subunit C8 (PSMA3), leading to p21 degradation (Zhang et al., 2004). Although current MDM2 inhibitors target the MDM2-p53 interaction, next generation inhibitors that broadly block MDM2 to also stabilize p21 could offer another powerful therapeutic option to target CSCs. Broad blockade of MDM2 activity may also offer an attractive preventative strategy. Pre-screening of patients using the RSR defect gene signature could further improve patient targeting for preventative strategies, enabling treatment of only patients who show highest risk of cancer development.

Example 6—RSRD Gene Signature Predicts Immune Checkpoint Blockade Response

PD-L1 has been approved as a biomarker in non-small-cell lung cancers, with patients exhibiting over 50% PD-L1 positivity showing response to immunotherapy. In a follow-up study, PD-L1 positivity did not show predictive power in melanoma. Recently, microsatellite instability caused by mismatch repair defects has been approved as a pan-cancer biomarker for immunotherapy, though tumors characterized by microsatellite instability only exceed 15% of patients in colorectal, endometrial, and gastric cancers, with minimal presence in other cancers. Mechanistically, microsatellite instability status is thought to drive immunotherapy efficacy due to its correlation with increased mutational burden. However, kidney cancer patients treated with immunotherapy shown no relationship between mutational burden and therapeutic efficacy. As outlined below, there is reason to believe this to be the case with numerous other tumor lineages, including breast and pancreatic cancers.

It has been found that there is no relationship between immunotherapy response and mutational burden (Miao et al., 2018). This suggests that current clinically approved biomarkers would be of little use, and there are currently no clinically approved biomarkers for immunotherapy response in renal clear cell carcinoma, despite demonstrated activity of immune checkpoint blockade in approximately 30% of patients. Thus, the RSRD gene signature was examined in the same cohort as Miao et al. (2018). The RSRD score determined above was found to accurately predict both progression free survival (P=0.0017, Hazard ratio=0.22, FIG. 7A) and overall survival (P=0.0009, Hazard ratio=0.0, FIG. 7B). The efficacy of the RSRD gene signature as a biomarker is further evidenced by the receiver-operating characteristic curve derived by predicting patient clinical benefit based on RSRD score, giving an area under the curve (AUC) value of 0.80, where 1.0 is a perfect prediction and 0.50 is random assignment (FIG. 7C). Miao et al. (2018) had identified PBRM1 mutations as a potential response biomarker, and treatment history as co-variate. Thus, multivariate survival analysis was performed with RSRD score, PBRM1 status, and treatment history. This analysis found that treatment history and RSRD score, but not PBRM1 status, to be independent prognostic markers (FIG. 7D). Overall, the response rate for immunotherapy in the entire cohort was 36%. For patients with PBRM1 mutations, this rises to 47%. However, with the RSRD signature high group, a significantly increased response rate of 73% was seen, indicating the RSRD gene signature is an excellent predictor for treatment response in renal clear cell carcinoma patients.

Given the high response rate within the RSRD signature high group, it was hypothesized that the utility of the RSRD gene signature may be expanded to numerous additional cancer types. Consistent with observations in Miao et al. (2018), even though the TCGA clear cell renal cancer cohort (KIRC) showed the highest median cytotoxic T-cell (CTL) score (FIG. 8A), this cohort presented some of the lowest levels of neoantigens (FIG. 8B). This phenotype is inconsistent with other models, such as MSI status as a biomarker, that propose mutation burden and neoantigen presentation are the primary drivers of CTL infiltration. When comparing on a per-cancer basis, several lineages do show a correlation between CTL score and neoantigen presentation; however, this is not true of numerous lineages including clear cell renal cancer, pancreatic, and breast cancers (FIG. 8B). Thus, the RSRD signature may have greater utility in these neoantigen-independent lineages.

To further validate the RSRD gene signature, RSRD score was evaluated in kidney cancer patients treated with immunotherapy from Ascierto et al. (2016). Patients with clinician-assessed responding patients was significantly higher than non-responding patients (FIG. 15A). The RSRD score was also evaluated in low mutation (less than 100 mutations) melanoma patients from Hugo et al. (2016) and Riaz et al. (2017). A significantly higher RSRD score was found in patients who showed response to immunotherapy (FIG. 15B). The predictive capacity of the RSRD signature score in bladder cancer patients in Snyder et al. (2017) was also evaluated. While no activity was observed in high-mutator/M-class cancers, the response of low mutation C-Class cancers was accurately predicted by RSRD score (FIG. 15C). Finally, the ability of the RSRD score to predict response to immunotherapy in stomach cancer patients from Kim et al. (2018) was assessed. Minimal predictive accuracy was observed in bulk patients, but signature activity was observed in the low-mutation microsatellite stable (MSS) patients (FIG. 15D).

RSR function was also assessed by the fraction of cells capable of completing cell cycle after replication stress. Hydroxyurea-induced replication stress was used to synchronize breast cancer cells in G/early S. Cells were released into nocodazole for collection in G2/M. Cells with intact RSR will complete the cell cycle, whereas RSR-defective cells will remain in G1/S phase (FIGS. 16A-B). FIG. 16C shows an example staining of ssDNA foci indicative of replication stress in BT-549 cells, as detected by native BrdU. FIG. 16D shows the quantification of ssDNA nuclear staining in RSRD-high and RSRD-low breast cancer cell lines. FIG. 16E shows the quantification of ssDNA nuclear staining in RCC cell lines. FIG. 16F shows the quantification of cytoplasmic ssDNA by immunostaining in breast (grey dots) and RCC (labeled dots) cell lines. Membranes were selectively permeabilized with saponin, and ssDNA degraded with S1 nuclease as a negative control. RCC cell cytokine expression was quantified by qRT-PCR following treatment with either 100 nM AZD-7762 (CHKi) or DMSO vehicle control for 24 hours (FIG. 16G). Cytokine gene expression in RSRD-high 786-0 RCC cells was assessed following transfection with siRNA against TMEM73 (STING) or non-targeting control (FIG. 16H). As such, RSRD score predicts functional replication stress response defects in human breast and kidney cancer cell lines, which correspond with increased cytoplasmic DNA and STING-dependent cytokine production.

The RSRD gene signature activity was also validated in glioblastoma patients from Zhao et al. (2019) and Cloughesy et al. (2019). RNA-sequencing gene expression data of GBM patients was acquired from Zhao et al. (2019), which had 1-3 biopsies per patient acquired pre- and/or post-treatment with PD1 inhibitors (nivolumab, N=13, pembrolizumab, N=4). Two patients only had post-treatment biopsies (1 nivolumab and 1 pembrolizumab treated). All plots represent accuracy at predicting objective response. Overall accuracy ranged from 82%-87% depending on conditions as shown in FIG. 17A-D. ROC plots were created by taking average RSRD scores from all available pre-treatment biopsies (15 patients), excluding 2 patients that only had post-treatment expression data (FIG. 17A). ROC plots were also creates using only the biopsy taken closest to the start of treatment (FIG. 17B). ROC plots were also created that included the two patients with only post-treatment biopsies, taking average RSRD score from all biopsies (FIG. 17C). Finally, ROC plots were created that included the two patients with only post-treatment biopsies, but that only used the biopsy taken closest to start of treatment to determine RSRD score (FIG. 17D).

Next, RNA-sequencing gene expression data of GBM patients treated with pembrolizumab was acquired from Cloughesy et al. (2019) with associated overall survival data. Here, one cohort was treated with pembrolizumab in both neoadjuvant and adjuvant setting (FIG. 17E, N=14), and one cohort was only treated in the adjuvant setting (FIG. 17F, N=15). While neoadjuvant treatment showed a 6.2-month improvement in survival, multivariate analysis of entire cohort showed significantly improved outcomes in RSRD high patients (FIG. 17G).

Example 7—RSRD Score is Linked to Breast Cancer Metastasis

RSRD scores were calculated for subclones of breast cancer cell line MDA-MB-231 having varying degrees of metastatic potential from two separate studies (FIGS. 14A-B). The metastatic potential was grouped as 0% (−), under 30% (+), 30%-70% (++), or above 70% (+++) of mice bearing metastasis after 60 days. As can be seen in FIGS. 14A-B, the RSRD score increases with the metastatic potential in each case, indicating a strong correlation. RSRD scores were also calculated for two groups of patient samples, all BRCA breast cancer subtypes or triple negative breast cancer only. These patient groups were then separated by RSRD score into low and high RSRD score groups and the metastasis free survival over time was analyzed. The RSRD high group had a lower rate of metastasis-free survival over time in both groups of patients compared to the RSRD low group (FIGS. 14C-14D), indicating that the RSRD score may be used to predict the likelihood of metastasis.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ahuja et al., *Nat. Commun.*, 7:10660, 2016.
Ascierto et al., *Cancer Immunol. Res.*, 4:726-733, 2016.
Barker et al., *Nature*, 457:608-611, 2009.
Bartkova et al., *Nature*, 444:633-637, 2006.
Barretina et al., *Nature*, 483:603-607, 2012.
Berti and Vindigni, *Nat. Struct. Mol. Biol.*, 23:103-109, 2016.
Bogaerts et al., *Nat. Clin. Pract. Oncol.*, 3:540-551, 2006.
Brooks et al., *Cell Stem Cell*, 17:260-271, 2015.
Bryant et al., *Nature*, 434:913-917, 2005.
Cardoso et al., *J. Clin. Oncol.* 26:729-735, 2008.
Cardoso et al., *N. Engl. J. Med.*, 375:717-729, 2016.
Charafe-Jauffret et al., *Cancer Res.*, 69:1302-1313, 2009.
Christmann & Kaina, *Nucleic Acids Res.*, 41:8403-8420, 2013.
Cloughesy et al., *Nat. Med.*, doi: 10.1038/s41591-018-0337-7, [Epub ahead of print], 2019.
Costello et al., *Nat. Biotechnol.*, 32:1-103, 2014.
Cowin et al., *Annu. Rev. Genomics Hum. Genet.*, 11:133-159, 2010.
Creighton et al., *Proc. Natl. Acad. Sci. U.S.A.*, 106:13820-13825, 2009.
Dapic et al., *Cancer Control*, 12:127-136, 2005.
Eferl and Wagner, *Nat. Rev. Cancer*, 3:859-868, 2003.
Ercilla et al., *Nucleic Acids Res.*, 44:4745-4762, 2009.
Flach et al., *Nature*, 512:198-202, 2014.
Gaillard et al., *Nat. Rev. Cancer*, 15:276-289, 2015.
Gandarillas, *Cell Cycle*, 11:4507-4516, 2012.
Garnett et al., *Nature*, 483:570-575, 2012.
Ginestier et al., *Cell Stem Cell*, 1:555-567, 2007.
Gorgoulis et al., *Nature*, 434:907-913, 2005.
Gupta et al., *Cell*, 138:645-659, 2009.
Halazonetis et al., *Science*, 319:1352-1356, 2008.
Heiser et al., *Proc. Natl. Acad Sci. U.S.A.*, 109:2724-2729, 2012.
Hugo et al., *Cell*, 165:35-44, 2016.
Kao et al., *PLoS One*, 4:e6146, 2009.
Kim et al., *Nat. Med*, 24:1449-1458, 2018.
Koboldt et al., *Nature:* 490:61-70, 2012.
Li et al., *J. Natl. Cancer Inst.*, 100:672-679, 2008.
Li et al., *Cell Stem Cell*, 20:303-314.e5, 2017a.
Li et al., *Cancer Cell:* 31:225-239, 2017b.
Liu et al., *Cell Death Differ.*, 18:841-852, 2011.
Lowe et al., *Nature*, 432:307-315, 2004.
Lu et al., *Cancer cell*, 23:171-185, 2013.
Malmlof et al., *J. Biol. Chem.*, 282:2288-2296, 2007.
Mani et al., *Cell*, 133:704-715, 2008.
Matsuoka et al., *Science*, 316:1160-1166, 2007.
McGrail et al., *FASEB. J.*, 29:1280-1289, 2015.
McGrail et al., *Npj Syst. Biol. Appl.*, 3:8, 2017.
Miao et al., *Nat. Genet.*, 50:1271-1281, 2018.
Di Micco et al., *Nature*, 444:638-642, 2006.
Mordes et al., *Genes Dev.*, 22:1478-1489, 2008.
Neve et al., *Cancer Cell*, 10:515-27, 2006.
Osborn et al., *Trends Cell Biol.*, 12:509-516, 2002.
Parkes et al., *J. Natl. Cancer Inst.*, 109:djw199, 2017.
Pathania et al., *Nat. Commun.*, 5:5496, 2014.
Peng et al., *Cancer Res.*, 72:2802-2813, 2012.
Peng et al., *Nat. Commun.*, 5:3361, 2014.
Pinto et al., *Front. Endocrinol.* 2:15, 2011.
Pitroda et al., *Sci. Transl. Med.*, 6:229ra42, 2014.
Poola et al., *Nat. Med.*, 11:481-483, 2005.
Puddu et al., *PLoS Genet.*, 7:e1002022, 2011.
Riaz et al., *Cell*, 171:934-949, 2017.
Shibue & Weinberg, *Nat. Rev. Clin. Oncol.*, 14(10):611-629, 2017.
Sirbu et al., *Nat. Protoc.*, 7:594-605, 2012.
Snyder et al., *PLoS Med.*, 14:e1002309, 2017.
Stokes et al., *Proc. Natl. Acad Sci. U.S.A.*, 104:19855-19860, 2007.

Subramanian et al., *Proc. Natl. Acad. Sci. U.S.A.*, 102: 15545-15550, 2005.
Tanei et al., *Clin. Cancer Res.*, 15:4234-4241, 2009.
Tong et al., *Cell Rep.*, 21:3833-3845, 2017.
van de Vijver et al., *N. Engl. J. Med.*, 347:1999-2009, 2017.
Van Keymeulen et al., *Nature*, 525:119-123, 2015.
Wallden et al., *BMC Med. Genomics*, 8:54, 2015.
Wang et al., *Cell*, 148:1001-1014, 2012.
Wielenga et al., *Cell Rep.*, 13:489-494, 2015.
Ying et al., *Cancer Res.*, 72:2814-2821, 2012.
Zhang et al., *J. Biol. Chem.*, 279:16000-16006, 2004.
Zhao et al., *Nat. Med.*, doi: 10.1038/s41591-019-0349-y, [Epub ahead of print], 2019.
Zhou et al., *Nat. Rev. Drug Discov.*, 8:806-823, 2009.
Zhou et al., *Nat. Cell Biol.* 6:931-940, 2017.

The invention claimed is:

1. A method of treating cancer in a patient comprising:
    (a) assaying the mRNA expression levels of the genes MMP1, DKK3, and CYBA in a sample of the cancer from said patient;
    (b) identifying the patient as having a MEK/ERK inhibitor and/or an immune checkpoint inhibitor sensitive cancer by calculating a signature score by normalizing the mRNA expression levels of said MMP1, DKK3, and CYBA genes to at least one reference gene and calculating a correlation coefficient between the coefficient of MMP1 of 6.019471, DKK3 of 5.224194, and CYBA of −6.16047 and the corresponding expression level in said sample, wherein a signature score indicative of a strong correlation identifies the patient as having a MEK/ERK inhibitor and/or an immune checkpoint inhibitor sensitive cancer; and
    (c) administering an effective amount of a MEK/ERK inhibitor and/or an immune checkpoint inhibitor to said patient identified to have a MEK/ERK inhibitor and/or an immune checkpoint inhibitor sensitive cancer.

2. The method of claim 1, wherein the cancer is a kidney cancer, renal clear cell carcinoma, a breast cancer, an ovarian cancer, a glioblastoma, a melanoma, a stomach cancer, or a bladder cancer.

3. The method of claim 1, wherein the expression levels are analyzed by RNA sequencing, microarray analysis, labeled reporter probe hybridization and imaging, nanostring analysis, or qPCR.

4. The method of claim 1, wherein the immune checkpoint inhibitor is a CTLA-4 inhibitor, PD-1 inhibitor, or PD-L1 inhibitor.

5. The method of claim 1, wherein the immune checkpoint inhibitor is ipilimumab, pembrolizumab, nivolumab, atezolizumab, avelumab, durvalumab, spartalizumab, AMP-224, or AMP-514.

6. The method of claim 1, wherein the MEK/ERK inhibitor is Trametinib, Cobimetinib, Binimetinib, Selumetinib, PD-325901, AZD 6244, or U0126.

7. The method of claim 1, further comprising administering a second anti-cancer therapy.

8. The method of claim 7, wherein the anti-cancer therapy is a chemotherapy, a radiation therapy, a hormonal therapy, a targeted therapy, an immunotherapy or a surgical therapy.

9. The method of claim 1, wherein the patient is administered a MEK/ERK inhibitor.

10. The method of claim 1, wherein the patient is administered a MEK/ERK inhibitor and an immune checkpoint inhibitor.

11. The method of claim 1, wherein the patient is administered an immune checkpoint inhibitor.

12. The method of claim 1, wherein the mRNA expression level is detected by microarray, RT-PCR, qRT-PCR, nanostring assay, or in situ hybridization.

13. The method of claim 1, further comprising assaying the mRNA expression levels of at least one additional gene from the group consisting of CCND2, SERPINB2, FST, IL1B, KRT6C, KRT14, GJA1, PLCH2, IFITM3, RAB38, IL13RA2, HAS3, MMP10, DPYSL3, DLL1, FBN2, BCAT1, PKP1, MTAP, WISPS, ARHGEF5L, SOX7, PRSS3, ARTN, NXN, FOXA2, SLC2A6, FEZ1, C1orf24, LOC651397, ERAP2, SLC35E3, ADAM19, HMGA2, RTTN, IGFBP7, MAOA, LPAR1, NTM, CNTNAP2, F2RL1, FGFBP1, IL24, CSF3, LOC375295, TUBB6, WNT7A, SPARC, FERMT1, RGS2, SLFN11, PRSS23, TMEM22, XRN2, MAMDC2, CYGB, ZBED2, SNCA, THBS1, SPHK1, IL1R2, FKBP11, NRG1, KRT6A, FAM129A, SNAI2, GPR81, SRPX, CDKN2A, TFPI2, LOC643272, TAGLN3, GADD45A, PLAU, GSTT1, TNFRSF19, NIPAL4, ISG15, LIMA1, KCTD12, ARHGAP23, PARD6G, AXL, ENTPD3, HS3ST2, KRT5, SERPINB1, ANO1, IGFL1, MARCH4, RFTN1, LAMA5, KRT6B, DLK2, SH2B3, AKAP12, JAG1, TMEM16A, WBP5, TNFRSF6B, ARMCX6, FLI1, LPXN, MTSS1, HES2, RPS23, THY1, SH2D5, IRF6, MT1G, IFIT1, FOSL1, SOCS2, HCLS1, NRCAM, TP73L, TNFRSF25, ANXA8L2, ILIA, TPST1, MTE, NLRP3, DKK1, TSPAN5, CSRP2, SLC31A2, KDELR3, HS3ST1, LOC100216001, FAT2, GNA15, CYP27B1, C20orf197, ARHGAP22, AFAP1L2, GALNT5, GRK5, RPS6KA4, SPAG1, ST3GAL5, CYR61, MMP9, TP63, UCA1, TMEM2, LOC729231, SNRPN, S100A2, SYK, COL17A1, LOC650517, TPX2, CTSC, RNASE7, TINAGL1, ISG20, TGFA, FRMD4A, PTHLH, PROCR, PHCA, TMEM156, SNRPB2, TMEM138, ADAMTS1, TRNP1, DUSP10, KRT17P3, CORO2A, RIN2, SFTA1P, CDKN2B, APOBEC3F, DFNA5, SERPINB13, KCNK6, TPST2, CTNNBL1, TBC1D2, SDHALP1, PCSK9, IL28RA, LOC653110, SNURF, LOC649679, SFN, FAM92A1, SLC2A3, F2R, LOC387882, GPR177, ETS2, CARD10, AUTS2, SLC2A9, DCBLD2, SHROOM2, ANXA8, CTNNAL1, RAP1BL, LPAR3, TRQ1, LOC642489, C20orf100, LOC644330, NCRNA00153, RGS12, ARHGDIB, SRC, CDCA4, E2F7, FOXD1, MYLK, C3orf54, CMTM7, IFIT2, NUDT11, YWHAB, APOBEC3G, PRNP, SPG3A, KCNG1, PABPC1L, COL7A1, TCEAL8, FKBP1A, DLL3, RRBP1, MT1X, WDFY2, PRSS2, EFNB1, ARID3B, ANXA10, LYPD5, AURKA, PAK6, MAP1B, ST6GALNAC5, TPM3, ABCC4, ANXA8L1, NXT1, IL1RAP, HRAS, DNTTIP1, ITGA2, MT1F, UBE2C, CNTN1, LOC652846, TUBB4Q, PGM3, CAPRIN2, LOC654121, GOSR2, SOX15, TUBB2A, C12orf31, C12orf54, ANTXR2, CSE1L, PVRL3, RAE1, PRKCDBP, P2RY2, HOXC4, CCNA1, PPP4R4, ZFP64, RGS20, BTBD11, TSPAN18,
    SIDT2, DNAJB12, KCTD20, ELL5, LOC283953, SLC27A5, SLC6A14, PPP2R2C, ARTS, TRIB1, NPEPL1, TMEM205, NOL3, LOC649853, LOC388588, NUCB1, BTG1, ID2, FER1L4, LOC146439, IL20RB, FAM195A, CEBPD, RAB40B, NFIC, MAPK3, EVPL, KLRC2, PIR, BCMO1, ALDH3A2, LOC729660, GSTZ1, SPOCK1, CD36, NICN1, PDPK1, TNFAIP6, ACAA2, MGST2, OXR1, KIAA1370, TFPI, IL17C, G6PD, SEPX1, LOC653778, PEG10, UBR5, LOC653924, HBP1, NOX5, RRM2B, ZFPM1, XIST, ACY1, MFSD3, METRNL, SOD2, VAV3, SLC16A4, LOC653506, LOC147645, PON2, ACTA2, LOX, PDGFC, CRIP1, PCSK5, CCNG2, NEBL, KLK6, SETD6, PTPN22, ACOX2, SLC9A3R1, C4orf34, RICS, GSTK1, GLB1L2, LOC100133511, MGST1, PTGES, ITM2C, KHDRBS3, NET1, BCKDHA, NR4A2, SLC16A14, SERPINB4, GPR110, CDC42EP4, GRTP1, ETFDH, BIN1, CYP1A1, ST6GAL1, ABLIM3, KDELC2, SEMA3C, MGC42367, PAM, NME3, DPP7, C10orf59, C12orf36, TMC4, TM7SF2, NUP210, APRT, MYEOV, LIPK, LOC93622, WNT5A, TMEM187, MEST, LOC285095, MFI2, HIST1H1C, LOC654103, LOC387825, TMPRSS3, LOC646836, MANSC1, FAP, HCFC1R1, FERMT2, FARP1, LOC729985, FLJ12684, ALDH5A1, TIMP2, BNIP3L, TRIM4, CELSR3, LOC651524, NLGN4X, GCNT3, TSKU, P4HTM, ZFP90, SPESP1, BSPRY, SHRM, CST6, TBL1X, KRT80, AMFR, OKL38, YPEL3, CLCN3, FLJ20273, SLITRK6, GLRB, SEMA6A, UGT1A6, LUM, TRAPPC6A, SULT1A1, LOC441453, LOC653061, ITFG1, ETFB, RPL34, KIAA1147, HMGCS2, FTHL3, PLACE, NIPSNAP1, UBE2D4, DDIT4L, ASMTL, VGF, ZNF428, LOC440160, DECR1, SCARNA9, SERPINB3, LGALS7B, GLS, ANGPT1, ITFG3, HOXA5, GABRE, RNF165, SQSTM1, CBX2, FTHL11, FBP1, VASN, MFSD1, GCHFR, CYB5A, LRP3, TMEM139, F12, C3, LOC643911, TEAD2, AKR1B1, TRIB2, TLR1, METTL7A, CD163L1, RERG, OSGIN2, SLC22A18, PPARG, FTHL2, LY6E, FBLN1, ARID5B, SHROOM3, *PADI4*, ABCB6, CLDN8, SNCAIP, C5orf46, TMEM45A, PTPN20, ERBB3, LYPD3, IRX3, SEL1L3, PCOLCE2, LOC441282, PGD, SLC39A8, TJP3, TMEM42, KCNIP3, CEACAM1, PLCXD3, ARSD, LAGE3, S100A9, RAP1GAP, PPAP2B, CXADR, CYFIP2, LOC100129195, HTATIP2, GDF15, FTHL16, CLCA2, CTSD, MAFB, GPRC5C, ELF3, PDE4B, ROS1, CA2, CKLF, SYTL2, LOC652669, D2HGDH, ZNF323, PINK1, P8, HSPBL2, PLXDC2, ALDH3B1, SRGN, EGFLAM, TRIM2, RBM47, RPL28, TNFAIP2, MXD4, DECR2, TSTD1, PTK6, LPL, GCLC, CXCR7, STC1, KRT15, NOTCH3, LOC645553, CD97, RAB26, CYBRD1, KIAA0182, RPS29, S100A8, LOC341230, FBXL16, KLK5, NCOA7, LOC642567, CYP4F3, PPAP2C, ATP6V1B1, LOC653879, COL8A1, TNFSF9, NAT14, TNS3, AIF1L, GPNMB, FBXO32, HS6ST2, GNE, IL6, ARL14, FLJ10916, LOC642399, LOC392437, NQO1, ECH1, ECHDC3, DENND2D, FAM113B, LOC340274, ANKRD33, CITED2, ICA1, FXYD3, CHDH, COBL, LOC392871, NINJ1, NAMPT, LOC255326, NUPR1, CHURC1, CSGALNACT1, KRT24, HOXA10, DCN, FGF2, WFDC2, BAMBI, LXN, PNLIPRP3, CLDN1, TAGLN, ZDHHC4, GRB14, NMB, SERPINE2, CYP24A1, FLJ39632, IMPA2, CTSH, TNFRSF11B, NCCRP1, FTH1, CPVL, DIO2, EPHX1, ABCC2, SGPP2, DBNDD1, PDK4, AZGP1, CRABP2, IRX5, LEMD1, CD14, CHCHD10, CTXN1, CLIC3, ASS1, LOC642477, C15orf48, USMG5, TXNIP, LCP1, C19orf46, KRTCAP3, PDZK1IP1, ITGB2, BGN, LOC146909, C14orf147, ACSL1, SLC16A5, LOC100131139, ATP6V0E2, BCL6, BAIAP2L2, LOC400879, LAPTM4B, LCN2, GBP2, M160, NME4, CCL20, CFD, MARCKSL1, ECGF1, AKR1C2, CES1, CYP4X1, CA9, FABP4, FAM46A, QPCT, ANPEP, GDPD3, LMTK3, EPDR1, PAPPA, CD70, HOXA9, C1QTNF1, PSCA, DEFB1, HRASLS3, CXXC5, LOC645638, AKR1B15, KYNU, AKR1C4, REPIN1, COX7A1, CFB, ABCC3, AKR1C3, LOC100134265, CYP1B1, S100P, TCN1, AKR1B10, MGP, CALB2, SERPINA3, MUC1, S100A7, ALDH3A1, MSLN, S100A4, IGFBP3, and RARRES1.

14. The method of claim 13, further comprising assaying the mRNA expression levels of at least 2 genes from said group.

15. The method of claim 13, further comprising assaying the mRNA expression levels of at least 3 genes from said group.

16. The method of claim 13, further comprising assaying the mRNA expression levels of at least 4 genes from said group.

17. The method of claim 13, further comprising assaying the mRNA expression levels of at least 5 genes from said group.

* * * * *